United States Patent
Zheng et al.

(10) Patent No.: US 12,339,204 B2
(45) Date of Patent: Jun. 24, 2025

(54) SIZABLE TUNABLE ENRICHMENT PLATFORM FOR CAPTURING NANO PARTICLES IN A FLUID

(71) Applicant: The Penn State Research Foundation, University Park, PA (US)

(72) Inventors: Siyang Zheng, State College, PA (US); Mauricio Terrones, State College, PA (US); Yin-Ting Yeh, State College, PA (US); Yi Tang, State College, PA (US); Huaguang Lu, State College, PA (US); Nestor Perea Lopez, State College, PA (US); Yiqiu Xia, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 1100 days.

(21) Appl. No.: 17/236,814

(22) Filed: Apr. 21, 2021

(65) Prior Publication Data

US 2021/0302287 A1  Sep. 30, 2021

Related U.S. Application Data

(62) Division of application No. 16/784,507, filed on Feb. 7, 2020, now Pat. No. 11,022,529, which is a division
(Continued)

(51) Int. Cl.
*G01N 1/40* (2006.01)
*B01L 3/00* (2006.01)
(Continued)

(52) U.S. Cl.
CPC ........ *G01N 1/405* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

2006/0238096 A1  10/2006  Han et al.
2007/0116631 A1   5/2007  Li
(Continued)

FOREIGN PATENT DOCUMENTS

WO    2011133015 A2   10/2011

OTHER PUBLICATIONS

Zhang et al., "Substitutional Doping of Carbon Nanotubes with Heteroatoms and Their Chemical Applications", ChemSusChem, vol. 7 (2014); pp. 1240-1250 (Year: 2014).
(Continued)

*Primary Examiner* — Matthew D Krcha
(74) *Attorney, Agent, or Firm* — Buchanan Ingersoll & Rooney PC

(57) ABSTRACT

The invention provides enrichment platform devices for size-based capture of particles in solution. The enrichment platform device is useful for label-free capture of any particle. The invention relates to enrichment platform devices using nanowires and vertically aligned carbon nanotubes. The invention provides methods for making the enrichment platform devices. The invention provides methods for using the enrichment platform devices for filtering particles, capturing particles, concentrating particles, and releasing viable particles.

18 Claims, 59 Drawing Sheets

Related U.S. Application Data of application No. 15/213,128, filed on Jul. 18, 2016, now Pat. No. 10,598,575.

(60) Provisional application No. 62/193,876, filed on Jul. 17, 2015.

(51) Int. Cl.

| | |
|---|---|
| *G01N 33/543* | (2006.01) |
| *G01N 33/552* | (2006.01) |
| *G01N 33/569* | (2006.01) |
| *B82Y 30/00* | (2011.01) |

(52) U.S. Cl.
CPC ... *B01L 3/502753* (2013.01); *B01L 3/502761* (2013.01); *G01N 1/4077* (2013.01); *G01N 33/54346* (2013.01); *G01N 33/552* (2013.01); *G01N 33/56983* (2013.01); *B01L 2200/0668* (2013.01); *B01L 2200/12* (2013.01); *B01L 2300/041* (2013.01); *B01L 2300/0681* (2013.01); *B01L 2300/0896* (2013.01); *B01L 2300/12* (2013.01); *B82Y 30/00* (2013.01); *G01N 2001/4088* (2013.01); *G01N 2333/11* (2013.01)

(56) References Cited

U.S. PATENT DOCUMENTS

| | | |
|---|---|---|
| 2008/0090183 A1 | 4/2008 | Zhu |
| 2013/0244008 A1 | 9/2013 | Wardke et al. |
| 2014/0030788 A1* | 1/2014 | Chen ............... B01L 3/502746 435/308.1 |
| 2014/0079601 A1 | 3/2014 | Rubner et al. |

OTHER PUBLICATIONS

Koos et al., "Effect of the Experimental Parameters on the Structure of Nitrogen-Doped Carbon Nanotubes Produced by Aerosol Chemical Vapour Desposition", Carbon, vol. 47 (2009); pp. 30-37, (Year: 2009).
Capua et al., "Prevention and Control of Highly Pathogenic Avian Influenza with Particular Refernce to H5N1", Virus Research, vol. 178 (2013); pp. 114-120.
Bibby, Metagenomic identification of viral pathogens. Trends Biotechnol. 31, 275-279 (2013).
Daly et al. A Viral Discovery Methodology for Clinical Biopsy Samples Utilising Massively Parallel Next Generation Sequencing. PLoS ONE 6, e28879 (2011).
Hall et al. Evaluation of rapid and simple techniques for the enrichment of viruses prior to metagenomic virus discovery. J. Virol. Methods 195, 194-204 (2014).
Rosseel et al. Evaluation of convenient pretreatment protocols for RNA virus metagenomics in serum and tissue samples. J. Virol. Methods 222, 72-80 (2015).
Dileo et al. High Resolution Removal of Virus from Protein Solutions Using a Membrane of Unique Structure. Nat. Biotech. 10, 182-188 (1992).
De Heer et al. A Carbon Nanotube Field-Emission Electron Source. Science 270, 1179-1180 (1995).
Lee et al. Amine-modified single-walled carbon nanotubes protect neurons from injury in a rat stroke model. Nat. Nano. 6, 121-125 (2011).
Kue et al. Aggregated single-walled carbon nanotubes attenuate the behavioural and neurochemical effects of methamphetamine in mice. Nat. Nano., (2016).
Reyes-Reyes et al. Efficient encapsulation of gaseous nitrogen inside carbon nanotubes with bamboo-like structure using aerosol thermolysis. Chem. Phys. Lett. 396, 167-173 (2004).
Villalpando-Paez et al. Synthesis and characterization of long strands of nitrogen-doped single-walled carbon nanotubes. Chem. Phys. Lett. 424, 345-352 (2006).
Sumpter et al. Nitrogen-mediated carbon nanotube growth: diameter reduction, metallicity, bundle dispersability, and bamboo-like structure formation. ACS nano 1, 369-375 (2007).
Mihalchik et al. Effects of nitrogen-doped multi-walled carbon nanotubes compared to pristine multi-walled carbon nanotubes on human small airway epithelial cells. Toxicology 333, 25-36 (2015).
Deheer et al. Aligned Carbon Nanotube Films: Production and Optical and Electronic Properties. Science 268, 845-847 (1995).
Mizuno et al. A black body absorber from vertically aligned single-walled carbon nanotubes. Proc. Natl. Acad. Sci. U. S. A. 106, 6044-6047 (2009).
Yang et al. Experimental Observation of an Extremely Dark Material Made by a Low-Density Nanotube Array. Nano Lett. 8, 446-451 (2008).
Gao et al. Human Infection with a Novel Avian-Origin Influenza A (H7N9) Virus. New Engl. J. Med. 368, 1888-1897 (2013).
WHO, "World health report—A safer future: global public health security in the 21st century," (Geneve, 2007).
Yang et al. Immunization by avian H5 influenza hemagglutinin mutants with altered receptor binding specificity. Science 317, 825-828 (2007).
Acevedo et al. Library preparation for highly accurate population sequencing of RNA viruses. Nat. Protocols 9, 1760-1769 (2014).
Qian et al. Mechanics of carbon nanotubes. Appl. Mech. Rev. 55, 495-533 (2002).
Ganesan et al. Effect of Nitrogen Doping on the Mechanical Properties of Carbon Nanotubes. ACS Nano 4, 7637-7643 (2010).
Kia et al. Soft lithography. Annu. Rev. Mater. Sci. 28, 153-184 (1998).
Bankhead, Analyzing fluorescence microscopy images with ImageJ. (2014).
Wang et al. Label-free imaging, detection, and mass measurement of single viruses by surface plasmon resonance. Proc. Natl. Acad. Sci. U.S. A. 107, 16028-16032 (2010).
Reed et al. A simple method of estimating fifty per cent endpoints. Am. J. Epidemiol. 27, 493-497 (1938).
Bankevich et al. SPAdes: a new genome assembly algorithm and its applications to single-cell sequencing. J. Comp. Biol. 19, 455-477 (2012).
Harris, Improved pairwise alignment of genomic DNA. (ProQuest, 2007).
Li et al. The sequence alignment/map format and SAMtools. Bioinformatics 25, 2078-2079 (2009).
Kumar et al. MEGA: molecular evolutionary genetics analysis software for microcomputers. Computer applications in the biosciences: CABIOS 10, 189-191 (1994).
Tamura et al. MEGA5: molecular evolutionary genetics analysis using maximum likelihood, evolutionary distance, and maximum parsimony methods. Mol. Biol. Evol. 28, 2731-2739 (2011).
Quail et al. A tale of three next generation sequencing platforms: comparison of Ion Torrent, Pacific Biosciences and lumina MiSeq sequencers. BMC genomics 13, 341 (2012).
Cingolani et al. A program for annotating and predicting the effects of single nucleotide polymorphisms, SnpEff: SNPs In the genome of *Drosophila melanogaster* strain w1118; iso-2; iso-3. (2012).
Krzywinski et al. Circos: an information aesthetic for comparative genomics. Genome Res. 19, 1639-1645 (2009).
Bohonak et al. Compaction and permeability effects with virus filtration membranes. L. Membrane Sci. 254, 71-79 (2005).
Van Holten et al. Incorporation of an additional viral-clearance step into a human immunoglobulin manufacturing process. Vox Sang. 83, 227-233 (2002).
Yang et al. Nanoporous Membranes with Ultrahigh Selectivity and Flux for the Filtration of Viruses. Adv. Mater. 18, 709-712 (2006).
Desai et al. Nanoporous anti-fouling silicon membranes for biosensor applications. Biosens. Bioelectron. 15, 453-462 (2000).
Mueller et al. Variables Influencing Extraction of Nucleic Acids from Microbial Plankton (Viruses, Bacteria, and Protists) Collected on Nanoporous Aluminum Oxide Filters. Appl. Environ. Microb. 80, 3930-3942 (2014).

(56) References Cited

OTHER PUBLICATIONS

Palacio et al. Porosity measurements by a gas penetration method and other techniques applied to membrane characterization. Thin Solid Films 348, 22-29 (1999).
Thormann et al. Nanoporous Aluminum Oxide Membranes for Filtration and Biofunctionalization. Small 3, 1032-1040 (2007).
Urase et al. Effect of pore structure of membranes and module configuration on virus retention. L. Membrane Sci. 115, 21-29 (1996).
Syedain et al. Protein fouling of virus filtration membranes: Effects of membrane orientation and operating conditions. Biotechnol. Progr. 22, 1163-1169 (2006).
Gere et al. Mechanics of Materials, 8th ed., (Cengage Learning, Boston, MA, 2012).
Pennington., "Politics, media and microbiologists," Nature Reviews Microbiology, vol. 2, pp. 259-262 (2004).
Qu et al., "Electrically Conductive and Optically Active Porous Silicon Nanowires," Nano Letters, vol. 9, No. 12, pp. 4539-4543 (2009).
Qu et al., "Porous silicon nanowires," Nanoscale, No. 3, pp. 4060-4068 (2011).
Lamb et al., "The Gene Structure and Replication of Influenza Virus," Annual Review of Biochemistry, No. 52, pp. 467-506 (1983).
Balasubramanian et al., "Biosensors based on carbon nanotubes," Analytical and Bioanalytical Chemistry, No. 385, pp. 452-468 (2006).
Baughman et al., "Carbon nanotubes—the route toward applications," Science, vol. 297, pp. 787-792 (2002).
Bedewy, et al., "Collective mechanism for the evolution and self-termination of vertically aligned carbon nanotube growth," The Journal of Physical Chemistry, No. 113, pp. 20576-20582 (2009).
Benfield et al., "Characterization of swine infertility and respiratory syndrome (SIRS) virus (isolate ATCC VR-2332)," Journal of Veterinary Diagnostic Investigation, No. 4, pp. 127-133 (1992).
Binder et al., "Emerging Infectious Diseases: Public Health Issues for the 21st Century," Science, No. 284 (5418), 1311-1313 (1999).
Bouvier et al., "The biology of influenza viruses," Vaccine, No. 26S, pp. D49-D53 (2008).
Bray et al., "Quantifying nanoparticle dispersion by using the area disorder of Delaunay triangulation," Journal of the Royal Statistical Society, No. 61, Part 2, pp. 253-275 (2012).
Cai et al., "Highly efficient molecular delivery into mammalian cells using carbon nanotube spearing," Nature Methods, vol. 2, No. 6, pp. 449-454 (2005).
Chen et al., "Nanoporous micro-element arrays for particle interception in microfluidic cell separation," Lab on a Chip, No. 12, pp. 3159-3167 (2012).
Chen et al., "Nanoporous elements in microfluidics for multiscale manipulation of bioparticles," Small 7, No. 8, pp. 1061-1067 (2011).
Chen et al., "Silicon Nanowire Field-Effect Transistor-Based Biosensors for Biomedical Diagnosis and Cellular Recording Investigation," Nano Today, No. 6, pp. 131-154 (2011).
Chiappini et al., "Biodegradable Porous Silicon Barcode Nanowires with Defined Geometry," Advanced Functional Materials, No. 20, pp. 2231-2239 (2010).
Patolsky et al., "Fabrication of silicon nanowire devices for ultrasensitive, label-free, real-time detection of biological and chemical species, " Nat. Protocols, vol. 1, No. 4, pp. 1711-1724 (2006).
Collins et al., "Isolation of Swine Infertility and Respiratory Syndrome Virus (Isolate ATCC VR-2332) in North America and Experimental Reproduction of the Disease in Gnotobiotic Pigs," Journal of Veterinary Diagnostic Investigation, No. 4, pp. 117-126 (1992).
Dai., "Carbon nanotubes: synthesis, integration, and properties," Accounts of Chemical Research, No. 35, pp. 1035-1044 (2002).
Di Carlo., "Inertial microfluidics," Lab on a Chip, No. 9, pp. 3038-3046 (2009).
Di Carlo et al., "Continuous inertial focusing, ordering, and separation of particles in microchannels," Proceedings of the National Academy of Sciences, vol. 104, No. 48, pp. 18892-18897 (2007).
Eisfeld et al., "Influenza A virus isolation, culture and identification," Nature protocols, vol. 9, No. 11, pp. 2663-2681 (2014).
Stern et al., "Label-free immunodetection with CMOS-compatible semiconducting nanowires", Nature Publishing Group, vol. 445, pp. 519-522 (2007).
Fauci et al., "The Perpetual Challenge of Infectious Diseases," New England Journal of Medicine, No. 366;5, pp. 154-461 (2012).
Felsenstein., "Confidence limits on phylogenies: an approach using the bootstrap," Evolution, vol. 39, No. 4, pp. 783-791 (1985).
Green et al., "Manipulation and trapping of sub-micron bioparticles using dielectrophoresis, " Journal of Biochemical and Biophysical Methods, 1997, No. 35, pp. 89-102 (1997).
Herring et al., "Rapid diagnosis of rotavirus infection by direct detection of viral nucleic acid in silver-stained polyacrylamide gels," Journal of Clinical Microbiology, vol. 16, No. 3, pp. 473-477 (1982).
Hirst., "The Quantitative Determination of Influenza Virus and Antibodies by Means of Red Cell Agglutination," The Journal of Experimental Medicine, No. 75 (1), pp. 49-64 (1942).
Ho et al., "Inertial migration of rigid spheres in two-dimensional unidirectional flows," Journal of Fluid Mechanics, vol. 65, pp. 365-400 (1974).
Hochbaum et al., "Single Crystalline Mesoporous Silicon Nanowires," NaNo. Letters, vol. 9, No. 10, pp. 3550-3554 (2009).
Hofmann et al., "State of transition metal catalysts during carbon nanotube growth," The Journal of Physical Chemistry No. 113, pp. 1648-1656 (2009).
Horimoto et al., "Influenza: lessons from past pandemics, warnings from current incidents," Nature Reviews Microbiology, vol. 3, pp. 591-600 (2005).
Hou et al., "Isolation and retrieval of circulating tumor cells using centrifugal forces," Scientific Reports, No. 3: 1259, pp. 1-8 (2013).
Karabacak et al., "Microfluidic, marker-free isolation of circulating tumor cells from blood samples," Nature Protocols, vol. 9, No. 3 pp. 694-710 (2014).
Khan et al., "Spread of a Novel Influenza A (H1N1) Virus via Global Airline Transportation," New England Journal of Medicine, No. 361;2, pp. 212-214 (2009).
Kim et al., "Quantum dot-based HIV capture and imaging in a microfluidic channel," Biosensors and Bioelectronics, No. 25(1), pp. 253-258 (2009).
Layne et al., "Pandemic influenza: an inconvenient mutation," Science, No. 323(5921), pp. 1560-1561 (2009).
Lederberg et al., "Microbial Threats to Health: Emergence, Detection, and Response," National Academies Press, pp. 1-398 (2003).
Lee et al., "An integrated microfluidic system for rapid diagnosis of dengue virus infection," Biosensors and Bioelectronics, No. 25, pp. 745-752 (2009).
Leland et al., "Role of Cell Culture for Virus Detection in the Age of Technology," Clinical Microbiology Reviews, vol. 20, No. 1, pp. 49-78 (2007).
Li et al., "Growth of single-walled carbon nanotubes from discrete catalytic nanoparticles of various sizes," The Journal of Physical Chemistry, No. 105, pp. 11424-11431 (2001).
Liu et al., "Carbon Nanotubes in Biology and Medicine: In vitro and in vivo Detection, Imaging and Drug Delivery," Nano Res., No. 2, pp. 85-120 (2009).
Lu et al., "Studies on Multiplex RT-PCR for Detection of Avian Influenza Virus Type A Group and Specific H5 and H7 Subtypes," Journal of Veterinary Science & Medicine, No. 1(2): 5 (2013).
Martel et al., "Particle Focusing in Curved Microfluidic Channels," Scientific Reports, vol. 3: 3340 (2013).
Matas et al., "Lateral force on a rigid sphere in large-inertia laminar pipe flow," Journal of Fluid Mechanics, vol. 621, pp. 59-67 (2009).
Matas et al., "Inertial migration of rigid spherical particles in Poiseuille flow" Journal of Fluid Mechanics, vol. 515, pp. 171-195 (2004).
Zahedinejad et al., "Successful definition of nanowire and porous Si regions of different porosity levels by regular positive photoresist

(56) References Cited

OTHER PUBLICATIONS using metal-assisted chemical etching," Journal of Micromechanics and Microengineering, No. 21 (2011).
Morens et al., "Emerging Infectious Diseases: Threats to Human Health and Global Stability," PLoS Pathogens, vol. 9, No. 7 (2013).
Morgan et al., "Separation of Submicron Bioparticles by Dielectrophoresis," Biophysical Journal, vol. 77, pp. 516-525 (1999).
Radford et al., "Application of next-generation sequencing technologies in virology," Journal of General Virology, No. 93, pp. 1853-1868 (2012).
Reimer et al., "Influenza virus purification with the zonal ultracentrifuge," Science, New Series, vol. 152, No. 3727, pp. 1379-1381 (1966).
Ren et al., "Synthesis of large arrays of well-aligned carbon nanotubes on glass," Science, vol. 282, pp. 1105-1107 (1998).
Ritzi-Lehnert., "Development of chip-compatible sample preparation for diagnosis of infectious diseases," Expert Review of Molecular Diagnostics, vol. 12.2, pp. 189-206 (2012).
Seah et al., "Synthesis of aligned carbon nanotubes," Carbon, vol. 49, pp. 4613-4635 (2011).
Shortridge et al., "Characterization of avian H5N1 influenza viruses from poultry in Hong Kong," Virology, No. 252, pp. 331-342 (1998).
Shiu et al. "Influence of pre-surface treatment on the morphology of silicon nanowires fabricated by metal-assisted etching, " Applied surface science, vol. 257, pp. 1829-1834 (2011).
Sin et al., "Advances and challenges in biosensor-based diagnosis of infectious diseases," Expert Review of Molecular Diagnostics, No. 14(2), pp. 225-224 (2014).
Spackman et al., "Development of a Real-Time Reverse Transcriptase PCR Assay for Type A Influenza Virus and the Avian H5 and H7 Hemagglutinin Subtypes," Journal of Clinical Microbiology, vol. 40, No. 9, pp. 3256-3260 (2002).
Tam et al., "DNA sensor development based on multi-wall carbon nanotubes for label-free influenza virus (type A) detection," Journal of Immunological Methods, vol. 350, pp. 118-124 (2009).
Thurber et al., "Laboratory procedures to generate viral metagenomes," Nature protocols, vol. 4, No. 4, pp. 470-483 (2009).
Wan et al., "Surface-Immobilized Aptamers for Cancer Cell Isolation and Microscopic Cytology," American Association for Cancer Research, No. 70(22), pp. 9371-9380 (2010).
Wang et al., "Ciliated micropillars for the microfluidic-based isolation of nanoscale lipid vesicles," Lab on a Chip, No. 13, pp. 2879-2882 (2013).
Webby et al., "Are we ready for pandemic influenza?" Science, No. 302, pp. 1519-1522 (2003).
Webster et al., "H5N1 influenza-continuing evolution and spread," New England Journal of Medicine, No. 355;21, pp. 2174-2177 (2006).
Webster et al., "Raman Characterization of Nitrogen Doped Multiwalled Carbon Nanotubes," Nanotube Based Devices, EDs. Bernier, Carroll, Kim, Roth, MRS symposium proceedings vol. 772, (2003) 129-134.
Whitesides., "The origins and the future of microfluidics" Nature, vol. 442, pp. 368-373 (2006).
Wilson., "The traveller and emerging infections: sentinel, courier, transmitter," Journal of Applied Microbiology, No. 94, pp. 1-11 (2003).
Wilson et al., "Actionable Diagnosis of Neuroleptospirosis by Next-Generation Sequencing," New England Journal of Medicine, No. 370;25, pp. 2408-2417 (2014).
Xia et al., "In a mcirofluidic device of biodegradable porous silicon nanowires for size based capturing and releasing viruses", Transducers, pp. 444-447 (2015).
Yamada et al., "Size-selective growth of double-walled carbon nanotube forests from engineered iron catalysts," Nature Nanotechnology, vol. 1, pp. 131-136 (2006).
Yeh et al., "In Microfluidic device with carbon nanotube channel walls for blood plasma extraction" Micro Electro Mechanical Systems (MEMS), pp. 951-954 (2013).
Yeh et al., "In a VACNT integrated handheld device for label-free virus capture, detection and enrichment for genomic analysis," Transducers, pp. 747-750 (2015).
Yeh et al., "In Nanomaterial integrated microfluidic devices for virus analysis," Sensors, pp. 1-4 (2015).
Yeh et al., "Point-of-care microdevices for blood plasma analysis in viral infectious diseases," Annals of Biomedical Engineering, vol. 42, No. 11, pp. 2333-2343 (2014).
Yu et al., "Strength and breaking mechanism of multiwalled carbon nanotubes under tensile load," Science, vol. 287, No. 5453, pp. 637-640 (2000).
Zhang et al., "Silicon nanowire biosensor and its applications in disease diagnostics: a review," Analytica Chimica Acta vol. 749, pp. 1-15 (2012).
Zhang et al., "Silicon nanowire biosensor for highly sensitive and rapid detection of Dengue virus," Sensors and Actuators B: Chemical, No. 146, pp. 138-144 (2010).
Wang et al. "Ciliated micropillars for the microfluidic-based isolation of nanoscale lipid vesicles", Lab on a chip, vol. 13, pp. 2879, 2013.
USDA, Update on the Highly-Pathogenic Avian Influenza Outbreak of 2014-2015.
Ellis et al., "Molecular diagnosis of influenza," Review in Medical Virology, No. 12, pp. 375-389 (2002).
Wood et al., "From lethal virus to life-saving vaccine: developing inactivated vaccines for pandemic influenza," Nature Reviews Microbiology, vol. 2, pp. 842-847 (2004).
Chiu., "Viral pathogen discovery," Current Opinion Microbiology, No. 16, pp. 468-478 (2013).
Anthony et al., "A Strategy to Estimate Unknown Viral Diversity in Mammals," mBio, vol. 4, No. 5, pp. 1-15 (2013).
Woolhouse et al., "Chase-Topping, Human viruses: discovery and emergence, "Philosophical Transactions of the Royal Society B, No. 367, pp. 2864-2871 (2012).
Howard et al., "Emerging virus diseases: can we ever expect the unexpected?" Emerging Microbes and Infectections, No. 1, e46 (2012).
Woolhouse et al., "Host Range and Emerging and Reemerging Pathogens," Emerging Infectious Diseases, vol. 11, No. 12, pp. 1842-1847 (2005).
King et al., "Infectious Diseases: Preparing for the Future," Science, New Series, vol. 313, No. 5792, pp. 1392-1393 (2006).
Yolken., "Enzyme-Linked Immunosorbent-Assay (ELISA)—A Practical Tool for Rapid Diagnosis of Viruses and Other Infectious Agents," The Yale Journal of Biology and Medicine, No. 53, pp. 85-92 (1980).
Beerenwinkel et al., "Challenges and opportunities in estimating viral genetic diversity from next-generation sequencing data," Frontiers in Microbiology, vol. 3, No. 329 (2012).
Chin et al., "Commercialization of microfluidic point-of-care diagnostic devices," Lab on a Chip, No. 12, pp. 2118-2134 (2012).
Heider et al., 'Quantitative real-time single particle analysis of virions, Virology, Nos. 462-463, pp. 199-206 (2014).
Li et al., "Comparing viral metagenomics methods using a highly multiplexed human viral pathogens reagent," Journal of Virological Methods, No. 213, pp. 139-146 (2015).
Noda., "Native morphology of influenza virions," Frontier in Microbiology, vol. 2, No. 269, pp. 1-5 (2011).
Van Reis et al., "Bioprocess membrane technology," Journal of Membrane Science, No. 297, pp. 16-50 (2007).
Yeh et al., "Point-of-Care Microdevices for Blood Plasma Analysis in Viral Infectious Diseases," Annals of Biomedical Engineering, vol. 42, No. 1, pp. 2333-2343 (2014).
Stroock et al., "Chaotic mixer for microchannels," Science, vol. 295, pp. 647-651 (2002).
Alexander et al., "Highly pathogenic avian influenza outbreaks in Europe, Asia, and Africa since 1959, excluding the Asian H5N1 virus outbreaks," Avian influenza 1, pp. 217-237 (2008).
Anderson et al., "Dissolution of different forms of partially porous silicon wafers under simulated physiological conditions," Physica Status Solidi (a) 197, No. 2, pp. 331-335 (2003).

(56) References Cited

OTHER PUBLICATIONS

Asmolov., "The inertial lift on a spherical particle in a plane Poiseuille flow at large channel Reynolds number," Journal of Fluid Mechanics, vol. 381, pp. 63-87 (1999).

* cited by examiner

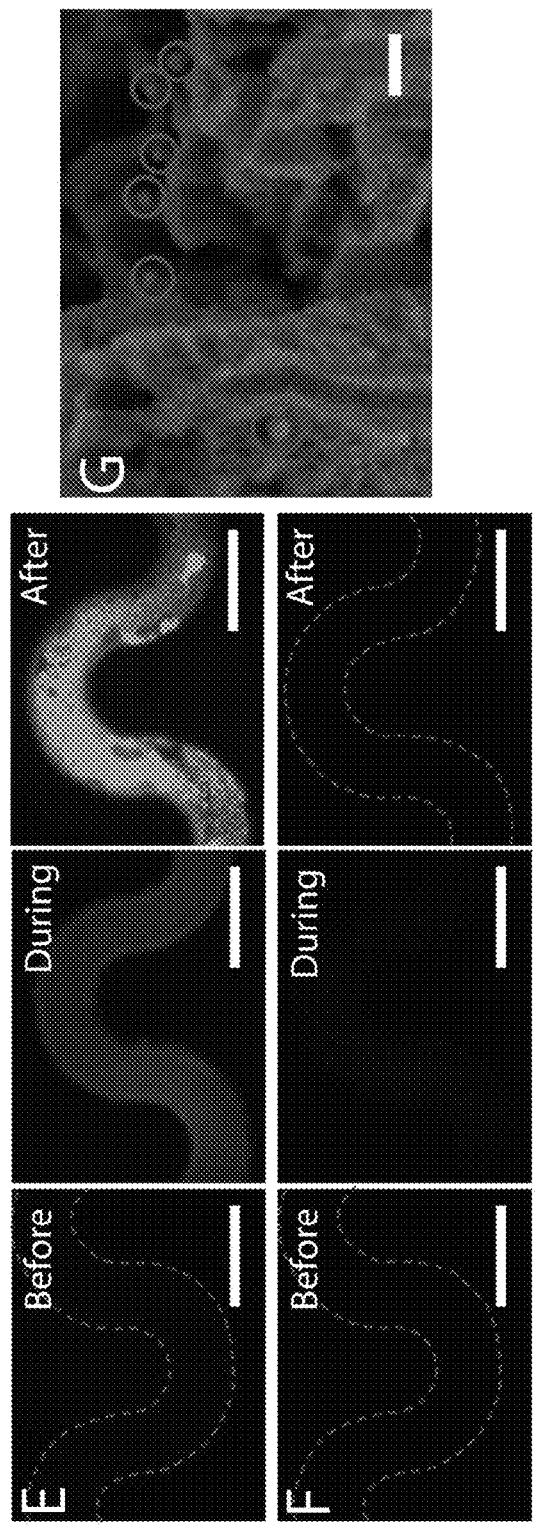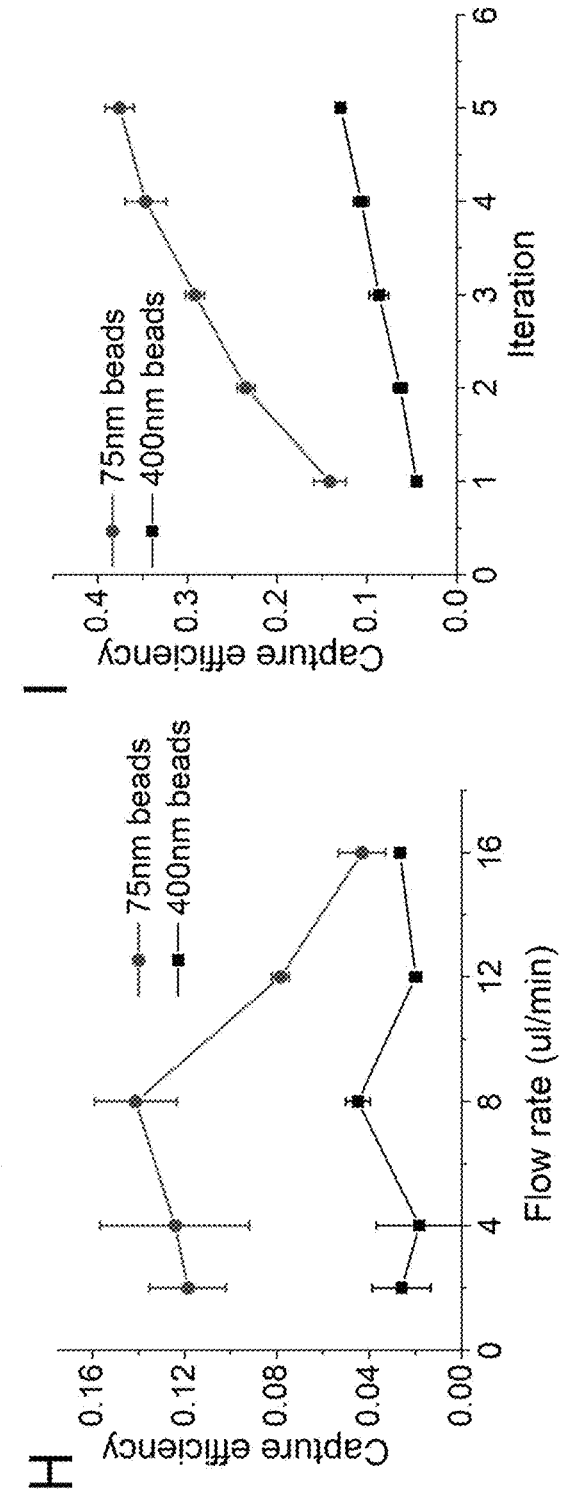
Figure 10E – 10I

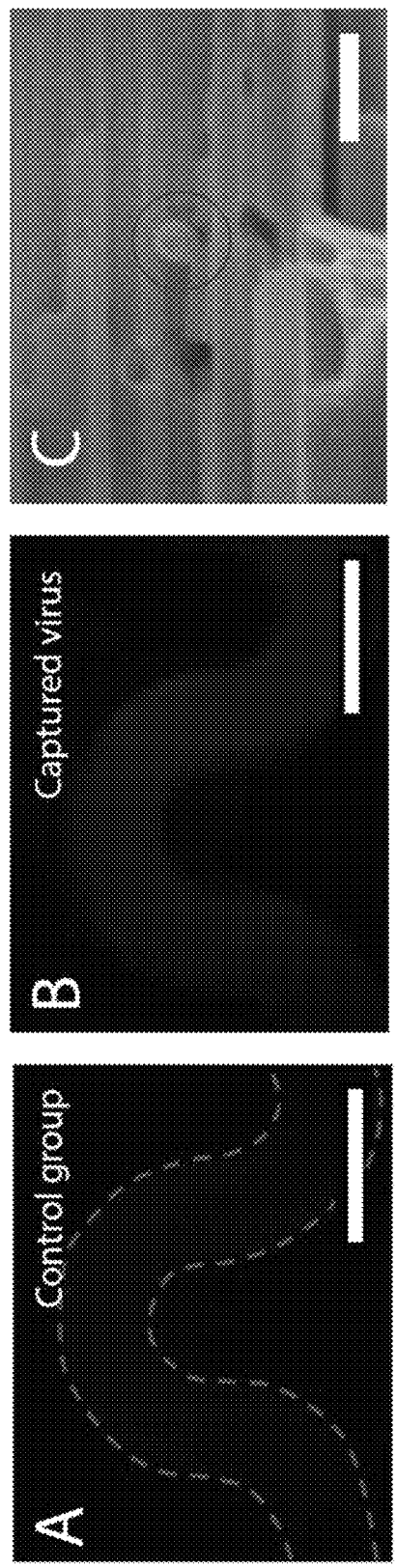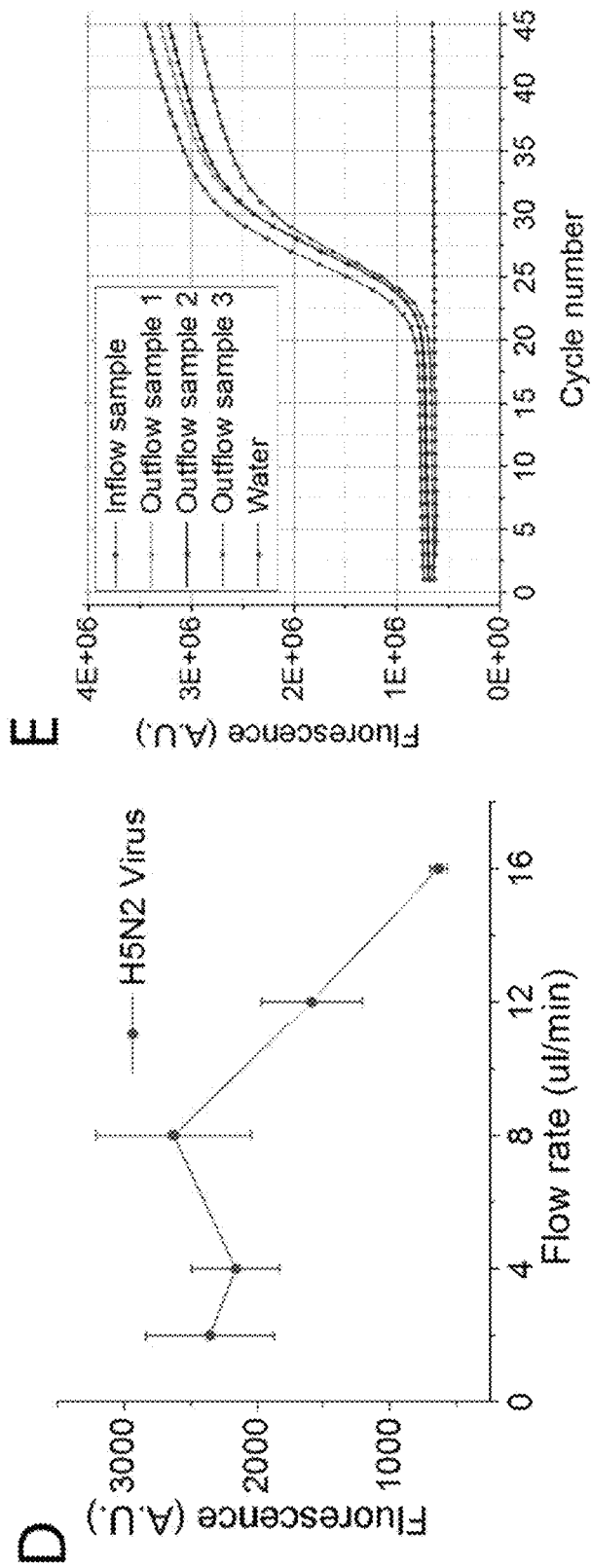
Figure 12A – 12E

|  | Initial volume | CT value | Diluted volume for RT qPCR | Percentage of out flow virus | Capture efficiency |
|---|---|---|---|---|---|
| Inflow sample | 40 μl | 19.40 | 250 μl |  |  |
| Outflow sample 1 | 250 μl | 20.47 | 250 μl | 47.6% | 52.4% |
| Outflow sample 2 | 250 μl | 20.25 | 250 μl | 55.5% | 44.5% |
| Outflow sample 3 | 250 μl | 20.40 | 250 μl | 50.0% | 50.0% |

Figure 13

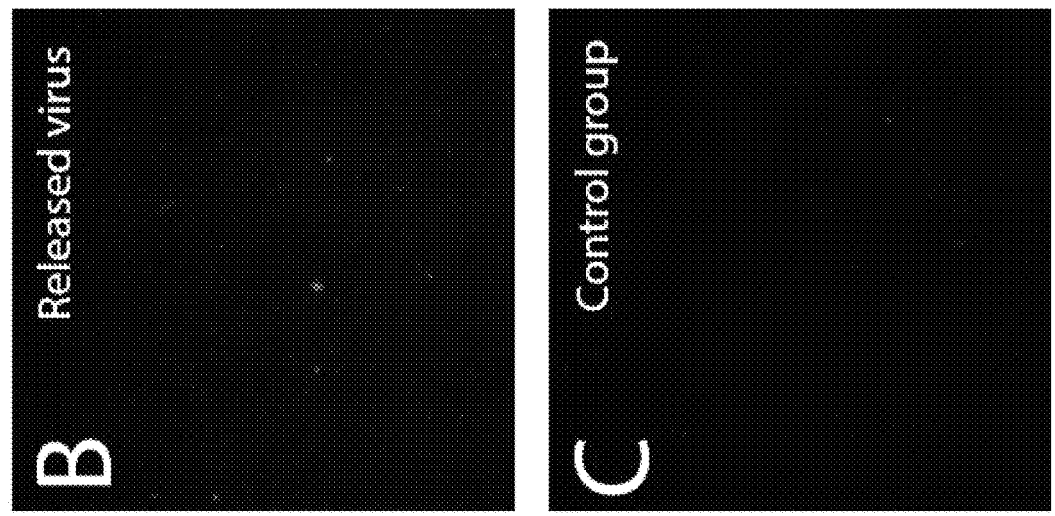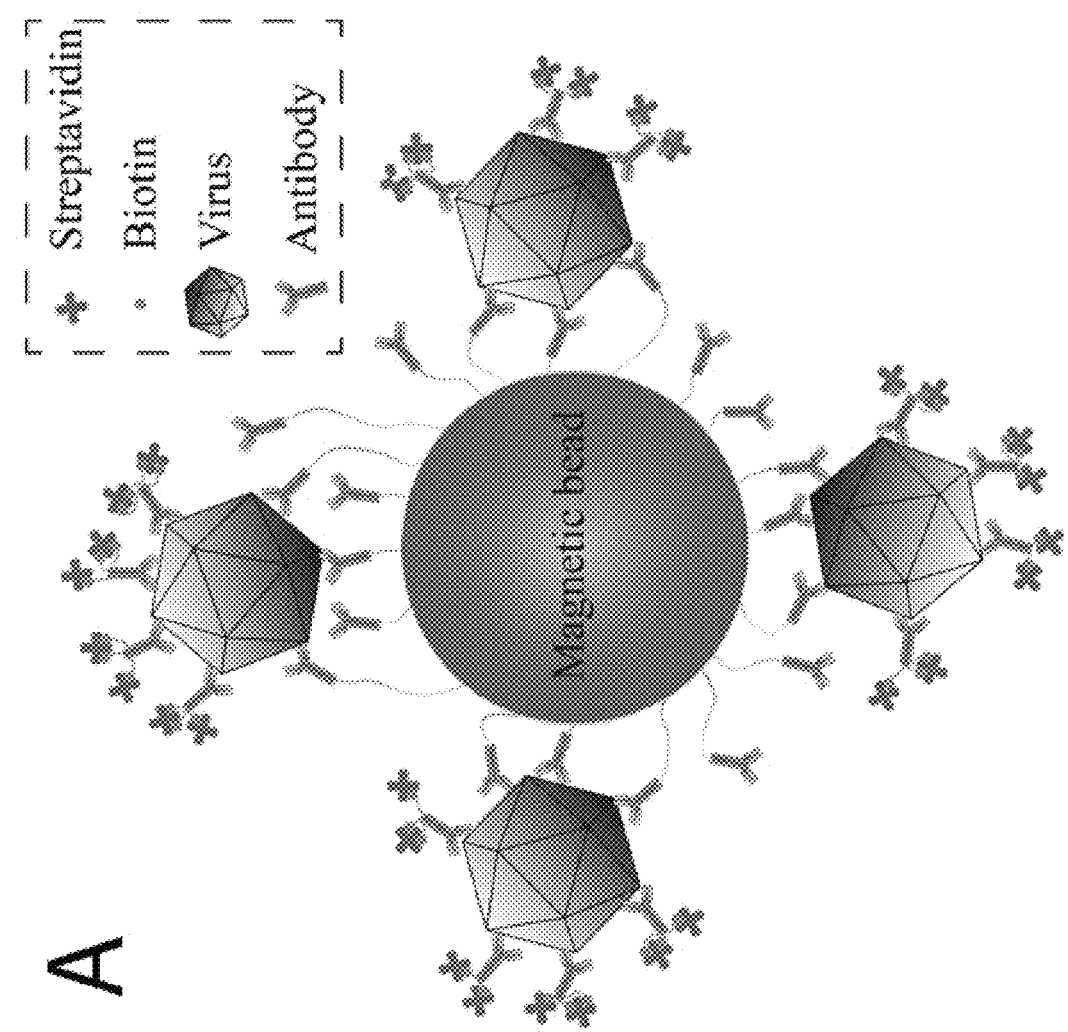
Figure 15A – 15C

| | Initial volume | CT value | Diluted volume for RT qPCR | Capture efficiency |
|---|---|---|---|---|
| Inflow sample A | 120 μl | 15.92 | 120 μl | |
| Recovery sample A1 | 60 μl | 17.43 | 60 μl | 17.6% |
| Recovery sample A2 | 60 μl | 16.33 | 60 μl | 37.6% |
| Recovery sample A3 | 60 μl | 16.61 | 60 μl | 31.0% |
| Inflow sample B | 40 μl | 15.92 | 40 μl | |
| Recovery sample B | 400 μl | 21.6 | 400 μl | 29.2% |
| Inflow sample B | 40 μl | 19.40 | 250 μl | |
| Recovery sample B | 1000 μl | 23.55 | 1000 μl | 28.2% |

| Iron catalyst thickness (nm) | N-MWCNT | | Critical particle sizes of CNT-STEM (nm) |
| --- | --- | --- | --- |
| | Inter-tubular distance (nm) | Standard deviation (nm) | |
| 1 | 17 | 6 | - |
| 3 | 25 | 10 | ~35 |
| 6.5 | 95 | 25 | ~80 |
| 9 | 194 | 40 | - |
| 12 | 325 | 56 | ~225 |

| Segment | Contig length (nt) | Ave. seq. depth (min/max) | Closest H5N2 strain in Genbank | | | |
|---|---|---|---|---|---|---|
| | | | Highest similarity strain (sequence ID) | Length (nt) | Identities | Gaps |
| PB2 | 2316 | 8446±4870<br>(3427/25340) | A/turkey/MN/3689-1551/1982(H5N2)<br>(EU743285) | 2315 | 99%<br>(2315/2316) | 0/231<br>6 |
| PB1 | 2316 | 10388±3464<br>(3376/22974) | A/turkey/MN/3689-1551/1982(H5N2)<br>(EU743284) | 2306 | 99%<br>(2305/2306) | 0/230<br>6 |
| PA | 2259 | 12334±2268<br>(1935/18966) | A/mallard/New York/189/1982(H5N2)<br>(CY014854) | 2225 | 99%<br>(2204/2225) | 0/222<br>5 |
| HA | 1742 | 12221±2751<br>(1820/18275) | A/mallard/WI/411/1981(H5N2)<br>(CY179411) | 1742 | 99%<br>(1732/1742) | 0/174<br>2 |
| NP | 1633 | 13921±3190<br>(1453/21459) | A/turkey/MN/3689-1551/1982(H5N2)<br>(EU743282) | 1539 | 100%<br>(1539/1539) | 0/153<br>9 |
| NA | 1452 | 12819±2835<br>(729/18292) | A/G-W teal/WI/432/1981(H5N2)<br>(CY179405) | 1442 | 99%<br>(1437/1439) | 0/143<br>9 |
| M1/M2 | 1047 | 15646±3986<br>(2241/28076) | A/turkey/MN/1598/1981(H5N2)<br>(CY014761) | 1015 | 99%<br>(1013/1015) | 0/101<br>5 |
| NS1/NS2 | 905 | 14804±4022<br>(1138/22400) | A/turkey/MN/3689-1551/1981(H5N2)<br>(U85382) | 865 | 100%<br>(865/865) | 0/865 |
| *Total* | *13670* | | | *13450* | | *0* |

| Segment | Contig length (nt) | Ave. seq. depth (min/max) | Closest H5N2 strain in Genbank | | | |
|---|---|---|---|---|---|---|
| | | | Highest similarity strain (sequence ID) | Length (nt) | Identities | Gaps |
| PB2 | 2324 | 13±2 (1/25) | A/blue-winged Teal/North Dakota/A

A) HA

% Nucleotide identity

| Strain | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1 | *** | 99.9 | 99.3 | 98.3 | 98.1 | 98.1 | 97.9 | 97.8 | 97.7 | 97.3 | 97.3 | 96.5 | 95.9 | 92.8 |
| 2 | 99.7 | *** | 99.2 | 98.1 | 97.9 | 98 | 97.7 | 97.7 | 97.6 | 97.2 | 97.3 | 96.4 | 95.8 | 92.7 |
| 3 | 99.1 | 98.8 | *** | 97.6 | 97.4 | 97.5 | 97.2 | 97.4 | 97 | 96.6 | 96.7 | 95.8 | 95.3 | 92.3 |
| 4 | 99.7 | 99.5 | 98.8 | *** | 99.3 | 96.9 | 96.6 | 96.6 | 96.4 | 96.3 | 97.5 | 96 | 95.3 | 92 |
| 5 | 99.3 | 99.1 | 98.4 | 99.3 | *** | 96.5 | 96.3 | 96.4 | 96.1 | 96.3 | 97.3 | 95.8 | 95.1 | 91.7 |
| 6 | 98.8 | 98.5 | 97.9 | 98.8 | 98.4 | *** | 99.1 | 99.1 | 98.9 | 95.9 | 95.8 | 95.1 | 94.3 | 91.5 |
| 7 | 98.5 | 98.3 | 97.6 | 98.5 | 98.1 | 98.1 | *** | 96.2 | 99 | 96.1 | 95.5 | 95 | 94.1 | 91.3 |
| 8 | 98.4 | 98.1 | 97.4 | 98.3 | 97.7 | 97.7 | 97.5 | *** | 95.9 | 95.6 | 95.9 | 95.3 | 94.6 | 91.4 |
| 9 | 98.3 | 98 | 97.3 | 98.3 | 97.9 | 98.9 | 99.2 | 97.2 | *** | 95.4 | 95.3 | 94.8 | 94 | 91.3 |
| 10 | 98.1 | 97.9 | 97.2 | 98.1 | 97.7 | 97.7 | 97.1 | 96.8 | 97.2 | *** | 98.1 | 98.5 | 97 | 93.5 |
| 11 | 98.3 | 98.3 | 97.2 | 98.3 | 97.9 | 97.7 | 97.9 | 96.7 | 96.8 | 97.7 | *** | 95.5 | 94.5 | 91.4 |
| 12 | 97.7 | 97.5 | 96.8 | 97.7 | 97.5 | 97.3 | 97.3 | 96.7 | 97.1 | 98.3 | 97.3 | *** | 96.6 | 92.8 |
| 13 | 98.7 | 98.4 | 97.7 | 98.7 | 98.3 | 98 | 97.7 | 97.2 | 97.5 | 98.4 | 97.7 | 98 | *** | 92.5 |
| 14 | 97.1 | 96.8 | 96.7 | 97.1 | 96.7 | 96.4 | 96.2 | 95.9 | 95.9 | 97.3 | 96.8 | 96.7 | 97.3 | *** |

% Amino acid identity

| Label | Strain (accession number) | Label | Strain (accession number) |
|---|---|---|---|
| 1 | A/duck/PA/2099/2012(H11N9)(KR870237) | 11 | A/mallard/MS/11OS863/2011(H11N9)(CY166760) |
| 2 | A/mallard/MN/Sg-00118/2007(H11N9)(CY078050) | 12 | A/mallard/MN/AI10-3386/2009(H11N9)(DQ424860) |
| 3 | A/Anas_acuta/NM/A00629381/2008(H11N9)(KF542875) | 13 | A/mallard/MD/538/2002(H11N9)(GQ257487) |
| 4 | A/mallard/CA/6634/2008(H11N9)(CY094125) | 14 | A/mallard/WI/456/1984(H11N9)(CY216661) |
| 5 | A/mallard/CA/10125/2008(H11N9)(CY093671) | | |
| 6 | A/shoveler/IL/10OS3619/2010(H11N9)(CY133029) | | |
| 7 | A/mallard/WI/10OS4193/2010(H11N9)(CY133045) | | |
| 8 | A/mallard/AK/44430-056/2008(H11N9)(HM193587) | | |
| 9 | A/mallard/OH/12OS4697/2012(H11N9)(CY186822) | | |
| 10 | A/mallard/MN/182722/1998(H11N9)(CY139745) | | |

% Nucleotide identity

| Strain | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 | *** | 99.8 | 99.5 | 99.5 | 99.4 | 99.4 | 99.3 | 99.2 | 98.7 | 98.7 | 98.4 | 98.3 | 98.3 | 98 | 97.7 | 97.5 | 97.4 | 97.2 |
| 2 | 99.3 | *** | 99.6 | 99.6 | 99.5 | 99.5 | 99.4 | 99.3 | 98.5 | 98.8 | 98.1 | 98.1 | 98.1 | 97.7 | 97.4 | 97.3 | 97.2 | 97 |
| 3 | 98.4 | 98.7 | *** | 100 | 99.3 | 99.7 | 99.6 | 99.5 | 98.2 | 98.1 | 97.8 | 97.8 | 97.8 | 97.4 | 97.1 | 97 | 96.9 | 96.9 |
| 4 | 98.4 | 98.7 | 100 | *** | 99.3 | 99.7 | 99.6 | 99.5 | 98.2 | 98.1 | 97.8 | 97.8 | 97.8 | 97.4 | 97.1 | 97 | 96.9 | 96.9 |
| 5 | 98.9 | 98.9 | 98.9 | 98.9 | *** | 99.3 | 99.2 | 99.1 | 98.1 | 98.1 | 97.8 | 97.7 | 97.7 | 97.4 | 97.2 | 96.9 | 96.8 | 96.7 |
| 6 | 98.2 | 98.6 | 98.6 | 98.6 | 98.7 | *** | 99.5 | 99.7 | 98 | 98 | 97.7 | 97.7 | 97.6 | 97.4 | 97.1 | 96.9 | 96.8 | 96.6 |
| 7 | 98.1 | 98.1 | 98.7 | 98.7 | 98.7 | 98.9 | *** | 99.5 | *** | 97.9 | 97.6 | 97.5 | 97.5 | 97.2 | 97.1 | 96.8 | 96.8 | 96.8 |
| 8 | 97.7 | 98.2 | 98.7 | 98.7 | 98.4 | 99.3 | 98.6 | *** | 98 | 97.4 | 97.1 | 97.1 | 97.1 | 96.9 | 96.9 | 96.8 | 96.6 | 96.5 |
| 9 | 96 | 95.8 | 94.9 | 94.9 | 95.1 | 94.8 | 94.8 | 94.4 | *** | *** | *** | *** | *** | 99.1 | 98.7 | 98.4 | 98.3 | 98.4 |
| 10 | 97.3 | 96.6 | 95.7 | 95.7 | 95.6 | 95.5 | 95.5 | 95.1 | 93.9 | *** | 99.6 | 99.5 | 99.5 | 97 | 96.7 | 96.4 | 96.3 | 96.3 |
| 11 | 96.1 | 95.5 | 94.4 | 94.4 | 94.8 | 94.4 | 94.4 | 94 | 92.8 | 98.9 | *** | 99.9 | 99.6 | 96.7 | 96.4 | 96.1 | 96 | 96.1 |
| 12 | 96 | 95.3 | 94.6 | 94.6 | 94.8 | 94.2 | 94.4 | 94 | 92.6 | 98.7 | 99.8 | *** | 99.5 | 96.7 | 96.4 | 96.1 | 96 | 96 |
| 13 | 96.2 | 95.5 | 94.6 | 94.6 | 94.8 | 94.4 | 94.4 | 93.9 | 92.8 | 98.7 | 99.8 | 98.7 | *** | 96.6 | 96.3 | 96 | 95.9 | 98.7 |
| 14 | 94.1 | 93.5 | 92.6 | 92.6 | 92.8 | 92.4 | 92.8 | 94 | 97.3 | 92.9 | 92.5 | 92.5 | 92.5 | *** | *** | 98.1 | 98 | 97.8 |
| 15 | 93.7 | 93 | 92.1 | 92.1 | 92.6 | 92.2 | 92.6 | 91.9 | 96 | 92.1 | 91 | 91 | 91 | 95.8 | *** | *** | 98 | 97.4 |
| 16 | 93.7 | 93 | 92.1 | 92.1 | 92.1 | 91.9 | 92.2 | 91.5 | 95.8 | 91.3 | 90.3 | 90.3 | 90.3 | 95.3 | 95.3 | *** | 99.3 | 97.3 |
| 17 | 93.5 | 92.8 | 91.9 | 91.9 | 91.9 | 91.7 | 92.1 | 91.3 | 95.1 | 91.2 | 90.1 | 90.1 | 90.1 | 94.9 | 95.1 | 98 | *** | *** |
| 18 | 92.4 | 91.7 | 91.5 | 91.5 | 91.2 | 90.6 | 90.8 | 90.3 | 95.5 | 90.8 | 90.1 | 90.1 | 90.1 | 96.2 | 93.9 | 93.1 | 93.3 | *** |

% Amino acid identity

| Label | Strain (accession number) | Label | Strain (accession number) |
|---|---|---|---|
| 1 | A/duck/PA/2099/2012(H11N9)(KR870239) | 11 | A/shorebird/DE/351/2009(H11N9)(CY137916) |
| 2 | A/mallard/MN/Sg-00118/2007(H11N9)(CY078052) | 12 | A/turnstone/NJ/Ai09-1082/2009(H11N9)(CY146281) |
| 3 | A/goldeneye/IW/3192/2009(H11N9)(CY097068) | 13 | A/turnstone/Ilha_de_Canelas/AS1/2008(H11N9)(KF824506) |
| 4 | A/mallard/IA/3193/2009(H11N9)(CY097584) | 14 | A/teal/OH/467/2001(H11N9)(GU053360) |
| 5 | A/mallard/OH/2033/2009(H4N9)(CY097119) | 15 | A/knot/DE/650665/2002(H11N9)(CY144334) |
| 6 | A/mallard/WI/4203/2009(H11N9)(CY097424) | 16 | A/pintail/AB/22/1997(H2N9)(CY116777) |
| 7 | A/mallard/AR/Ai09-5663/2009(H11N9)(CY141011) | 17 | A/duck/WA/663/1997(H11N9)(EF599119) |
| 8 | A/teal/OH/12OS2138/2012(H10N9)(CY186865) | 18 | A/mallard/MD/439/2002(H2N9)(GQ257481) |
| 9 | A/mallard/AB/31/2001(H3N9)(CY004701) | | |
| 10 | A/turnstone/NJ/Sg-80561/2008(H11N9)(CY145689) | | |

Figure 44B

| Segment | Contig length (nt) | Average sequencing depth (min/max) | Comparison to the closest IBDV strains in Genbank | | | | |
|---|---|---|---|---|---|---|---|
| | | | Highest similarity strain (sequence ID) | Length (nt) | Identities | Gaps | Host |
| A | 3258 | 806±255(219/1028) | Infectious bursal disease virus segment A (U30818) | 3254 | 94% (3070/3259) | 12/3259 | Gallus |
| B | 2857 | 1307±450 (377/2623) | Infectious bursal disease virus segment B (AY918949) | 2827 | 95% (2698/2827) | 0/2807 | Edgar |
| Total | 6044 | | | 6013 | | 11 | |

| Strain | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | *** | 95.4 | 95.3 | 95.1 | 95 | 95 | 94.9 | 94.7 | 93.4 | 93.1 | 91.3 | 90.5 | 90.5 | 90.1 | 90.1 | 89.5 |
| 2 | 95.4 | *** | 99.5 | 95.6 | 98.3 | 98.1 | 98.6 | 95.1 | 95.9 | 95.8 | 92.4 | 90.1 | 90.3 | 90.1 | 89.6 | 89.6 |
| 3 | 95.3 | 99.5 | *** | 95.6 | 98.1 | 98.1 | 98.5 | 95 | 95.9 | 95.8 | 92.2 | 90.1 | 90.3 | 90.1 | 89.6 | 89.5 |
| 4 | 95.2 | 95.7 | 95.6 | *** | 95.3 | 95.3 | 95.3 | 94.7 | 95.4 | 95.7 | 92.9 | 90.9 | 90.8 | 90.8 | 90.1 | 90 |
| 5 | 95 | 98.3 | 98.1 | 95.3 | *** | 100 | 98.3 | 94.6 | 95.4 | 95.6 | 92.9 | 90.3 | 90 | 89.7 | 89.3 | 89.2 |
| 6 | 95 | 98.2 | 98.1 | 95.3 | 100 | *** | 98.3 | 94.8 | 95.4 | 95.6 | 92.9 | 90.3 | 90.2 | 89.9 | 89.3 | 89.5 |
| 7 | 94.9 | 98.6 | 98.5 | 95.4 | 98.3 | 98.3 | *** | 94.8 | 95.4 | 96.7 | 92.5 | 90.3 | 91.1 | 90.9 | 89.6 | 89.5 |
| 8 | 94.7 | 95.1 | 95 | 95.3 | 94.7 | 94.6 | 94.8 | *** | 93.1 | 92.8 | 90.7 | 89.6 | 89.5 | 89.4 | 88.7 | 88.6 |
| 9 | 93.4 | 95.9 | 95.9 | 93.7 | 95.4 | 95.4 | 95.6 | 93.1 | *** | 93.6 | 90.9 | 89.7 | 89.4 | 89.4 | 88.7 | 88.1 |
| 10 | 93.1 | 95.8 | 95.8 | 93.8 | 95.7 | 95.6 | 96.7 | 92.8 | 93.6 | *** | 90.5 | 89.7 | 89.5 | 88.1 | 88 | 88.1 |
| 11 | 91.3 | 92.4 | 92.2 | 91.5 | 92.9 | 92.9 | 92.5 | 90.7 | 90.9 | 90.5 | *** | 89.5 | 89.3 | 88.1 | 88 | 88.1 |
| 12 | 90.5 | 90.2 | 90.1 | 90.9 | 90.1 | 90.1 | 90.3 | 90.3 | 90.1 | 89.7 | 89.5 | *** | 93.1 | 93 | 92.5 | 92.7 |
| 13 | 90.5 | 90.3 | 90.3 | 90.8 | 90.1 | 90.1 | 90.3 | 90.3 | 90.1 | 89.4 | 89.5 | 93.1 | *** | 99.3 | 97.2 | 91.7 |
| 14 | 90.1 | 90.1 | 90.1 | 90.6 | 89.7 | 89.9 | 90.3 | 90.3 | 90.1 | 88.7 | 88.1 | 93 | 99.3 | *** | 96.9 | 91.5 |
| 15 | 90.1 | 89.6 | 89.6 | 90.1 | 89.4 | 89.3 | 89.6 | 90.5 | 88.7 | 88.7 | 88 | 92.5 | 97.2 | 96.9 | *** | 93.2 |
| 16 | 89.5 | 89.6 | 89.5 | 90 | 89.2 | 89.5 | 89.6 | 89.5 | 88.6 | 88.1 | 88.1 | 92.6 | 91.7 | 91.5 | 93.2 | *** |

% Nucleotide identity / % Amino acid identity

| Label | Strain (accession number) | Label | Strain (accession number) |
|---|---|---|---|
| 1 | 00924(2012)(KP642112) | 11 | HN04(2013)(KC109815) |
| 2 | Edgar(2007)(AY918947) | 12 | HLJ-7(GQ452269) |
| 3 | Lukert(2007)(AY918947) | 13 | SKS3(2014)(KJ198845) |
| 4 | 23/82(2001)(AF362774) | 14 | HLJ-4(2010)(GQ449689) |
| 5 | GA-1(2008)(EU162094) | 15 | ZZ-11(2012)(JX682712) |
| 6 | ViBursa(2008)(EU162092) | 16 | QL(2012)(JX682710) |
| 7 | A-BH83(2011)(JF811921) | | |
| 8 | OH(2007)(U30819) | | |
| 9 | MG1(2013)(JN982246) | | |
| 10 | GX-NNZ-11(2013)(KJ134484) | | |

Figure 47B

| Ultrafiltration Devices | Pore size (nm) | Thickness | Operating pressure (kPa) | Flux (m/s)[a] | Normalized resistance (/m)[b] | Permeability (m²)[c] | Porosity | Tunable range (nm) | Reference |
|---|---|---|---|---|---|---|---|---|---|
| Hydrophilized PVDF (Millipore Viresolve 180) | 12-18 | 150 µm | 103 | 1.4-1.5×10⁻⁴ | 6.9-7.4×10¹¹ | 2.1×10⁻¹⁶ | - | - | (65, 66) |
| Hydrophilized PVDF (Pall DV20) | 20 | 40 µm | 155 | 2.1×10⁻⁷ | 7.5×10¹⁴ | 5.4×10⁻²⁰ | - | 20, 50 | (65) |
| Nanoporous block co-polymer | 15 | 80 nm | 10 | 1.1-1.4×10⁻⁵ | 7.2-9.0×10¹¹ | 1.0×10⁻¹⁸ | 20% | 10-40 | (67) |
| Anodized aluminum oxide membrane | 16 | - | 98 | 1.3×10⁻⁶ | 7.5×10¹³ | - | - | 15-401 | (68-72) |
|  | 20 | 60 µm | 150 | 4.4×10⁻⁵ | 3.4×10¹¹ | 1.8×10⁻¹⁶ | 25-50% |  |  |
| Track etched polycarbonate (Nuclepore) | 15 | 6.5 µm | 10 / 196 | 0.8-1.1×10⁻⁷ / 1.8×10⁻⁶ | 0.9-1.3×10¹⁴ | 6.1×10⁻²⁰ | 2% | 15-8,000 | (67) / (72) |
| CNT-STEM | 25 / 95 | 100 µm | 0.69 | 1.2×10⁻⁴ / 7.7×10⁻⁴ | 5.9×10⁹ / 9.0×10⁸ | 1.7×10⁻¹⁴ / 1.1×10⁻¹³ | 78% / 92% | 17-325 | This study | a: Flux (m/s) $J_v$ is either taken directly from references or calculated by using volumetric flow rate Q and cross-sectional area A as $J_v = \frac{Q}{A}$ b: Normalized resistance $R_m$ is calculated from flux $J_v$, viscosity $\mu$, and operation pressure $\Delta P$ using $R_m = \frac{-\Delta P}{\mu J_v}$ (73)

c: Permeability $\kappa$ can be calculated from normalized resistance $R_m$ and membrane thickness using $\kappa = \frac{L}{R_m}$

Figure 48

| | Steps | Yield | Failure mode | Counts (failure) |
|---|---|---|---|---|
| Fabrication | Iron patterning/dicing | 100% (228/228) | | 0 |
| | N-MWCNT synthesis | 100% (228/228) | | 0 |
| | PDMS bonding | 93% (212/228) | Misalignment | 16 |
| | Assembly | 97.2% (206/212) | CNT crash by mishandling | 6 |
| Testing | Device quality check | 85.1% (175/206) | Leakage | 31 |
| | Virus filtration | 100% (175/175) | | 0 |
| | RNA extraction | 100% (175/175) | | 0 |
| Total | | 76.8% (175/228) | | 53 |

| Sample and dilutions | Sample prep method | |
|---|---|---|
| | USDA protocol | CNT-STEM |
| Ct Value | | |
| Healthy control | 0 | 0 |
| Positive samples 1X | 27.3 | 25.81 |
| Positive samples 1:10 | 32.87 | 25.95 |
| Positive samples 1:100 | 37.21 | 30.22 |

Figure 50B

| Virus titer (pfu/mL) | Before enrichment | | After enrichment | | Enrichment factor (fold) |
|---|---|---|---|---|---|
| | ct | copies | ct | copies | |
| $10^7$ | 26.7252 | 5.51E+03 | | | |
| $10^6$ | 29.6412 | 654.791 | | | |
| $10^5$ | 34.3402 | 21.1276 | 25.5318 | 1.32E+04 | 625 |
| $10^4$ | 36.1114 | 5.79101 | | | |
| $10^3$ | 36.7611 | 3.60209 | 28.8282 | 1.19E+03 | 330 |

SIZABLE TUNABLE ENRICHMENT PLATFORM FOR CAPTURING NANO PARTICLES IN A FLUID

CROSS-REFERENCE TO RELATED APPLICATIONS

This application is a divisional application to U.S. application Ser. No. 16/784,507 filed on Feb. 7, 2020, which is a divisional application to U.S. application Ser. No. 15/213,128 filed on Jul. 18, 2016, which claims priority to U.S. Provisional Patent Application No. 62/193,876, filed Jul. 17, 2015, the contents of each is incorporated by reference herein in its entirety.

STATEMENT REGARDING FEDERALLY SPONSORED RESEARCH OR DEVELOPMENT

This invention was made with government support under Grant No. CA174508 and TR000127 awarded by the National Institutes of Health, under Grant No. FA9550-12-1-0035 awarded by the United States Air Force and under Hatch Act Project No. PEN01607 awarded by the United States Department of Agriculture. The Government has certain rights in the invention.

BACKGROUND OF THE INVENTION

The traumatic impact of viral infectious diseases was witnessed in the 1918 influenza pandemic, the ongoing HIV/AIDS pandemic, the most recent Ebola outbreak (Fauci A. S. et al., New Engl J Med, 2012, 366:454-461), and more. Rapid isolation, identification, and characterization of viruses from field samples are critical in the prevention of epidemics (Pennington H., Nat Rev Micro, 2004, 2:259-262). Small footprint lab-on-a-chip systems promise to rapidly analyze samples of small quantity with high sensitivity at points of care (Whitesides G. M., Nature, 2006, 422:368-373). Although many advanced virus detection methods have been reported, there has yet to be a high efficiency sample preparation system (Ritzi-Lehnert M., Expert Rev Mol Diagn, 2012, 12:189-206; Sin M. L. Y. et al., Expert Rev Mol Diagn, 2014, 14:225-244). Most previous work employed antibodies or ligands to capture known nanoscale target like viruses (Stern et al., Nature, 2007, 445:519). Existing virus sample preparation systems utilizing, e.g. immune-based capture, which requires foreknowledge of virus strain or membrane-based filtration, suffers from low efficiency and capacity due to non-uniformity of pore size and low porosity, as well as a lack of downstream virus analysis integration and lowers accessibility to the public. Label-free methods will be highly desirable for unknown viruses. In addition, it is difficult to release the captured NPs for further analysis.

There is a need for an improved method of label-free capture for small particles like viruses. The present invention meets this need.

SUMMARY OF THE INVENTION

The invention provides enrichment platform devices for size-based capture of particles in solution. The enrichment platform device is useful for label-free capture of any particle. The invention relates to enrichment platform devices using nanowires and vertically aligned carbon nanotubes. The invention provides methods for making the enrichment platform devices. The invention provides methods for using the enrichment platform devices for filtering particles, capturing particles, concentrating particles, and releasing viable particles.

In one aspect, the invention relates to an enrichment platform device for size-based, label-free capture of particles in sample solution, the device comprising: a substrate; vertically-aligned carbon nanotubes arrays (VACNT); and a cover having at least one inlet and at least one outlet; wherein the VACNT is attached to the substrate, the cover bonds to the substrate to seal the VACNT within the cover, and sample solution enters via the at least one inlet, passes over the VACNT, and exits via the at least one outlet, whereupon particles in the sample solution are captured by the gaps between the VACNT based on size.

In one embodiment, the substrate comprises material selected from the group consisting of: silicon, glass, sapphire, metals, and polymers. In one embodiment, the cover comprises material selected from the group consisting of: plastics, metals, glass, sapphire, polymers, and polydimethylsiloxane (PDMS). In one embodiment, the cover is removable.

In one embodiment, the VACNT comprise single-walled CNT, double-walled CNT, multi-walled CNT, and combinations thereof. In one embodiment, the VACNT is nitrogen-doped VACNT, boron-doped VACNT, silicon-doped VACNT, aluminum-doped VACNT, phosphorus-doped VACNT, lithium-doped VACNT, and combinations thereof. In one embodiment, the VACNT are separated by a gap size between 1 nm and 500 nm.

In one embodiment, the device is a microfluidic device. In one embodiment, the device is a handheld device.

In another aspect, the present invention relates to an enrichment platform device for size-based, label-free capture of particles in sample solution, the device comprising: a substrate comprising a plurality of channels; a cover having at least one inlet and at least one outlet; and a plurality of nanowires; wherein the plurality of nanowires are attached to the substrate within the channels, the cover seals the plurality of channels, and sample solution enters via the at least one inlet, passes through the plurality of channels, and exits via the at least one outlet, whereupon particles in the sample solution are captured by the gaps between the plurality of nanowires based on size.

In one embodiment, the substrate comprises material selected from the group consisting of: silicon, glass, sapphire, metals, and polymers. In one embodiment, the cover comprises material selected from the group consisting of: plastics, metals, glass, sapphire, polymers, and polydimethylsiloxane (PDMS). In one embodiment, the cover is removable.

In one embodiment, the nanowires comprise materials selected from the group consisting of: silicon, zinc, zinc oxide, and nickel. In one embodiment, each nanowire is separated by a gap size between 1 nm and 500 nm.

In one embodiment, the device is a microfluidic device. In one embodiment, the device is a handheld device.

In another aspect, the present invention relates to a method of making an enrichment platform device comprising VACNT, the method comprising: depositing a metal catalyst thin film on a substrate by e-beam evaporation and lift-off process; patterning the metal catalyst thin film using lithography; depositing CNT precursor material on the metal catalyst thin film using chemical vapor deposition (CVD) to create VACNT; and bonding a cover to the substrate to encase the VACNT.

In one embodiment, the metal catalyst thin film is an iron-catalyst thin film, a nickel-catalyst thin film, or a cobalt-catalyst thin film. In one embodiment, the metal catalyst thin film thickness is adjusted to tune gap size, diameter, and density of the VACNT. In one embodiment, increasing the metal catalyst thin film thickness increases the VACNT gap size. In one embodiment, the gap size is tuned between 1 nm and 500 nm. In one embodiment, increasing the metal catalyst thin film thickness increases the VACNT diameter. In one embodiment, increasing the metal catalyst thin film thickness decreases the VACNT density.

In one embodiment, the precursor comprises doping material. In one embodiment, the doping material is selected from the group consisting of: nitrogen, boron, silicon, aluminum, phosphorus, and lithium.

In another aspect, the present invention relates to a method of making an enrichment platform device comprising porous silicon nanowires (PSNWs), the method comprising: depositing a thin photoresist layer on a silicon substrate; patterning the thin photoresist layer by removing photoresist using lithography; etching a channel in the substrate where photoresist is absent; depositing a thicker layer of photoresist on the existing layer of photoresist; depositing silver nanoparticles (SNP) within the etched channel; reacting with the SNP as a catalyst to perform silicon etching to form PSNWs; removing the photoresist and SNP; and bonding a cover to the substrate to encase the PSNWs.

In one embodiment, the etching is deep reactive-ion etching (DRIE), metal assisted silicon etching, or wet etching. In one embodiment, the gap size of the PSNWs is tuned by adjusting SNP deposition time. In one embodiment, increasing SNP deposition time increases PSNW gap size. In one embodiment, the gap size is tuned between 1 nm and 500 nm.

In another aspect, the present invention relates to a method of filtering particles of a specific size out of a solution, the method comprising: fabricating an enrichment platform device comprising a gap size matching the size of the particle to be filtered; and passing the solution through the filter.

In another aspect, the present invention relates to a method of capturing particles of a specific size out of a solution for analysis, the method comprising: fabricating an enrichment platform device comprising a gap size matching the size of the particle to be filtered; passing the solution through the filter; and analyzing the captured particles in the enrichment platform device.

In another aspect, the present invention relates to a method of capturing viable particles of a specific size out of a solution and releasing the same viable particles for analysis, the method comprising: fabricating an enrichment platform device comprising a gap size matching the size of the particle to be filtered; passing the solution through the filter; removing the enrichment platform device cover; releasing the captured viable particles from the enrichment platform device; and analyzing the released viable particles.

In one embodiment, the particles are released by scratching the device surface. In one embodiment, the particles are released by degrading the device nanostructures. In one embodiment, the solution is derived from a patient. In one embodiment, the captured particles are used to diagnose the patient as being host to the captured particles. In one embodiment, a patient being diagnosed as hosting the captured particles is indicative of having a disease.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts a device wherein the VACNT are bonded to substrate on the bottom and to cover on the top. FIG. 1B depicts a device wherein the VACNT are freestanding and are bonded to substrate only on the bottom.

FIG. 2A: size of various biological molecules in the micro and nano scale. FIG. 2B: illustrations of pSiNWs forest based microfluidic device showing the overall microfluidic design in 3D, the location of the pSiNWs forests (top inset, cross-sectional view), and nanoparticles captured inside the pSiNWs forest (bottom inset). FIG. 2C: photo of a prototype device.

FIG. 3A: Sketch of synthesizing pSiNWs showing larger SNPs defining the inter-wire spacing and tiny SNPs generating porous structures on individual silicon nanowire. Black solid arrows indicate reactant fluoride ions coming to the surface. Red dash lines indicate product silicon hexafluoriode anions leaving the surface into the bulk. FIG. 3B: Scanning Electron Microscope (SEM) of SNPs and channel bottom (bar: 500 nm, insert bar: 200 nm). FIG. 3C: SEM images of pSiNWs on channel bottom (bar: 500 nm, insert bar: 200 nm). FIG. 3D: SEM images of pSiNWs on side wall (bar: 2 μm). FIG. 3E: SEM images of cross-section view of pSiNWs (bar: 2 μm, two inserts' bar: 500 nm). FIG. 3F: Sizes of SNPs and inter-wire spacing of pSiNWs forests versus the silver nanoparticle deposition time. FIG. 3G, FIG. 3H: Distribution of the inter-wire spacing of pSiNWs with silver nanoparticle deposition time of 45 s (FIG. 3G) and 60 s (FIG. 3H), respectively.

FIG. 6A: Schematic of the channel. FIG. 6B: Velocity field along the channel (x direction, $V_x$). FIG. 6C: Velocity field in the horizontal plane (y direction, $V_y$). FIG. 6D: Velocity field in the vertical plane (z direction, $V_z$).

FIG. 7A: Schematic of the channel. FIG. 7B: Velocity field along the channel (x direction, $V_x$). FIG. 7C: Velocity field in the horizontal plane (y direction, $V_y$). FIG. 7D: Velocity field in the vertical plane (z direction, $V_z$).

FIG. 8A: Schematic of the channel. FIG. 8B: Velocity field along the channel (x direction, $V_x$). FIG. 8C: Velocity field in the horizontal plane (y direction, $V_y$). FIG. 8D: Velocity field in the vertical plane (z direction, $V_z$).

Wall lift force: $F_L = f(\beta) \rho_f v_m^2 a^4 / D_H^2$

Dean force: $F_D = 1.08 \times 10^{-3} \pi \mu D e^{1.63} a$, $De = Re \sqrt{\dfrac{D_H}{2R}}$ Stokes drag: $F_s = 6\pi \mu a v$ Here, $f(\beta)$ is the wall lift coefficient, $\rho_f$ is the density of the fluid, $v_m$ is fluid velocity in z direction, a is the nanoparticle radius, $D_H$ is the hydraulic diameter of the channel, µ is the dynamic viscosity of the fluid, v is the velocity in $\beta$ direction, De is Dean number, Re is Reynolds number, R is the curvature radius of the channel. In the device, the velocity of the fluid is 0.011 m/s. The height of the channel was 20 µm. The width of the channel was 100 µm. The curvature radius was 100 µm. The nanoparticle radius was about 50 nm, Under these conditions, the wall lift force was about $10^{-19}$ N, and the Dean force was about $7.7 \times 10^{-15}$ N. So the Dean force was larger than the wall lift force by 3 orders of magnitude. (Ho, B. P. et al., Journal of Fluid Mechanics 1974, 65:365-400; Asmolov, E. S., Journal of Fluid Mechanics 1999, 381:63-87; Matas, J.-P. et al., Journal of Fluid Mechanics 2004, 515:171-195).

Figures 10A, 10B, 10C, 10D:
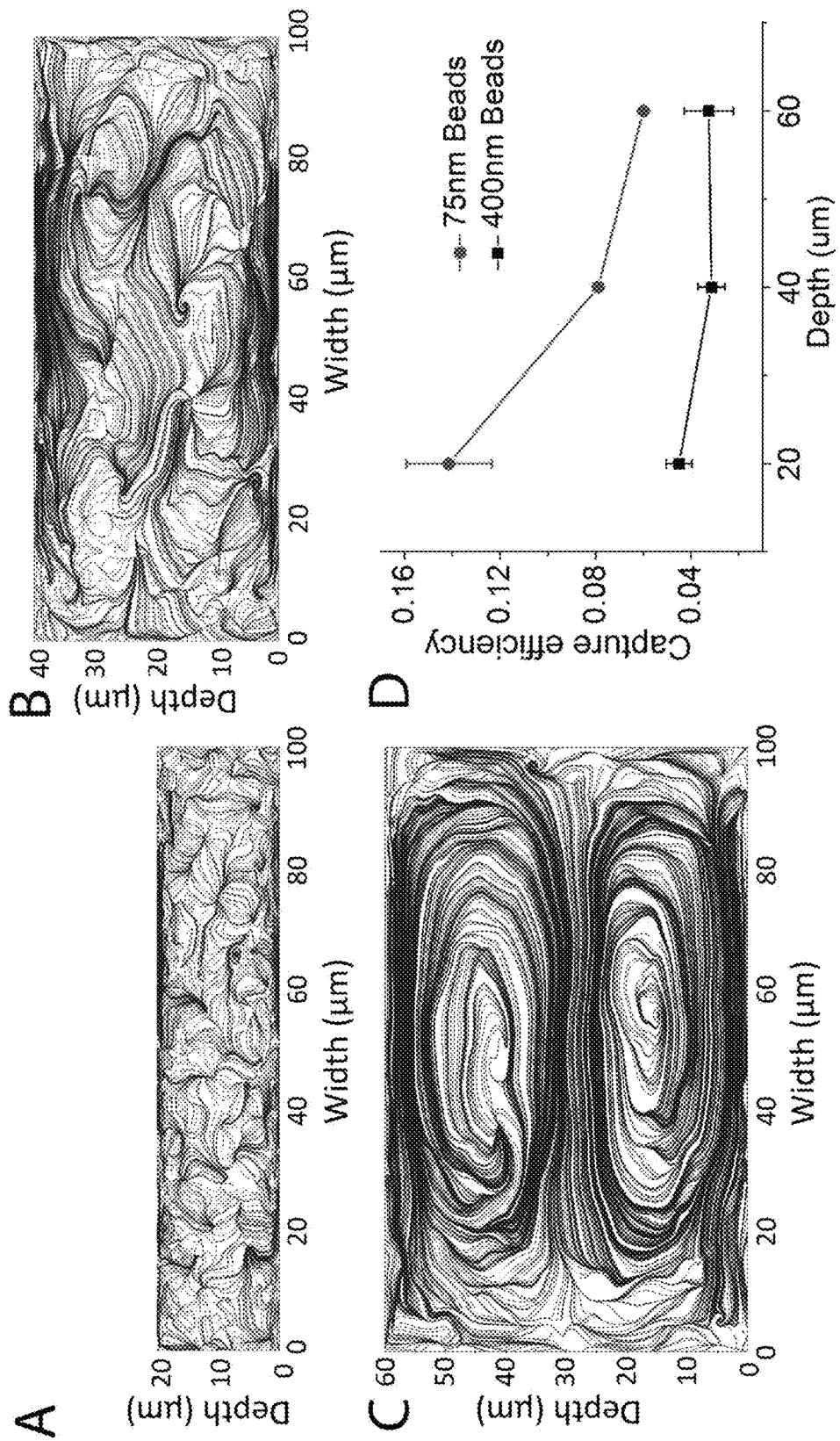

FIG. 10A through FIG. 10I depict the capture of nanoscale particles inside the pSiNWs microfluidic devices with the effect of the Dean flow. FIG. 10A through FIG. 10C: FEM simulations showing velocity field on the cross-sectional planes of meandering flow channels with channel depths of 20, 40 and 60 µm, respectively. 0 and 100 µm point the outer and inner rim of channel, respectively. FIG. 10D: Capture efficiency of 75 nm and 400 nm nanobeads in channels with 20, 40 and 60 µm height, respectively. FIG. 10E: Capture of 75 nm green nanobeads showing top views of the pSiNWs flow channels before, during, and after injecting nanobeads (bar: 200 µm); FIG. 10F: Capture of 400 nm blue nanobeads showing top views of the pSiNWs flow channels before, during and after injecting nanobeads (bar: 200 µm); FIG. 10G: SEM image of captured 75 nm nanobeads (bar: 150 nm). FIG. 10H: Capture efficiency of 75 nm and 400 nm nanobeads under different flow rates. FIG. 10I: Capture efficiency of 75 nm and 400 nm nanobeads versus number of run times of the same sample in the same device.

Figures 11A, 11B, 11C:
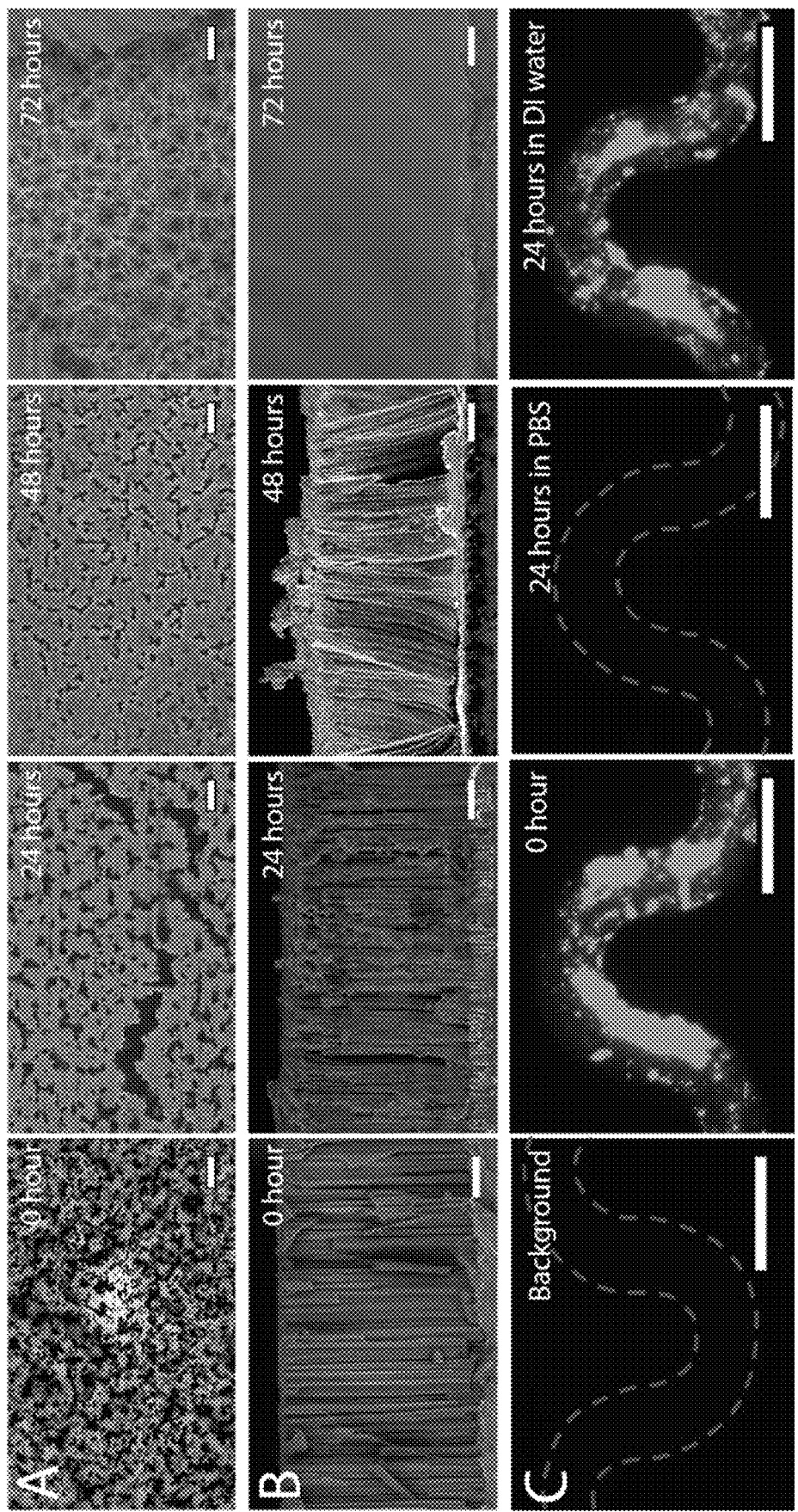

FIG. 11A through FIG. 11C depict the degradation of pSiNWs and release of captured nanobeads. FIG. 11A: SEM images of pSiNWs s from the top view after soaking in PBS for 0, 24, 48 and 72 hours (bar: 1 µm). FIG. 11B: SEM images of pSiNWs from the side view after soaking in PBS for 0, 24, 48 and 72 hours (bar: 2 µm). FIG. 11C: Releasing nanobeads by degrading pSiNWs forests for 24 hours in PBS (bar: 200 µm).

FIG. 12A through FIG. 12E depict the capture of viruses inside the pSiNWs microfluidic devices. FIG. 12A: Control group: without injecting viruses (bar: 200 µm). FIG. 12B: Capture of green immunofluorescent stained avian influenza virus (bar: 200 µm). FIG. 12C: SEM image of a captured virus (scale bar: 150 nm). FIG. 12D: Virus fluorescence intensity measured under different flow rates. FIG. 12E: RT-qPCR of inflow sample and outflow samples to calculate capture efficiency.

FIG. 13 is a table listing the virus capture efficiency of the device.

Figures 14A, 14B, 14C:
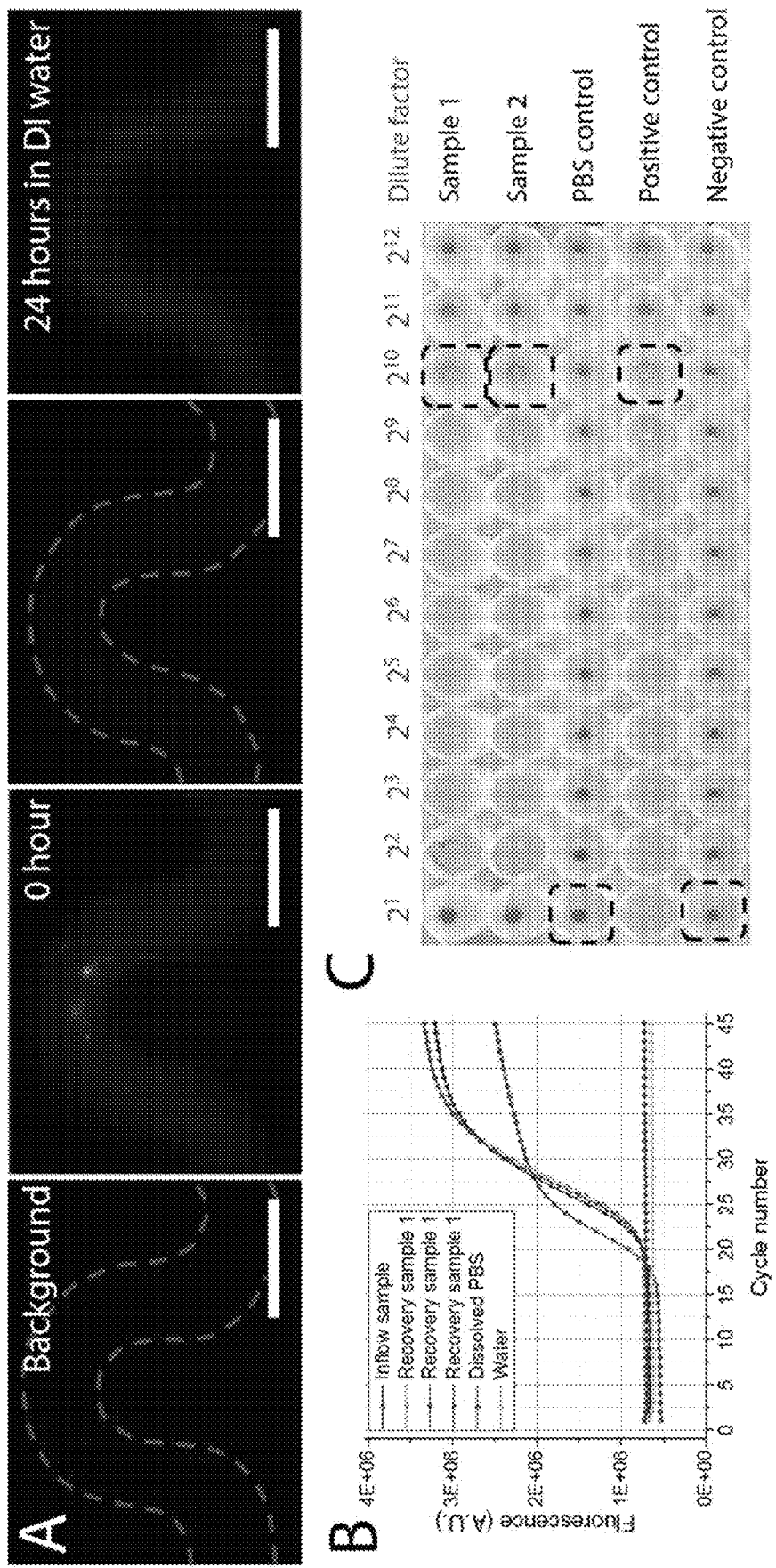

FIG. 14A through FIG. 14C depict the results of releasing and propagation of released virus. FIG. 14A: Releasing virus by degrading pSiNWs forests for 24 hours in PBS (bar: 200 µm). FIG. 14B: RT-qPCR of inflow sample and recovery samples to calculate recovery efficiency. Dissolved PBS: pSiNWs degradation solution in PBS without viruses. FIG. 14C: HA test on samples after released virus and propagation in embryonated chicken eggs. PBS control: pSiNWs degradation solution in PBS without viruses; Positive control: virus solution with a titer $1:2^9$; Negative control: DI water.

FIG. 15A through FIG. 15C depict the collection of released virus by antibody conjugated magnetic beads. FIG. 15A: Sketch of detecting released viruses by magnetic beads (Fluorescence of streptavidin is red). FIG. 15B: Released virus. FIG. 15C: Control group. Viruses were captured by H5 antibody conjugated magnetic beads and then stained with red fluorescence labeled streptavidin conjugated to biotin labeled H5 antibody. The red fluorescence in the released virus solution was much stronger than that of the control group, indicating there were many viruses released in gap size. (FIG. 19B) Capture efficiency of 95 nm gap size device characterized by fluorescent nanospheres. (FIG. 19C) Top-viewed fluorescence images of herringbone structure after applied a mixture of particles with diameters of 20 nm (red), 100 nm (green), and 1000 nm (blue).

Figures 20A, 20B, 20C, 20D:
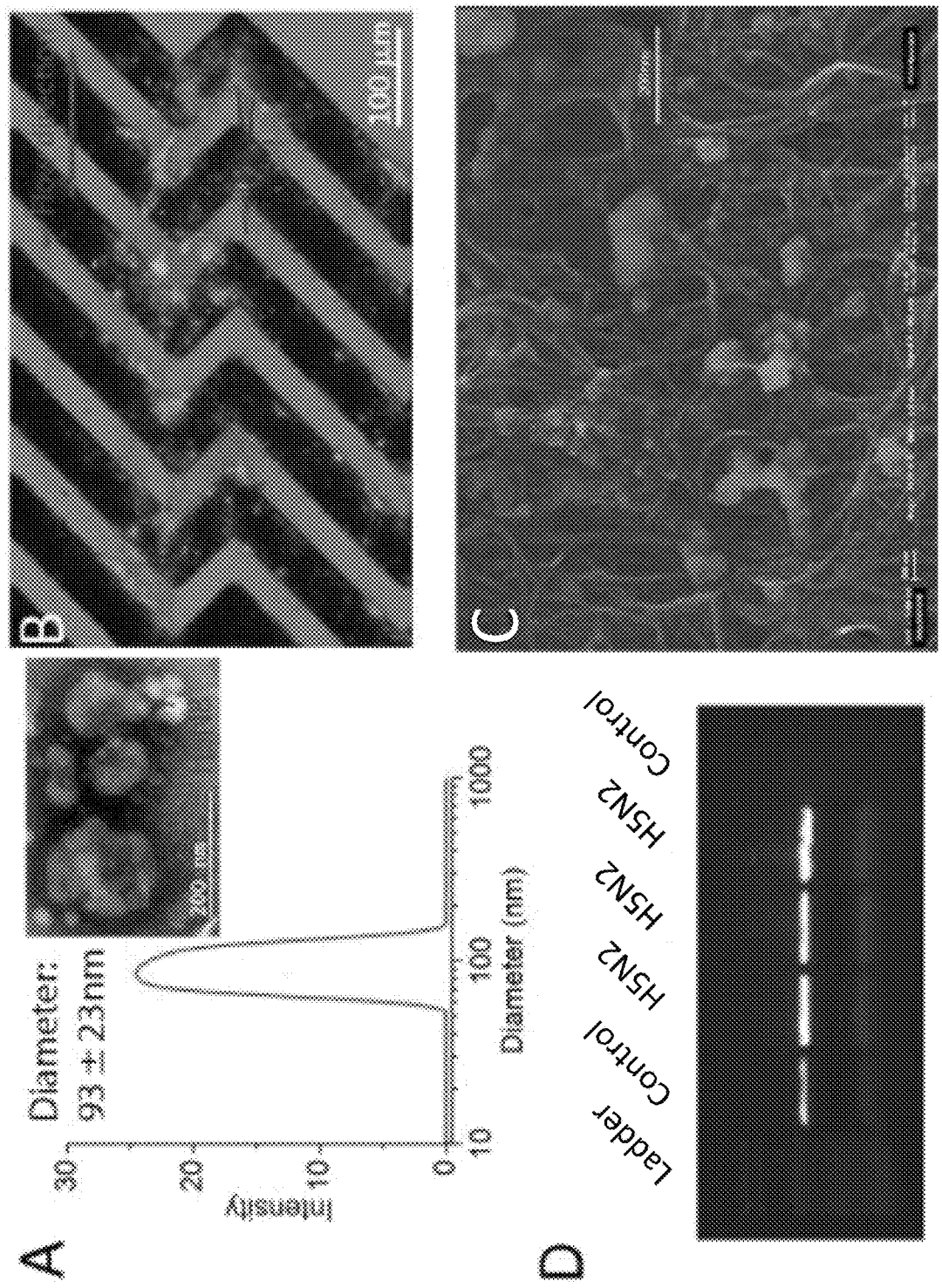

FIG. 20, comprising FIG. 20A through FIG. 20D, depicts the results of experiments demonstrating the capture and on-chip detection of Avian influenza virus H5N2 from a swab sample. (FIG. 20A) Histogram of H5N2 diameter with a TEM image (inset). (FIG. 20B) On-chip indirect immunofluorescence detection. (FIG. 20C) SEM images of H5N2 trapped inside the herringbone structure. (FIG. 20D) DNA gel electrophoresis for genetic analysis after on-chip lysis.

Figure 21:
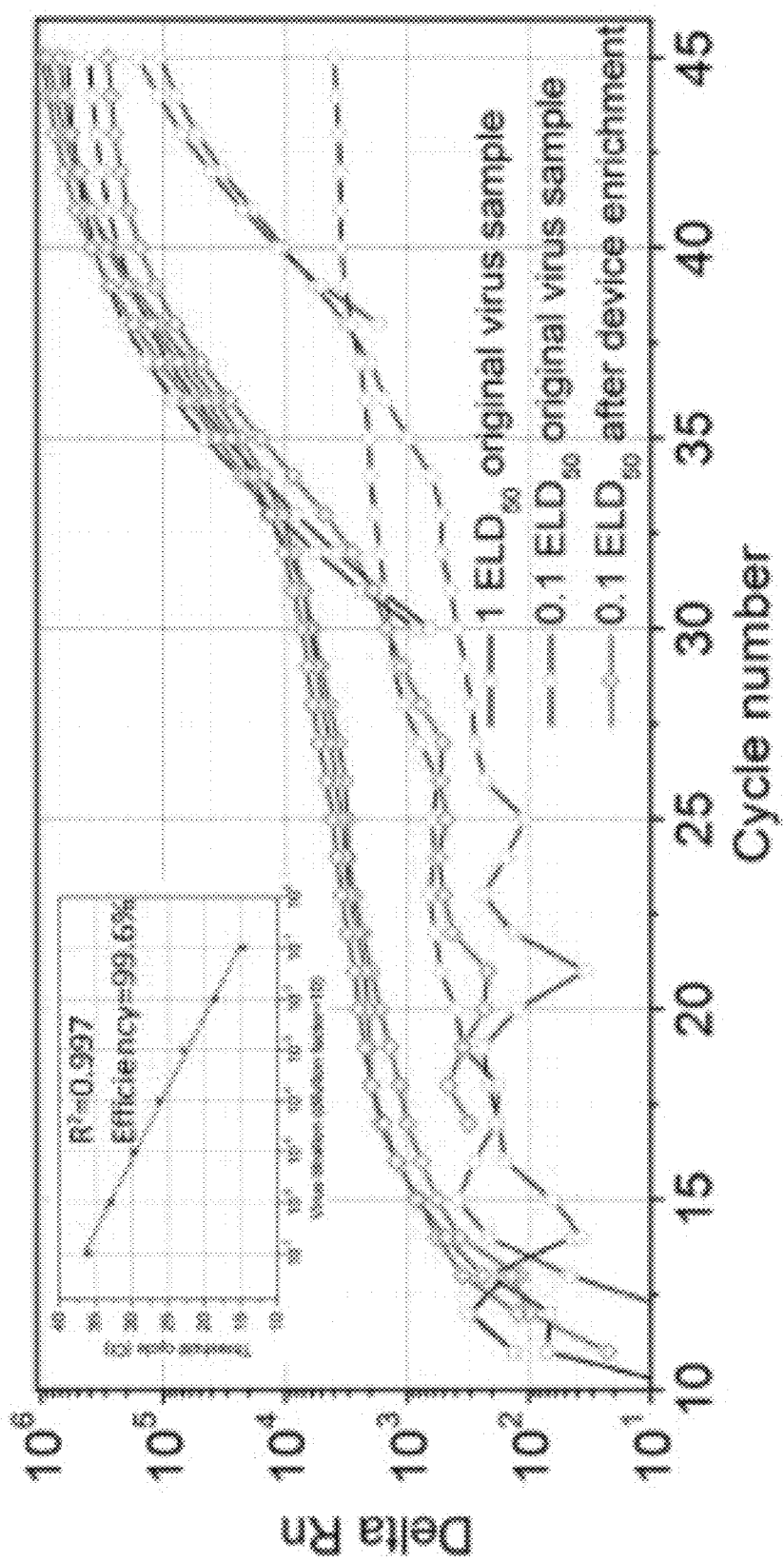

FIG. 21 depicts RT-qPCR demonstration of H5N2 enrichment and improvement of detection limit from 1 $ELD_{50}$ to 0.1 $ELD_{50}$.

Figures 22A, 22B:
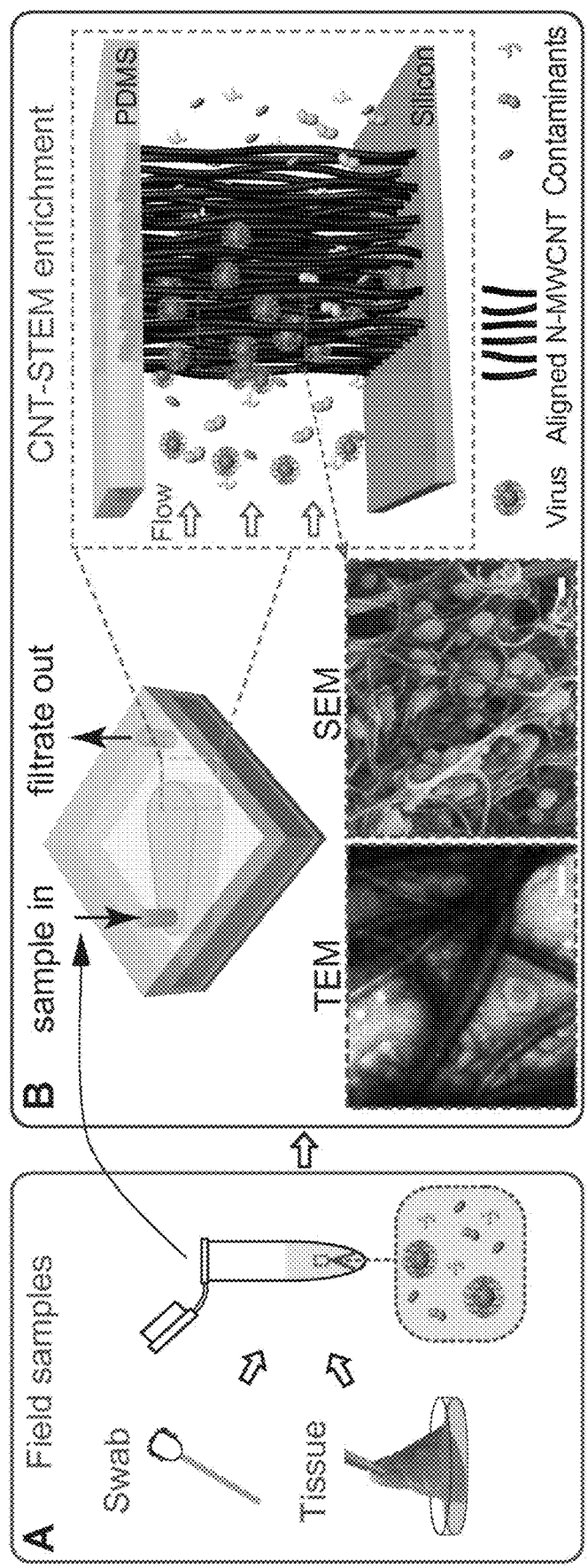

FIG. 22A and FIG. 22B depict the working principle of virus enrichment and concentration from field samples. (FIG. 22A) A field sample containing viruses (purple spheres) is collected by a cotton swab or as a tissue sample. (FIG. 22B) The supernatant of the field sample flows through the CNT-STEM and the viruses are enriched within the device. Inset (right): illustration of size-based virus enrichment by the aligned N-MWCNTs. Inset (bottom right): SEM image (scale bar, 100 nm) of the H5N2 AIV virions trapped inside the aligned N-MWCNTs. Inset (bottom left): dark field TEM image (scale bar, 100 nm) of enriched H5N2 AIV after the aligned N-MWCNTs structures were retrieved from the CNT-STEM.

Figures 23A, 23B:
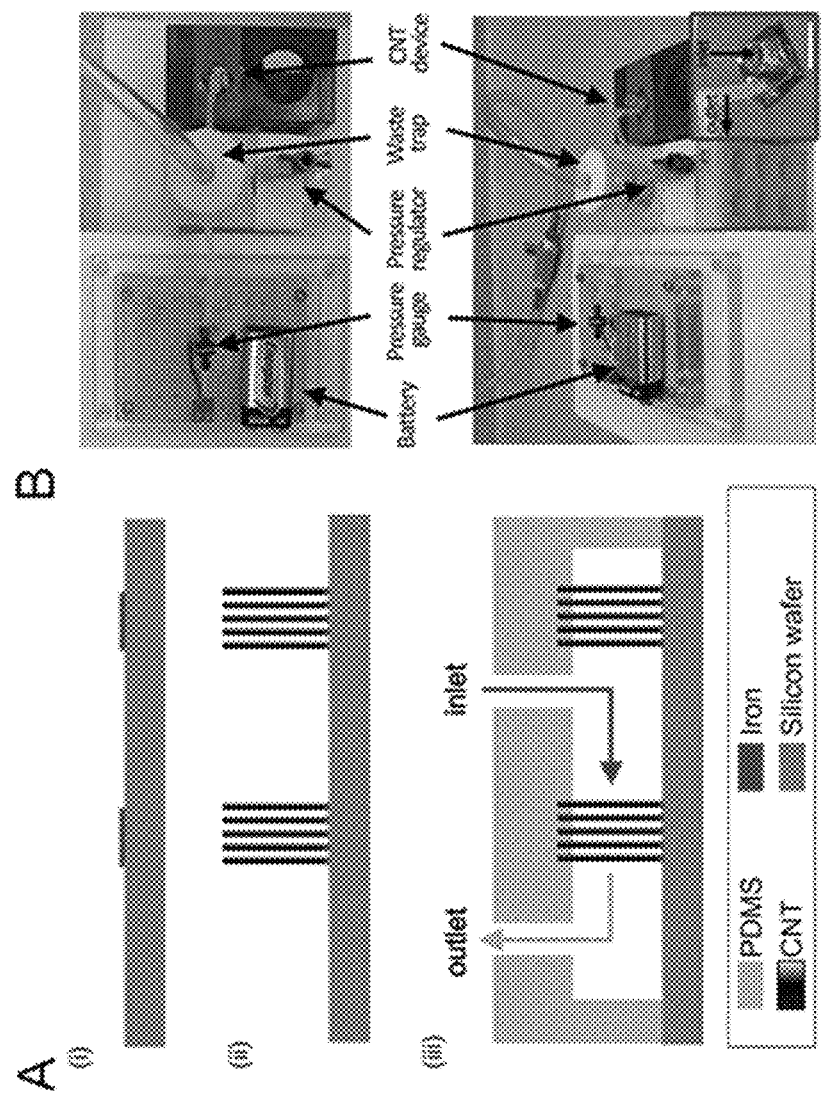

FIG. 23A and FIG. 23B depict the fabrication process and the testing setup of the CNT-STEM. (FIG. 23A) Fabrication process of CNT-STEM. (i) Iron catalyst thin film was deposited on a prime silicon wafer and patterned by a lift-off process. (ii) The aligned CNT was selectively synthesized on patterned silicon surface during AACVD. (iii) CNT-STEM was formed by bonding a PDMS chamber with fluidic access to silicon substrate. Arrows label sample flow direction from the inlet to the outlet. (FIG. 23B) Top and side view of the testing setup. The virus-containing sample was first filtered through a membrane filter of 0.2 μm pore size (not shown here), then loaded into the sample reservoir at the inlet and processed through CNT-STEM via a vacuum source connected through a waste trap at the outlet. The vacuum pressure was measured by a miniature pressure sensor and regulated by a precision mechanical regulator. Inset shows the CNT-STEM device, scale bar: 1 cm.

Figure 24:
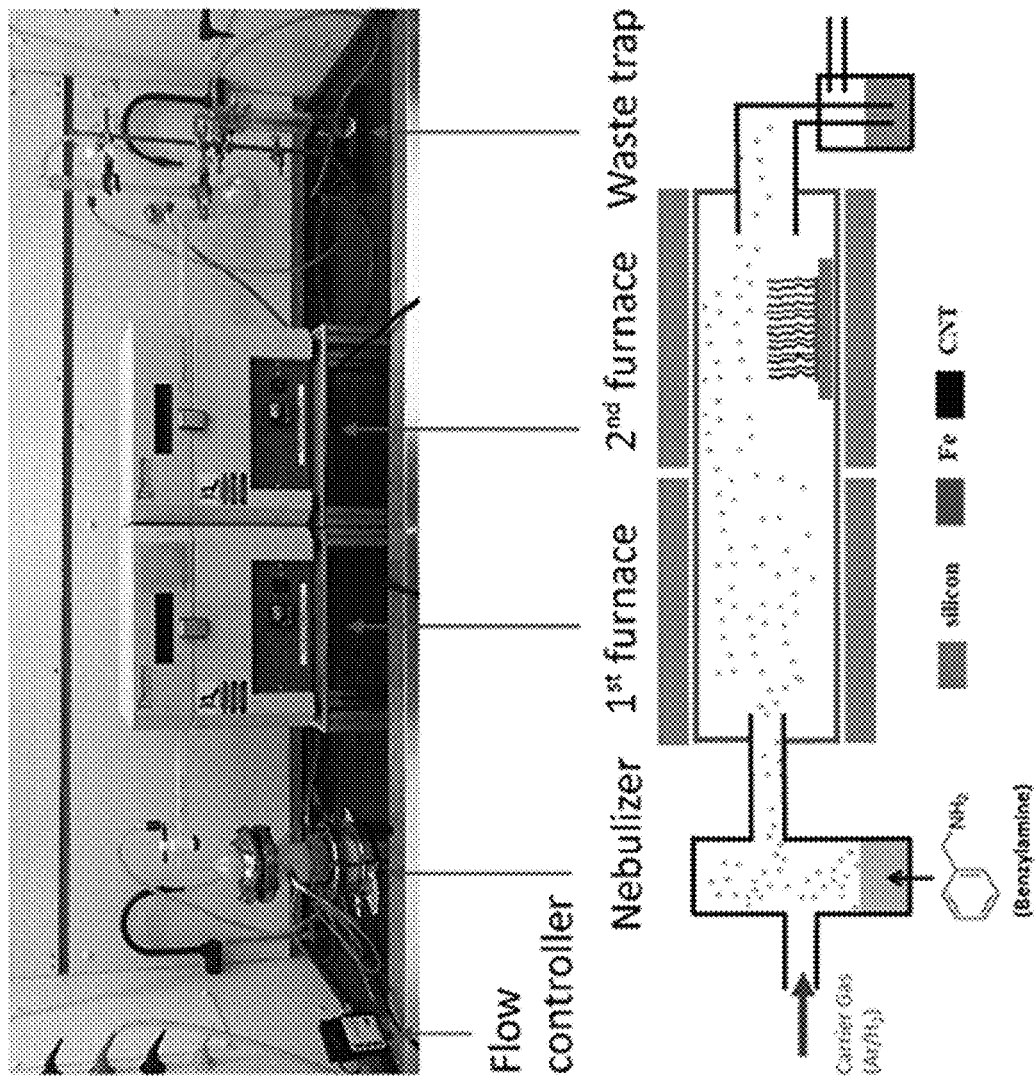

FIG. 24 depicts aerosol assisted chemical vapor deposition (AACVD) for nitrogen-doped carbon nanotube (N-MWCNT) synthesis.

Figure 25:
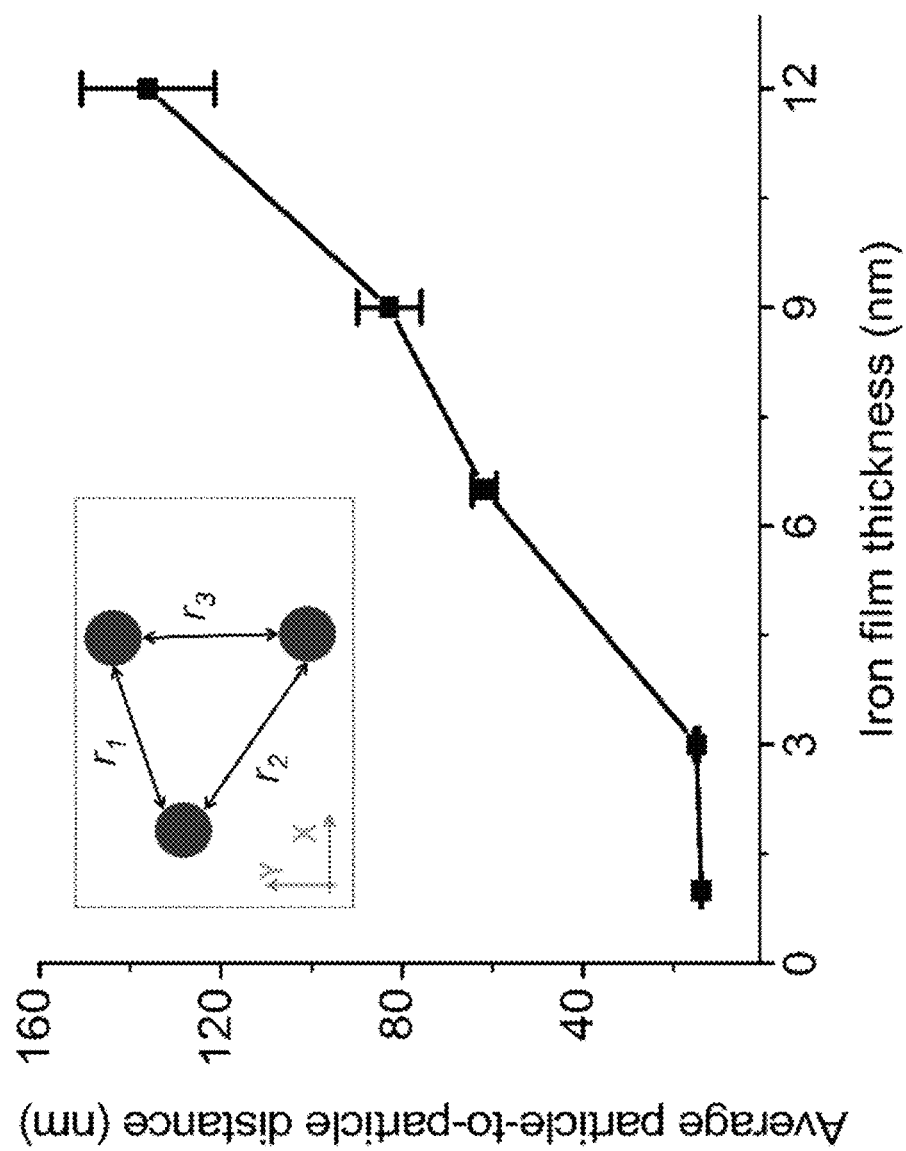

FIG. 25 depicts the calculated distance between the iron particles based on the Delaunay triangle selection algorithm. The inset illustrates the geometry definition of nearest neighbor particles. The average particle-to-particle distance is the mean of $r_1$, $r_2$ and $r_3$.

Figure 26:
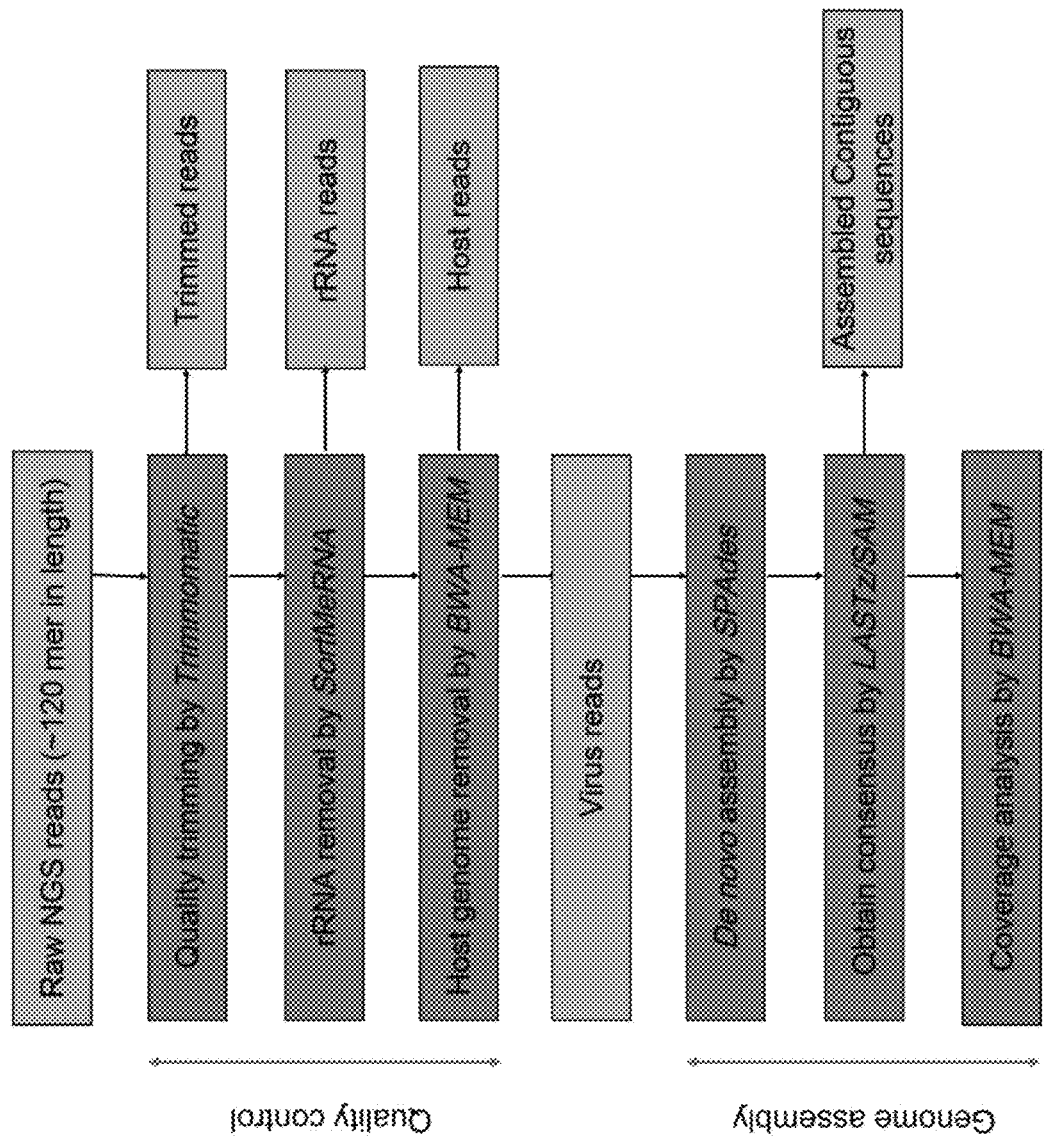

FIG. 26 depicts a diagram of the data processing pipeline for NGS.

FIG. 27A through FIG. 27J depict controlled N-MWCNT growth and tunable size-based filtration of the CNT-STEM. Microscopy images of the N-MWCNT porous wall in the CNT-STEM (FIG. 27A through FIG. 27E). (FIG. 27A) Bright-field optical microscopy image showing the top view of the droplet-shaped porous wall made by the aligned N-MWCNTs on a silicon substrate. Scale bar, 2 mm. (FIG. 27B) Scanning electron microscopy (SEM) image of the aligned N-MWCNTs. Scale bar, 50 μm. (FIG. 27C) High-magnification SEM image showing a side view of the aligned N-MWCNTs. Scale bar, 100 nm. (FIG. 27D) Transmission electron microscopy (TEM) image of AACVD synthesized N-MWCNTs of various diameters. Scale bar, 20 nm. (FIG. 27E) High-resolution TEM image showing the multiwall structure N-MWCNT. Scale bar, 5 nm. (FIG. 27F) Formation of iron nanoparticle catalyst and growth of N-MWCNTs on iron catalyst layers with different thicknesses. Top row: SEM images showing top views of iron particles formed on a silicon surface after 850° C. thermal treatment in AACVD. Thicknesses of iron catalyst thin films are 1, 3, 6.5, 9 and 12 nm. Middle and bottom row: SEM images of cross-sectional views of an aligned N-MWCNT structure after 30 minutes N-MWCNT growth by AACVD. Scale bars, top: 100 nm, middle: 10 μm, bottom: 200 nm. Diameter (FIG. 27G) and density (FIG. 27H) of iron particles (red) and N-MWCNT (black) as a function of iron film thickness (n=8). (FIG. 27I) Inter-tubular distance measured by image analysis as a function of iron film thickness (n=8). (FIG. 27J) Calculated porosity of the N-MWCNT wall (n=8).

FIG. 28A through FIG. 28F depict Raman spectra of the newly synthesized N-MWCNT structures on silicon substrates and the effect of the synthesis time on the height, diameter and density of the aligned N-MWCNT structure. Geometrical parameters were measured from SEM images. (FIG. 28A) Raman spectra of the N-MWCNT structures synthesized on 3 nm, 6.5 nm and 12 nm thick iron catalyst thin films. The Raman spectra indicate the aligned N-MWCNT has D, G and D' band peaks at 1352, 1578 and 2659 $cm^{-1}$, respectively. The results are consistent with previous studies on N-MWCNT. (FIG. 28B) Plot of the peak height ratio of the D band and G band of the N-MWCNT structures formed on 3 nm, 6.5 nm and 12 nm thick iron catalyst thin films over synthesis time. Thicker iron catalyst layer results in lower D/G band ratio. (FIG. 28C) Height of N-MWCNT structure synthesized for 30 minutes on 1 nm, 3 nm, 6.5 nm, 9 nm and 12 nm thick iron thin films (n=8). (b-d) The effect of the synthesis time on the height (FIG. 28D), diameter (FIG. 28E) and linear density (FIG. 28F) of the N-MWCNT structure. The N-MWCNT was grown on 3 nm, 6.5 nm and 12 nm thick iron catalyst thin films under 5, 10, 20, 30 and 40 minutes of AACVD synthesis (n=8).

Figures 29A, 29B:
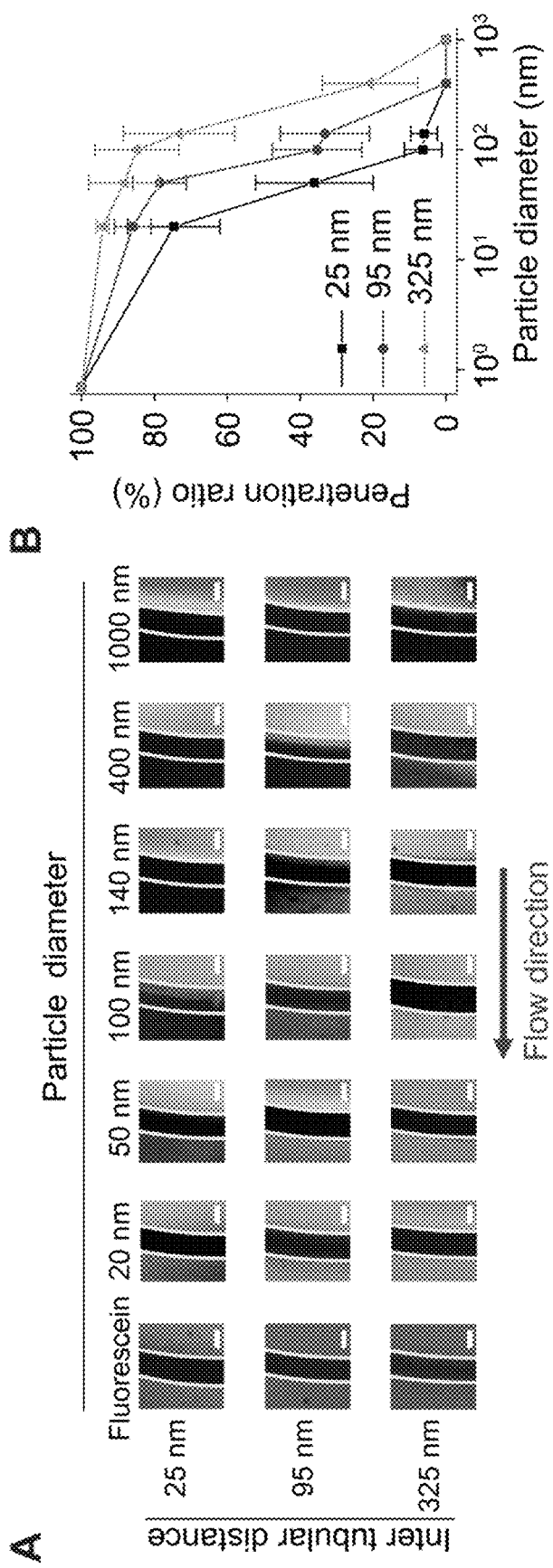

FIG. 29A and FIG. 29B depict the measured particle size-dependent filtration characteristics of CNT-STEMs with N-MWCNT inter-tubular distances of 25 nm, 95 nm, and 325 nm, using small molecule fluorescein and fluorescent polystyrene nanospheres of 20 nm, 50 nm, 100 nm, 140 nm, 400 nm, and 1000 nm in diameter. (FIG. 29A) Fluorescence microscope images showing fluorescein solution and fluorescent polystyrene nanospheres of various diameters being filtered by the CNT-STEM. The direction of the flow is from right to left as indicated by the red arrows. Yellow lines delineate the contours of the N-MWCNT structures. Scale bars, 50 μm. (FIG. 29B) Penetration of fluorescein and fluorescence polystyrene nanospheres through the N-MWCNT structure (n=8).

Figures 30A, 30B:
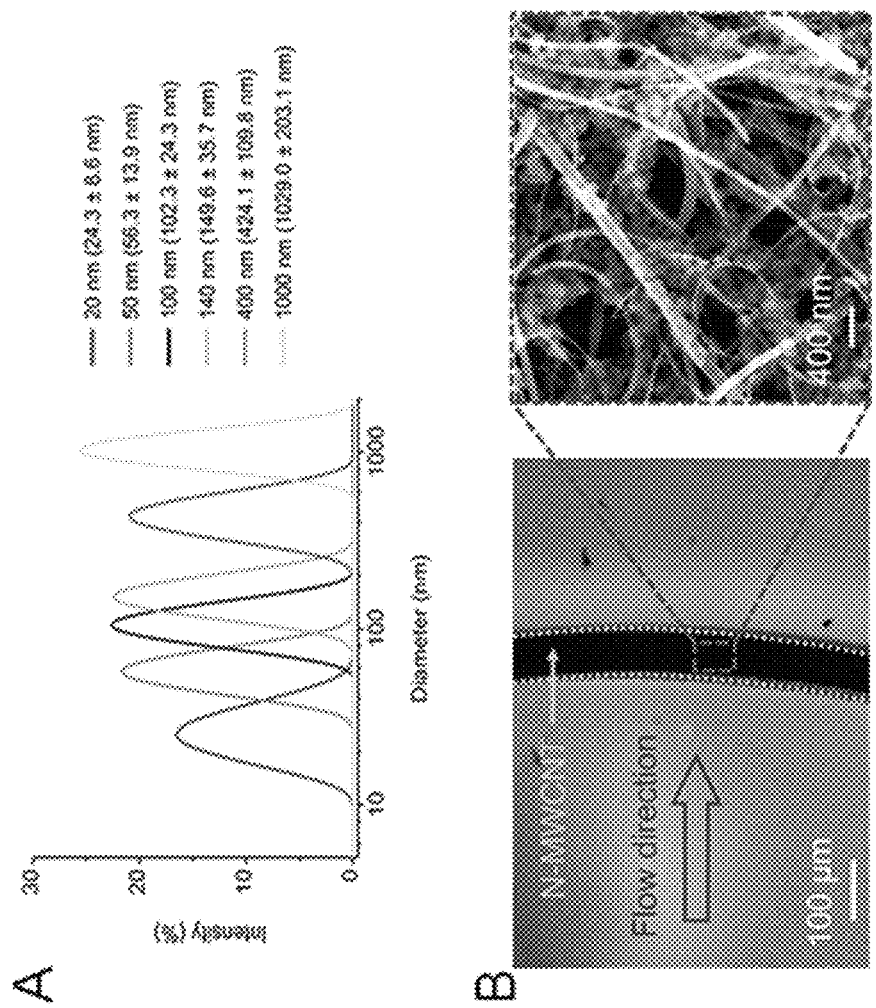

FIG. 30A and FIG. 30B depict the characterization of size-based particle capture by CNT-STEM. (FIG. 30A) Diameter distribution of fluorescent polystyrene nanospheres measured by laser diffraction. (FIG. 30B) Florescence microscopic image showing the transport of 100 nm fluorescently labeled nanospheres in CNT-STEM device with 95 nm inter-tubular distance. Inset is a SEM image of nanospheres trapped inside N-MWCNT structure of the CNT-STEM.

FIG. 31 depicts a table listing the measurement of the inter-tubular distance of N-MWCNT forest and the corresponding critical particle sizes of CNT-STEM.

FIG. 32A through FIG. 32D depict the enrichment and concentration of virus swab samples by CNT-STEM. (FIG. 32A) Top-view illustration of viruses passing through and captured by the N-MWCNT array. (FIG. 32B) On-chip indirect fluorescent antibody (IFA) staining of captured H5N2 AIV inside CNT-STEMs with 25 nm, 95 nm, and 325 nm inter-tubular distances. Fluorescence microscopy images of the CNT-STEMs, red arrows indicate the flow direction. Yellow dotted lines delineate the contours of the N-MWCNT structures. The control sample was allantoic fluid without viruses. Scale bars, 25 µm. (FIG. 32C) Capture efficiency of CNT-STEMs with inter-tubular distance of 25, 95, and 325 nm measured by rRT-PCR (n=6). (FIG. 32D) Examples of rRT-PCR AIV detection curves for virus titers of $10^4$, $10^3$, $10^2$, $10^1$, and $10^0$ $EID_{50}$/mL without (i) and with (ii) CNT-STEM enrichment. a.u., arbitrary unit.

Figure 33:
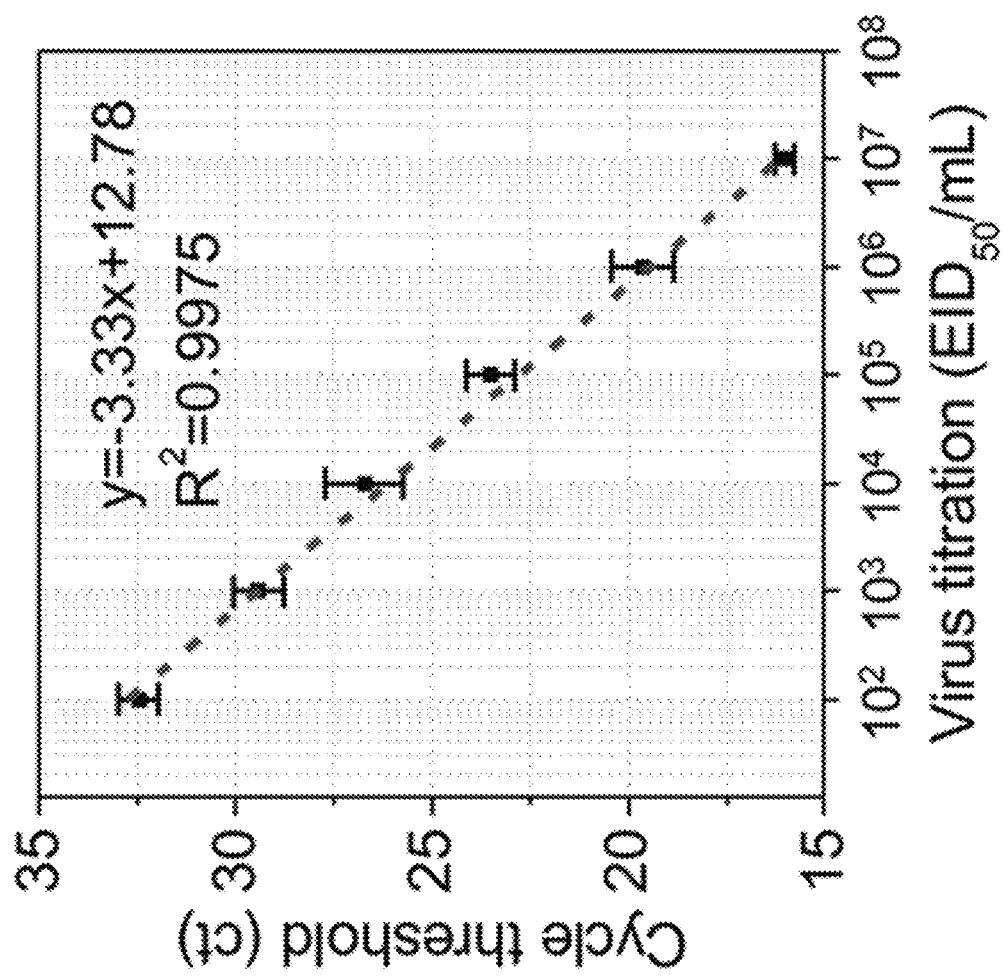

FIG. 33 depicts the standard curve for the rRT-PCR detection of H5N2 AIV (n=4 each). The rRT-PCR assay had efficiency of 99.66% with the slope of the standard curve −3.33. The concentration of the original H5N2 sample (no dilution) was ~$1.8 \times 10^8$ $EID_{50}$. No signal was detected after $10^7$ dilution thus the detection limit here was $1.8 \times 10^2$ $EID_{50}$/mL.

Figure 34:
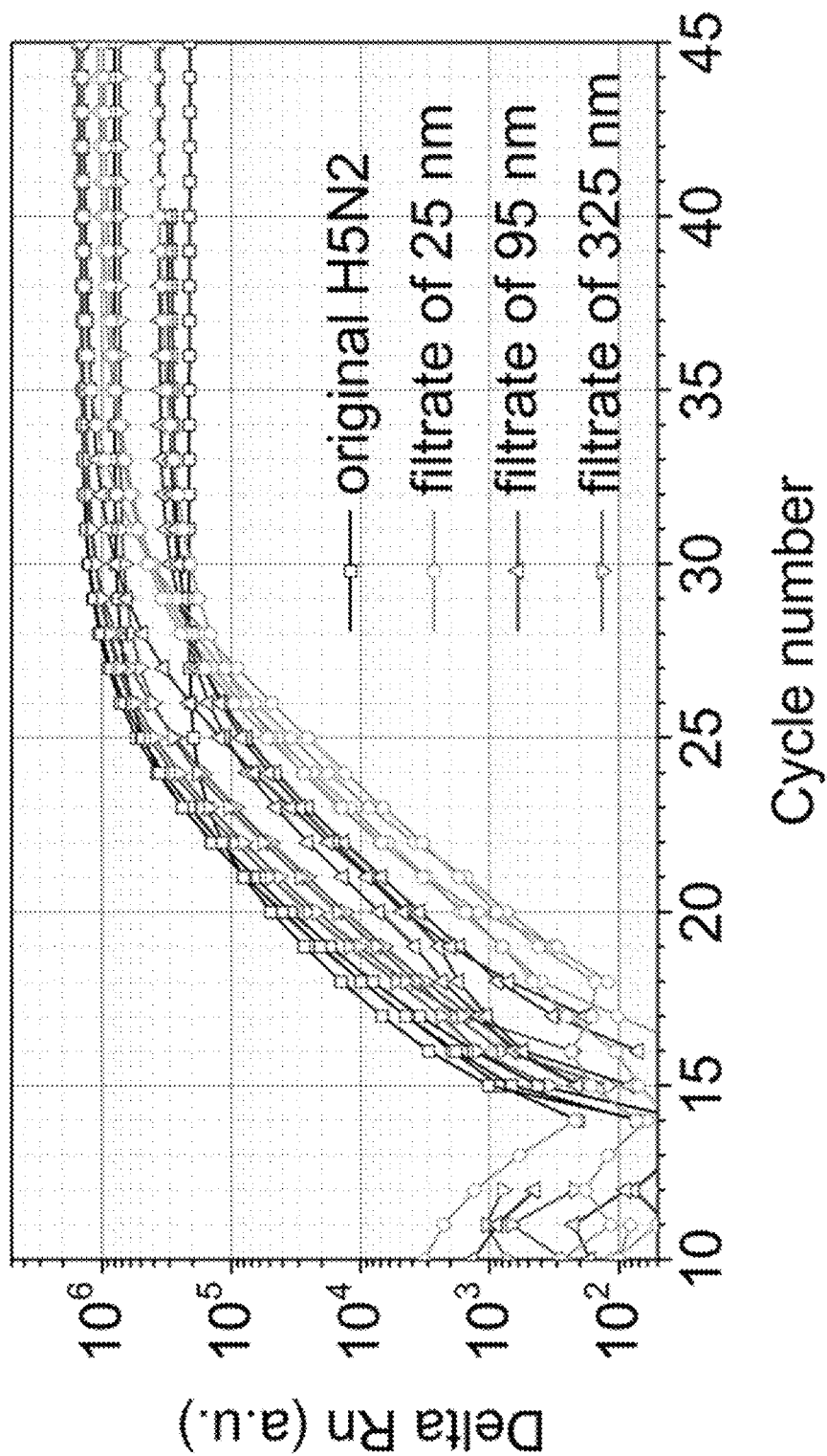

FIG. 34 depicts the capture efficiency measurement of CNT-STEM with 25 nm, 95 nm, and 325 nm inter-tubular distances when loading H5N2 AIV of $10^6$ $EID_{50}$/mL titer into each device (n=6). The Ct values of filtrates and the original sample were measured (n=6 each).

Figure 35:
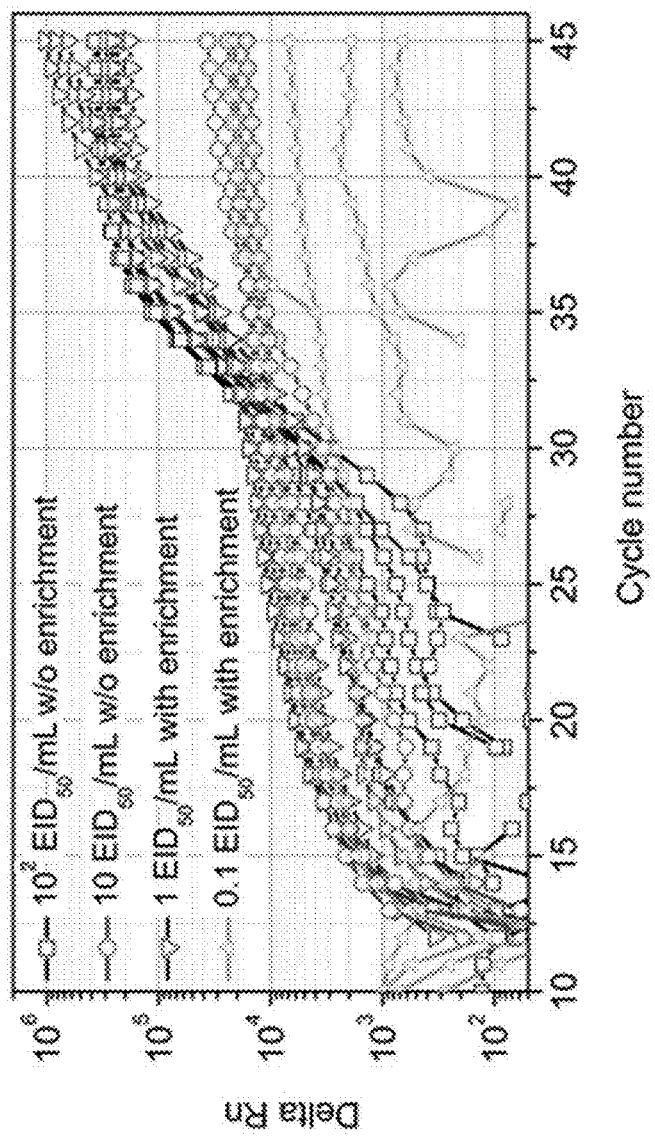

FIG. 35 depicts the rRT-PCR curves of H5N2 AIV samples of 10 $EID_{50}$/mL and $10^2$ $EID_{50}$/mL titers without enrichment and those of 0.1 $EID_{50}$/mL and 1 $EID_{50}$/mL titers with CNT-STEM enrichment (n=6).

Figure 36:
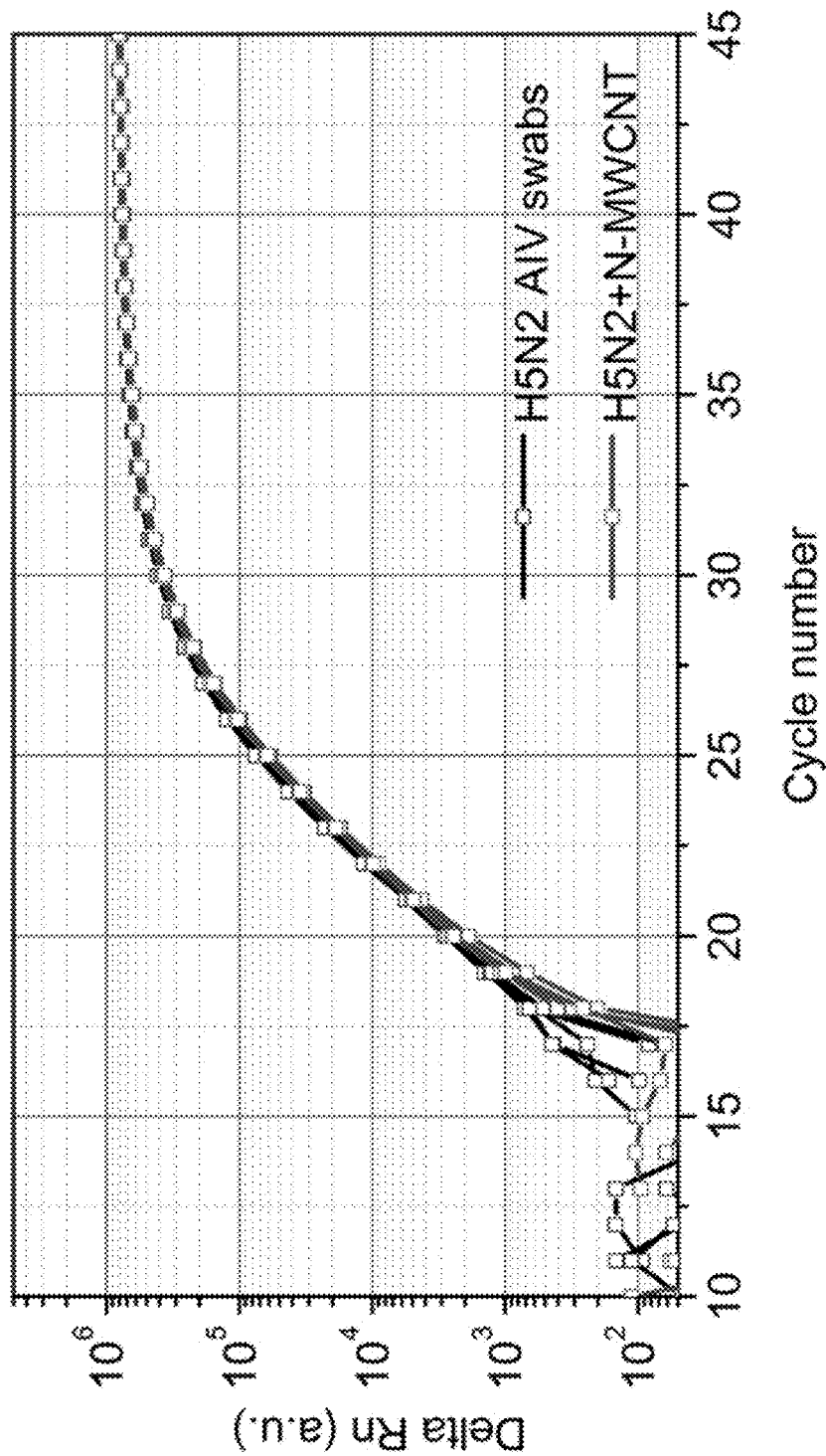

FIG. 36 depicts the compatibility test of N-MWCNT to rRT-PCR. The "H5N2+N-MWCNT" samples were prepared by scraping N-MWCNT from the CNT-STEM without virus processing using razor blade and then mixed with swab-mimicking H5N2 AIV samples of $5 \times 10^4$ $EID_{50}$/mL titer for rRT-PCR detection (n=5).

Figures 37A, 37B, 37C:
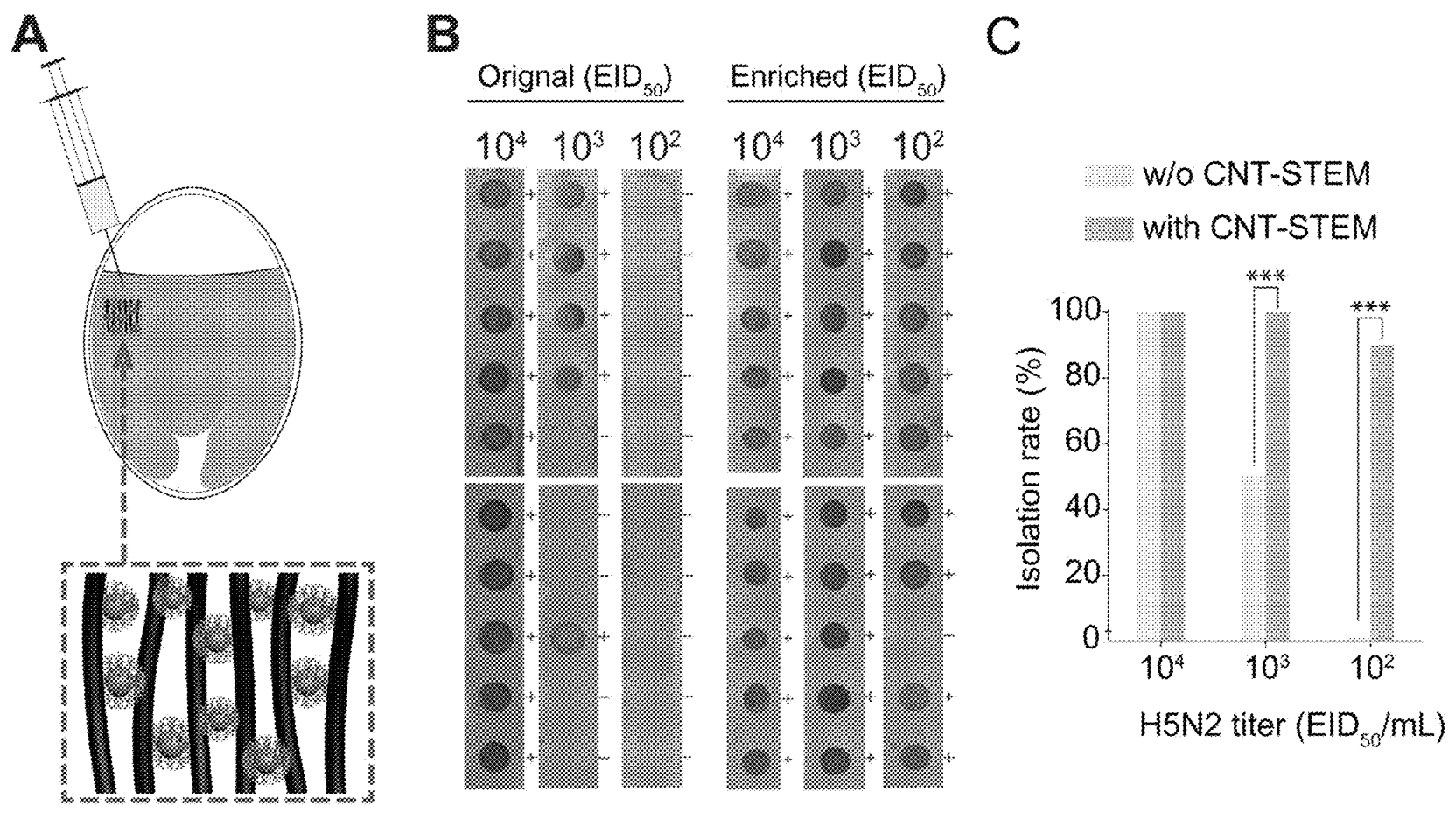

FIG. 37A through FIG. 37C depict the results of CNT-STEM enriching viruses viability and improving the minimal virus concentration of virus isolation. (FIG. 37A) Illustration showing inoculation of virus-embedded N-MWCNT structure into embryonated chicken egg (ECE). (FIG. 37B) Dot-ELISA detection of H5N2 AIV after virus cultivation in ECEs. Virus samples inoculated into chicken eggs were either from original virus samples in the titers of $10^2$, $10^3$, and $10^4$ $EID_{50}$/mL or CNT-STEM enriched samples of the same corresponding original titers. A darken spot with a positive sign indicated that H5N2 AIV successfully propagated inside the chicken egg. (FIG. 37C) Success rates of AIV isolation via egg inoculation with and without using the CNT-STEM for original virus titers of $10^4$, $10^3$, and $10^2$ $EID_{50}$/mL (n=10). ***: $p \leq 0.001$.

Figure 38A:
Figure 38B:
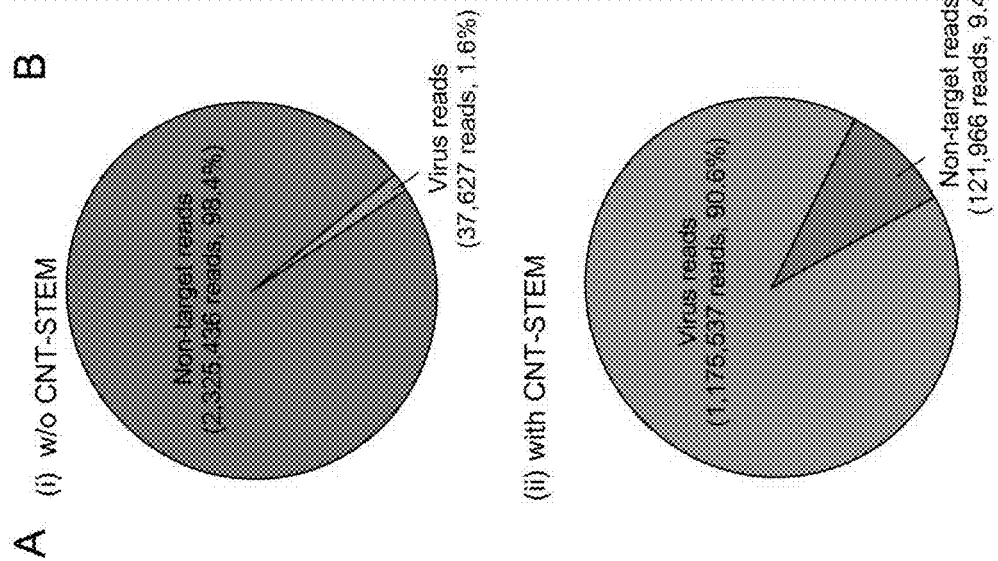
Figure 38C:
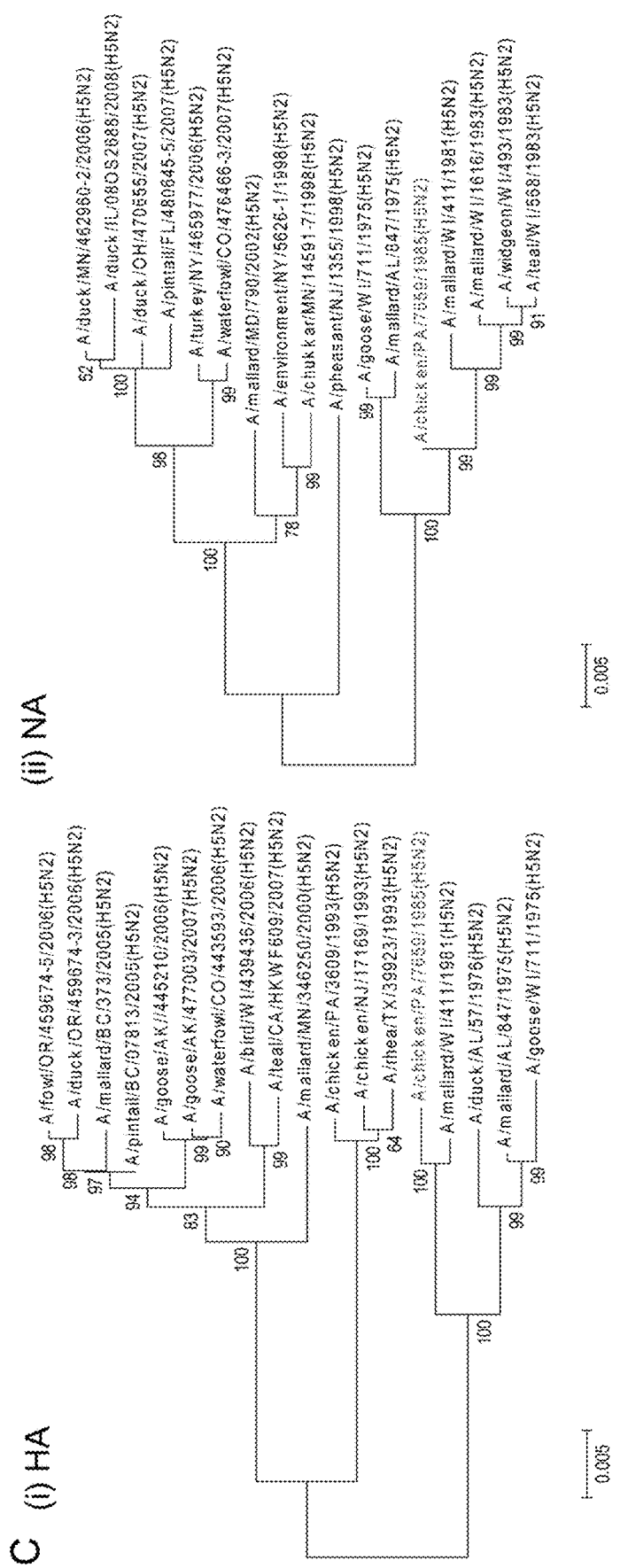

FIG. 38A through FIG. 38C show CNT-STEM prepares mimic field samples for NGS virus analysis. (FIG. 38A) Raw reads generated by NGS without (i) and with (ii) CNT-STEM enrichment. (FIG. 38B) Circos plots of assembled contiguous sequences generated from NGS reads of the CNT-STEM enriched H5N2 LPAIV samples. Track 1 [outermost]: scale mark. Track 2: iSNV. Track 3: variants comparing to H5N2 AVI strain A/mallard/WI/411/1981. Track 4: coverage (black) on scale of 0 to 30k reads. Track 5: de novo assembled contigs after CNT-STEM enrichment (grey). Track 6: open reading frames (green). Color coding in tracks 2 and 3: deletion (black), transition (A-G: fluorescent green, G-A: dark green, C-T: dark red, T-C: light red), transversion (A-C: brown, C-A: purple, A-T: dark blue, T-A: fluorescent blue, G-T: dark orange, T-G: violet, C-G: yellow, G-C: light violet). (FIG. 38C) Phylogenetic tree plots generated by comparing the HA (i) and NA (ii) genes of the sequenced H5N2 AIV (highlighted in red) to those of closely related AIV strains isolated in North America from Genbank.

FIG. 39 depicts a table listing the assembled contigs of the LP H5N2 AIV sample enriched by CNT-STEM.

Figure 40A:
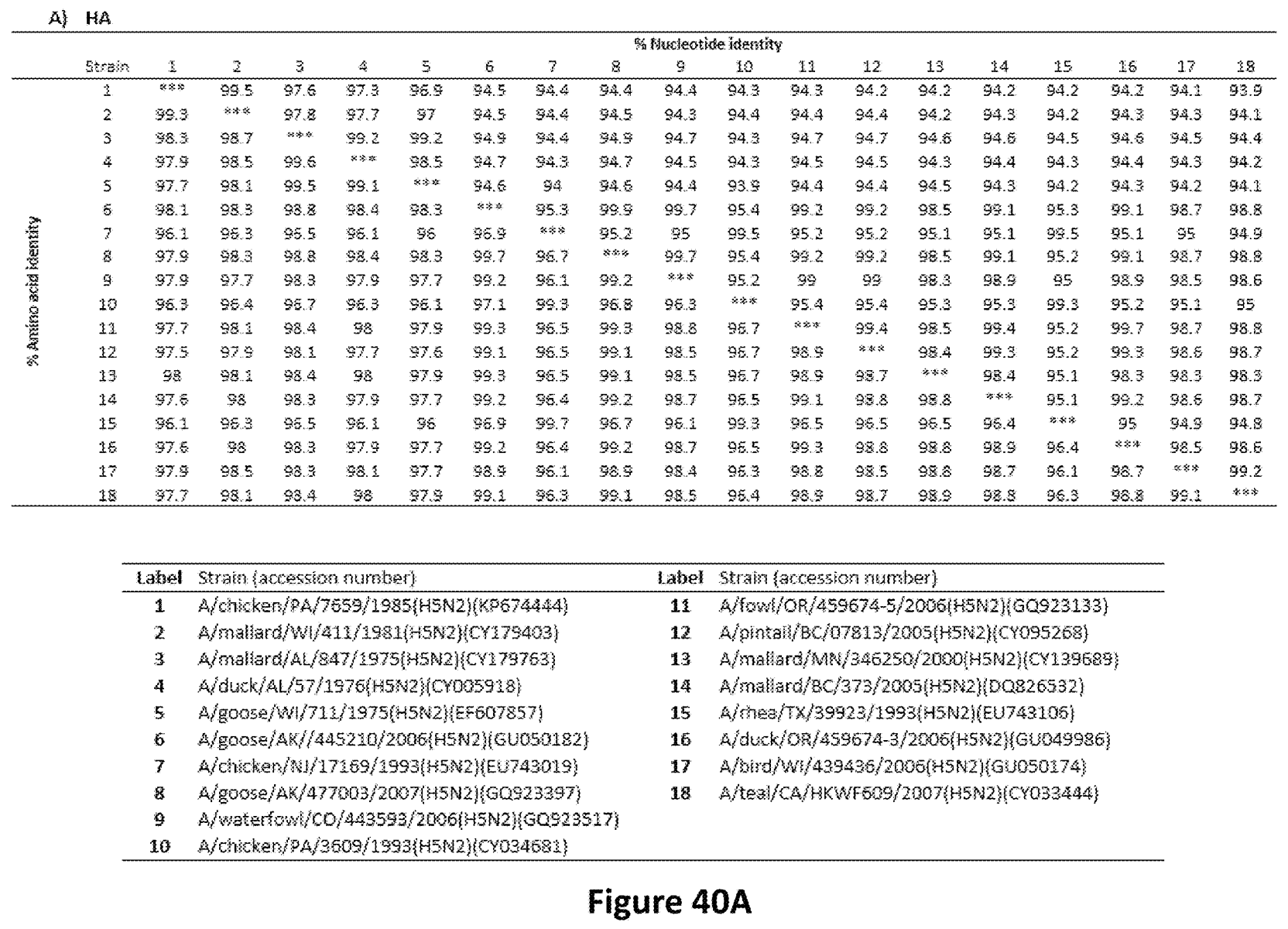
Figure 40B:
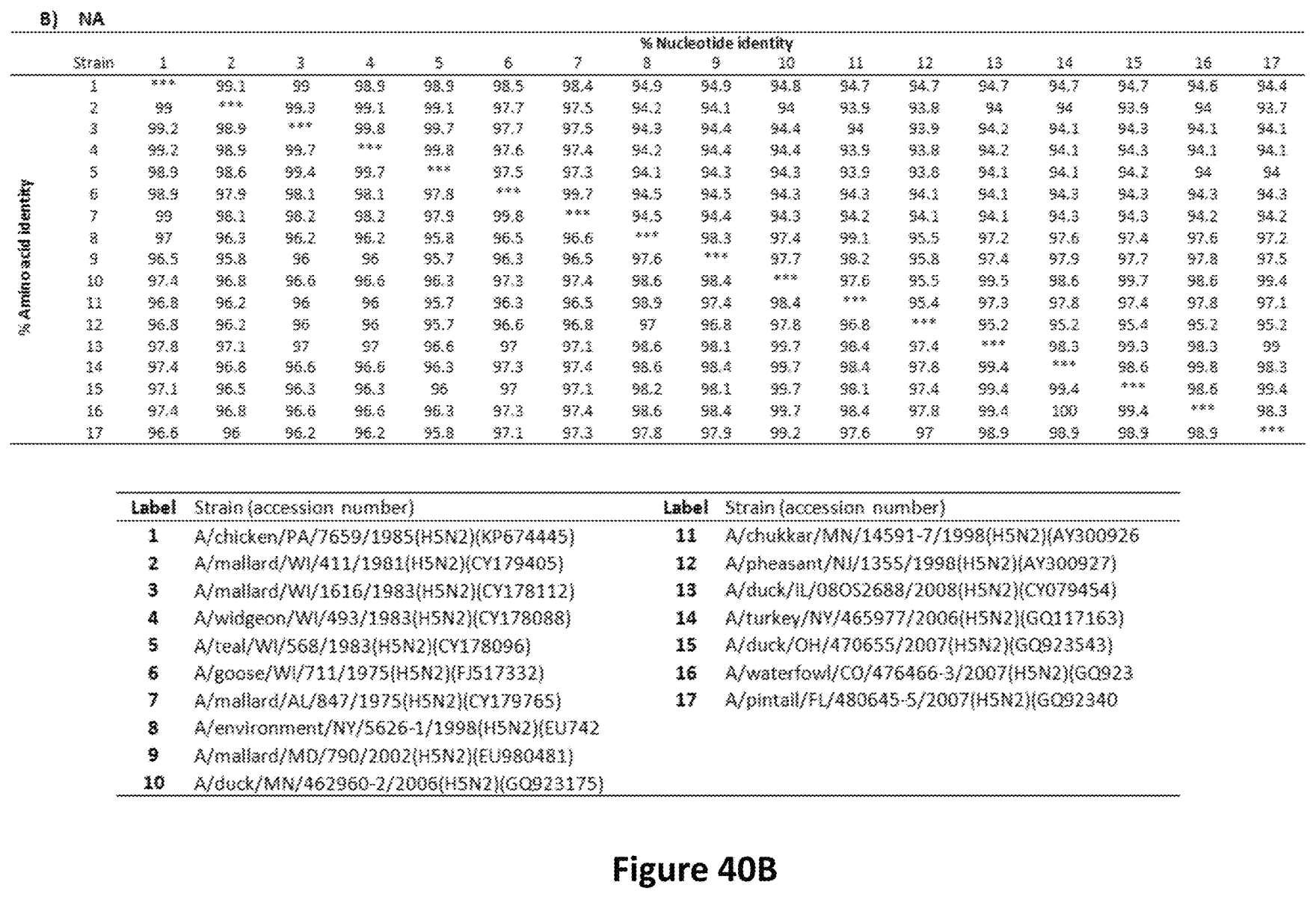

FIG. 40A and FIG. 40B depict tables showing the phylogenetic analysis of the sequenced H5N2 strain (A/chicken/PA/7659/1985) to closely related H5N2 AIV strains isolated from US/Canada in Genbank for (FIG. 40A) the HA gene and (FIG. 40B) the NA gene.

Figure 41:
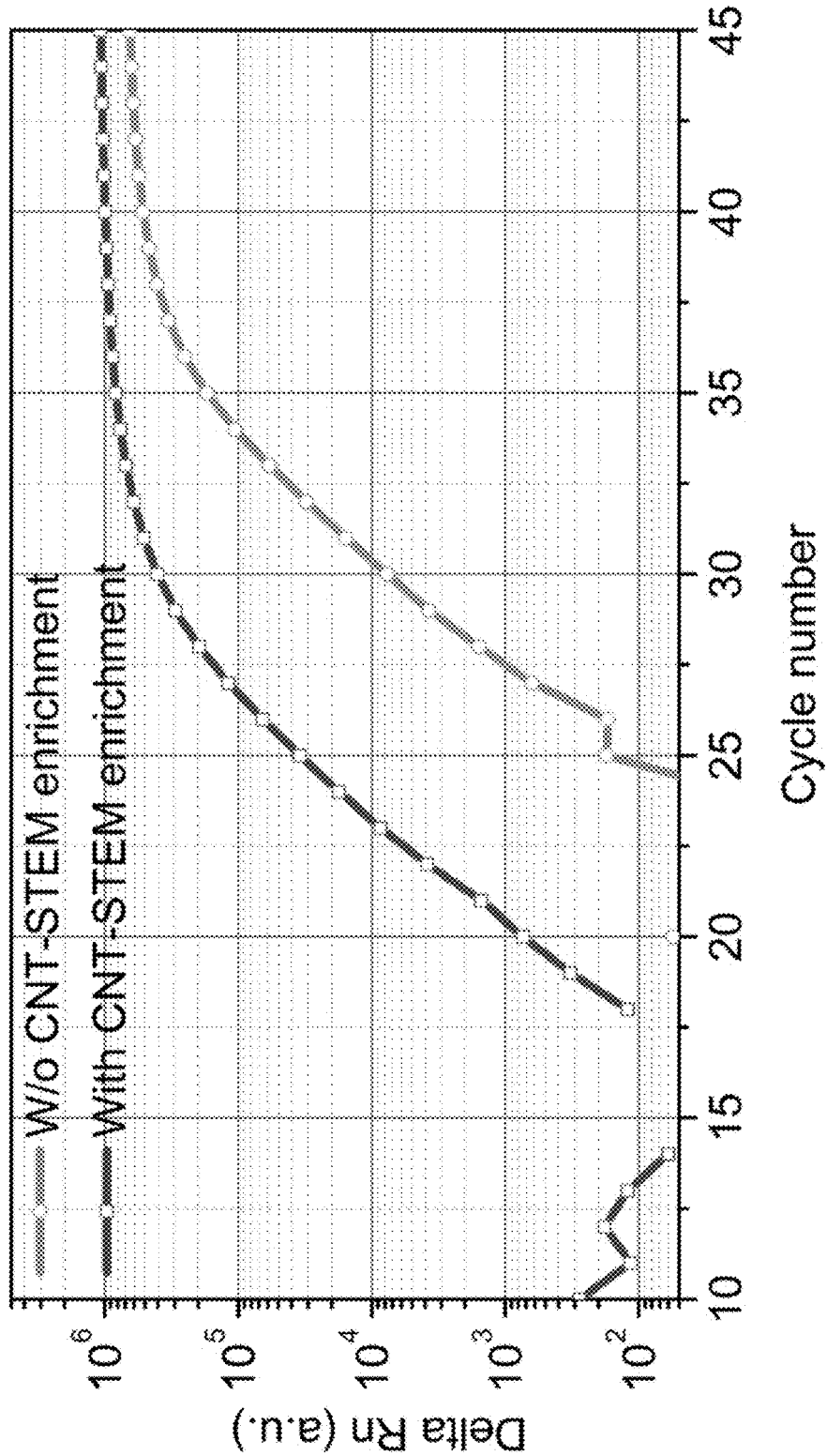

FIG. 41 depicts the results of rRT-PCR detection of the H11N9 AIV duck swab with and without CNT-STEM enrichment.

Figure 42A:
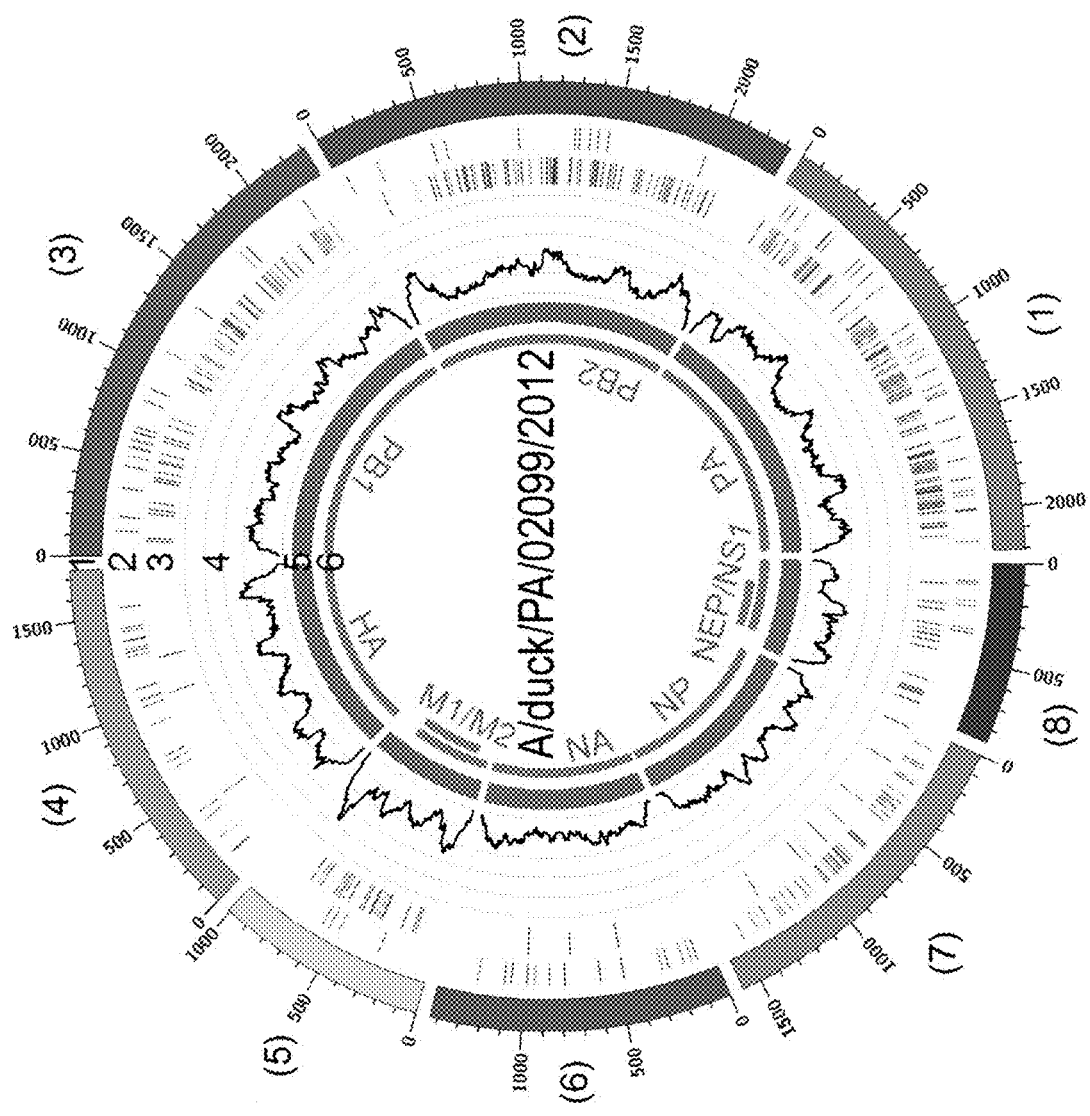
Figure 42B:
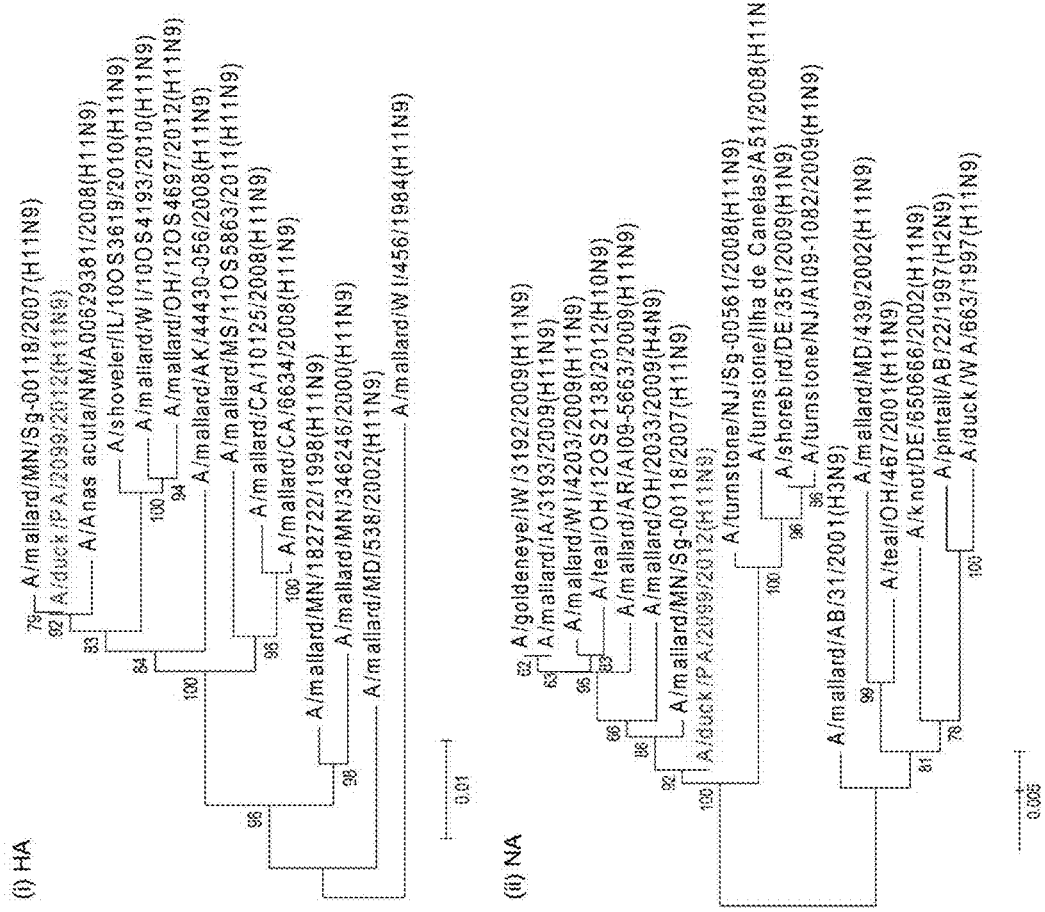

FIG. 42A and FIG. 42B depict the identification of an emerging AIV H11N9 strain from a surveillance swab sample using CNT-STEM followed by NGS and de novo genome sequence assembly. (FIG. 42A) Circos plot of assembled H11N9 contigs generated by NGS from a CNT-STEM enriched wild duck swab pool. Track 1 [outermost]: scale mark. Track 2: Identified iSNV. Track 3: Variants compared to a previously reported H11N9 AIV strain (A/duck/MN/Sg-00118/2007). Track 4: Coverage on scale of 0 to 50 reads (black). Track 5: de novo assembled contigs after CNT-STEM enrichment (grey). Track 6: Open reading frames (green). Color coding in tracks 2 and 3: deletion (black), transition (A-G: fluorescent green, G-A: dark green, C-T: dark red, T-C: light red), transversion (A-C: brown, C-A: purple, A-T: dark blue, T-A: fluorescent blue, G-T: dark orange, T-G: violet, C-G: yellow, G-C: light violet). (FIG. 42B) Phylogenetic tree plots generated by comparing the HA (a) and NA (b) genes of the sequenced H11N9 AIV (highlighted in red) to selected closely related AIV strains isolated in North America from Genbank.

FIG. 43 is a table listing the assembled contigs of the H11N9 AIV field sample enriched by CNT-STEM.

FIG. 44A and FIG. 44B depict tables showing the phylogenetic analysis of the emerging H11N9 strain (A/duck/PA/02099/2012) to previously reported and closely related AIV strains for (FIG. 44A) the HA gene and (FIG. 44B) the NA gene.

Figure 45A:
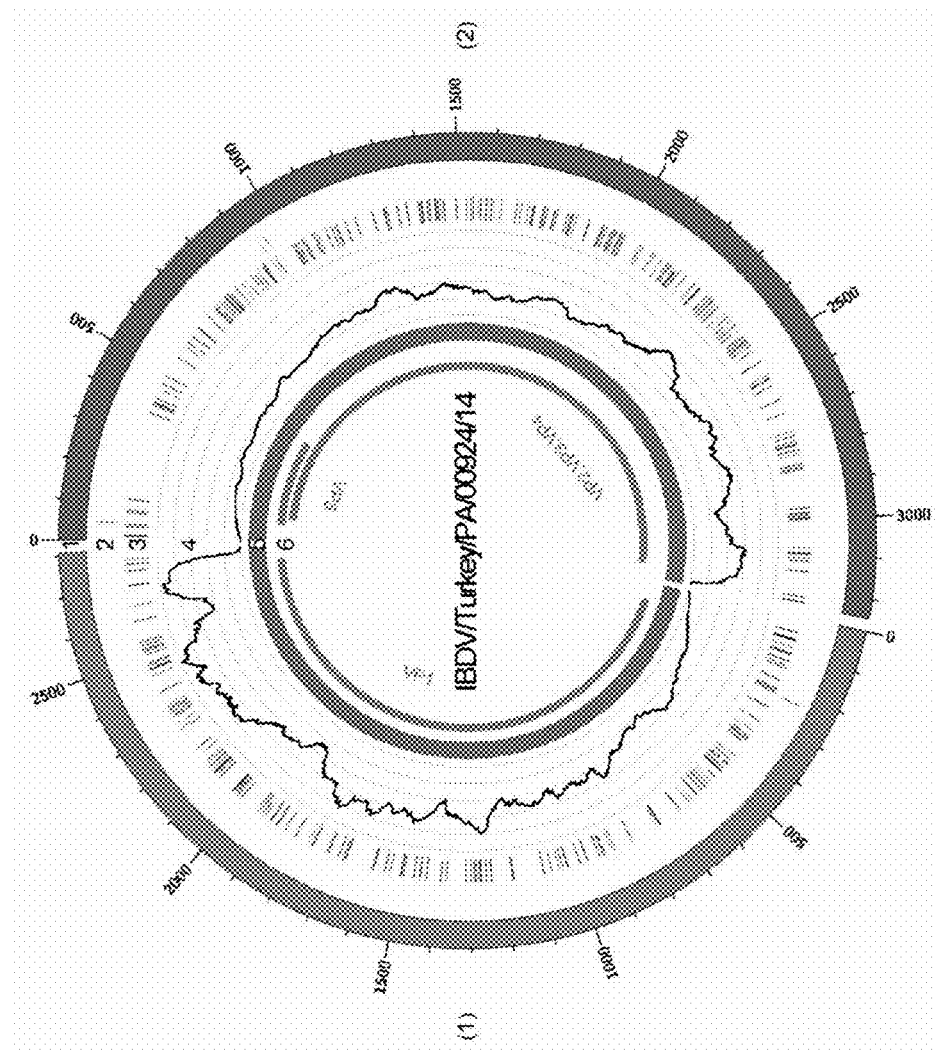
Figure 45B:
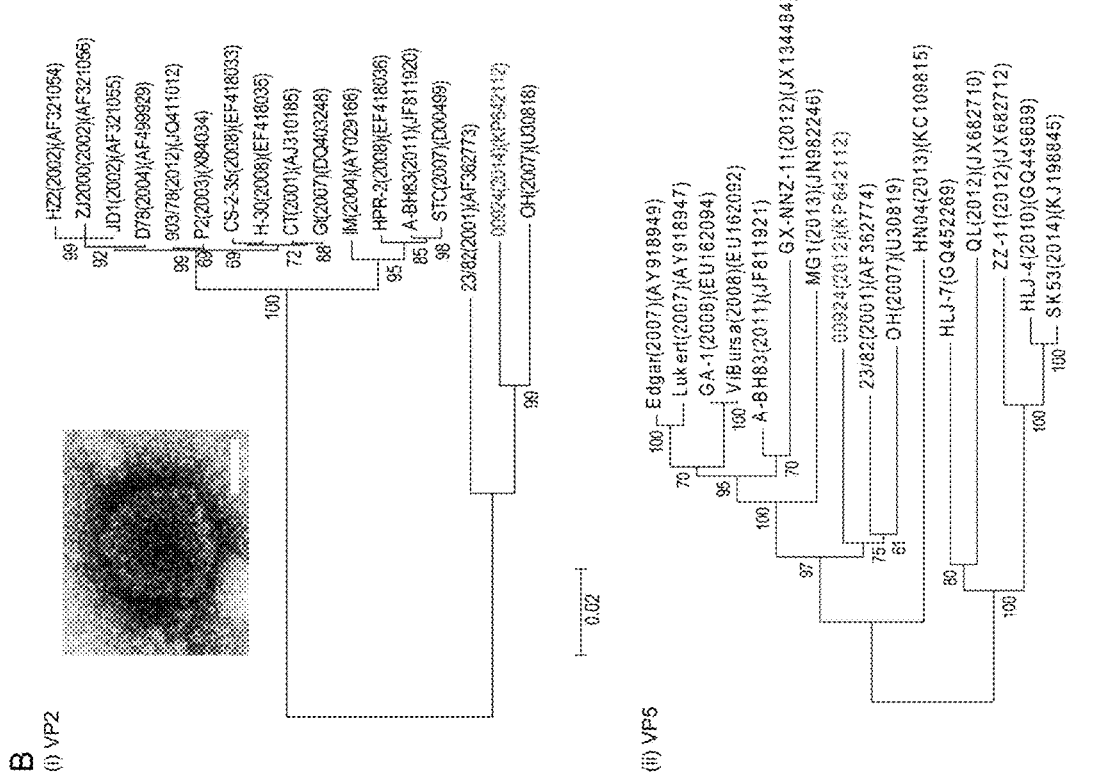

FIG. 45A and FIG. 45B depict the identification of a new IBDV strain from a turkey eyelid tissue sample using CNT-STEM followed by NGS and de novo genome sequence assembly. (FIG. 45A) Circos plots of assembled contiguous sequences generated from NGS reads of the CNT-STEM enriched IBDV samples. Track 1 [outermost]: scale mark. Track 2: iSNV. Track 3: variants comparing to OH Strain (U30818) (b). Track 4: coverage (black) on scale of 0 to 2625 reads. Track 5: de novo assembled contigs after CNT-STEM enrichment (grey). Track 6: open reading frames (green). Color coding in tracks 2 and 3: deletion (black), transition (A-G: fluorescent green, G-A: dark green, C-T: dark red, T-C: light red), transversion (A-C: brown, C-A: purple, A-T: dark blue, T-A: fluorescent blue, G-T: dark orange, T-G: violet, C-G: yellow, G-C: light violet). (FIG. 45B) Phylogenetic tree plots generated by comparing the open reading frames VP2/VP3/VP4 (a) and VP1 (b) of IBDV/Turkey/PA/00924/14 (highlighted in red) to previously reported IBDVs.

FIG. 46 is a table comparing contigs of the unknown virus (IBDV/Turkey/PA/00924/14) generated by de novo assembly after CNT-STEM enrichment and NGS to the closest IBDV strains in Genbank.

Figure 47A:
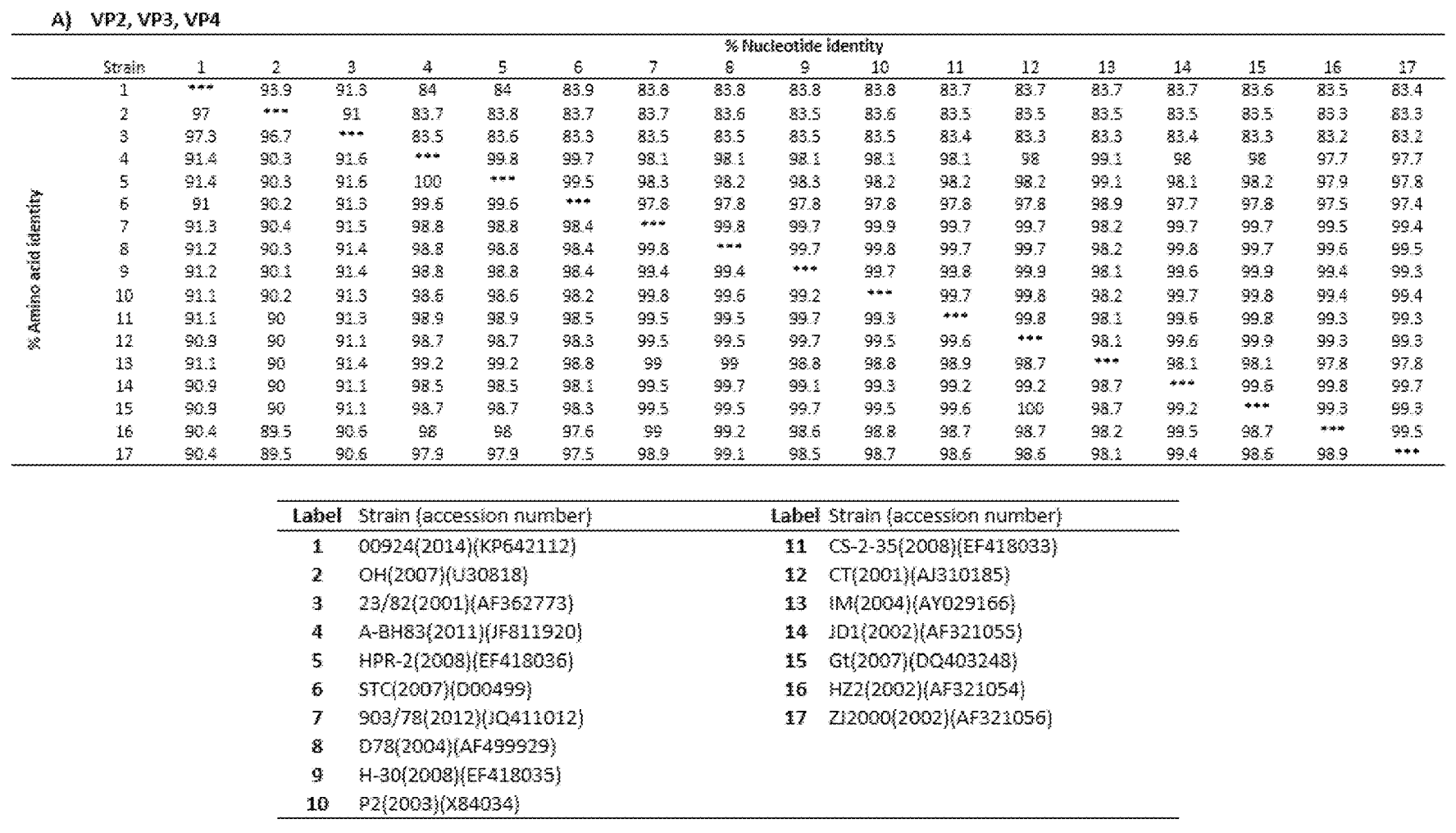

FIG. 47A and FIG. 47B depict tables showing the SNP/variant analysis of the "unknown" virus (IBDV/Turkey/PA/00924/14) to sequenced IDBV virus strains for (FIG. 47A) capsid proteins VP2, VP3, and VP4 and (FIG. 47B) VP1.

FIG. 48 is a table comparing CNT-STEM to several reported ultrafiltration devices.

FIG. 49 is a table listing the yield and reliability analysis of CNT-STEM fabrication, assembly and testing.

FIG. 50A is a table comparing the cycle threshold (Ct) values of enriching plum pox virus using a current USDA virus enrichment protocol versus an enrichment protocol using CNT-STEM with 25 nm inter-tubular distance.

FIG. 50B is a table listing the results of enriching herpes simplex virus using CNT-STEM.

DETAILED DESCRIPTION

The present invention provides for an enrichment platform device and methods for size-based capture of particles in solution. The invention is useful for label-free capture of any particle. The invention is also useful for filtering particles out of solution. The invention is also useful for concentrating and isolating viable particles out of solution for analysis.

In one embodiment, the device comprises vertically-aligned carbon nanotubes (VACNT). In one embodiment, the device comprises nanowires. In one embodiment, the enrichment platform device is a microfluidic device. In another embodiment, the enrichment platform device is a portable device wherein sample solutions are passed through by hand push.

The invention provides a method for making the enrichment platform device. In one embodiment, the method comprises chemical-vapor deposition. In another embodiment, the method comprises deep reactive-ion etching (DRIE), metal assisted silicon etching, and wet etching.

The invention provides methods for capturing particles in solution. In one embodiment, the method filters particles out of a solution. In one embodiment, the method captures particles in a solution for analysis. In one embodiment, the method captures and releases viable particles for analysis.

Definitions

It is to be understood that the figures and descriptions of the present invention have been simplified to illustrate elements that are relevant for a clear understanding of the present invention, while eliminating, for the purpose of clarity, many other elements found in typical tissue engineering system and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "carbon nanotubes" (CNTs) is used herein in a generic sense to include single-walled and multi-walled carbon nanotubes, carbon nanofibers, carbon nanofilaments, and carbon nanoropes.

The term "channel" refers to a gap between any two protrusions. The channels of the present invention may be any convenient size or shape.

As used herein, "chemical vapor deposition" refers to plasma enhanced chemical vapor deposition or thermal chemical vapor deposition.

A "disease" is a state of health of a living organism, wherein the living organism cannot maintain homeostasis, and wherein if the disease is not ameliorated then the living organism's health continues to deteriorate.

In contrast, a "disorder" in a living organism is a state of health in which the living organism is able to maintain homeostasis, but in which the living organism's state of health is less favorable than it would be in the absence of the disorder. Left untreated, a disorder does not necessarily cause a further decrease in the living organism's state of health.

A disease or disorder is "alleviated" if the severity of a symptom of the disease or disorder, the frequency with which such a symptom is experienced by a patient, or both, is reduced.

As used herein, the term "doped" means that for any given carbon nanotube, at least a portion of the carbon sites in the graphitic structure of the carbon nanotube are filled with atoms of the doping material instead of with carbon atoms, such that the portion of carbon sites so filled with the doping material would be detectable by common analytical means known in the art such as, for example, x-ray photoelectric spectroscopy (XPS).

The term "nanowire" as used herein is meant to describe a nanoscale particle typically of high aspect ratio. An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis. Consequently, a nanowire has an aspect ratio greater than about 1.5 or greater than about 2. Short nanowires, sometimes referred to as "nanorods," typically have an aspect ratio between about 1.5 and about 10. Longer nanowires may have an aspect ratio greater than about 10, or even greater than about 10,000. The diameter of a nanowire is typically less than about 500 nm and may be less than 200 nm. In some examples, the diameter of a nanowire may even be less than about 5 nm.

The terms "patient," "subject," "individual," and the like are used interchangeably herein, and refer to any living organism, or cells thereof whether in vitro or in situ, amenable to the methods described herein. In certain non-limiting embodiments, the patient, subject or individual is a human, an animal, an insect, or a plant.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Enrichment Platform Device

The invention provides enrichment platform devices for size-based capture of particles in solution. The enrichment platform device is useful for label-free capture of any particle.

Figures 1A, 1B:
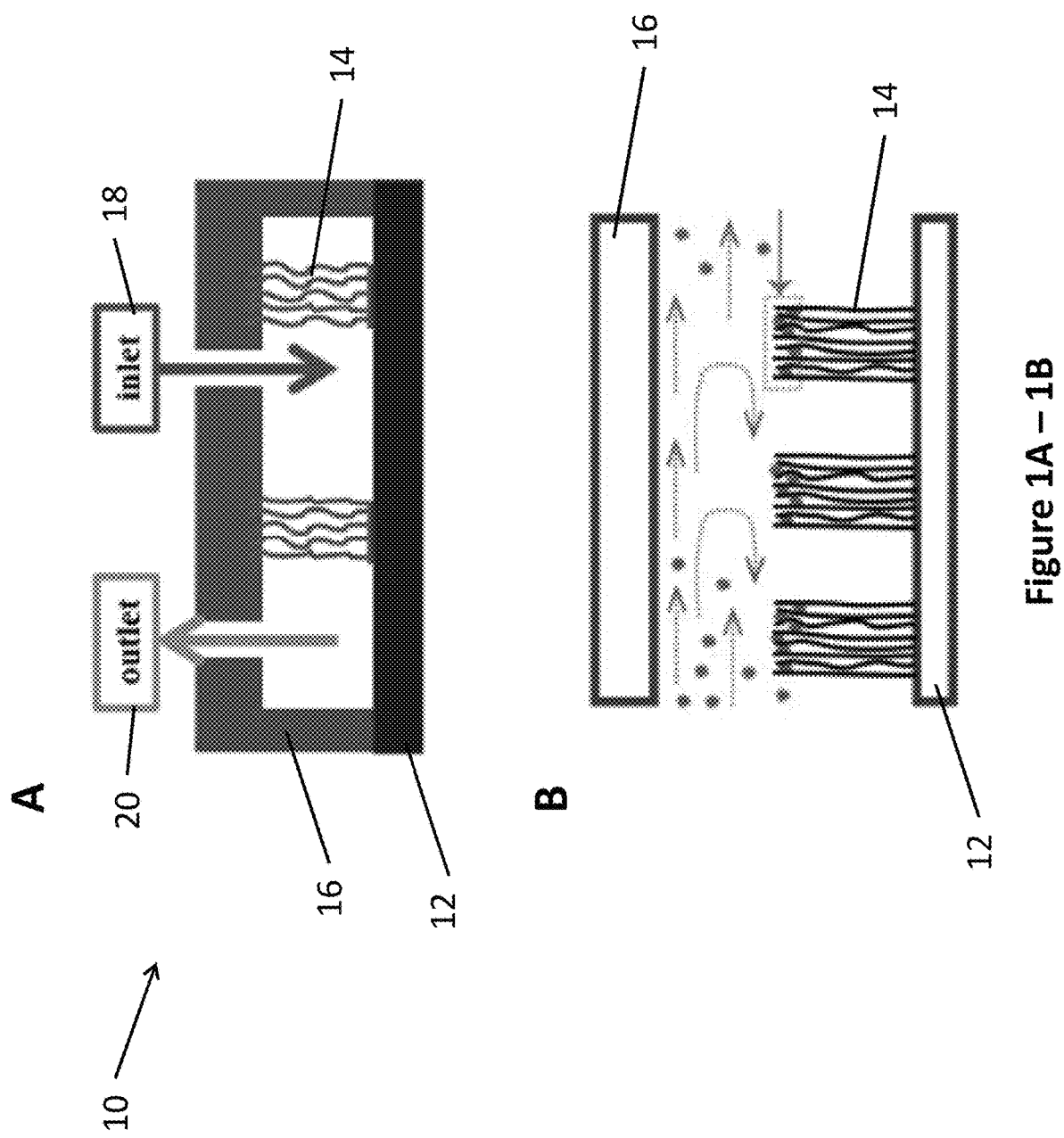
FIG. 1A and FIG. 1B, depicts an illustration of a vertically-aligned carbon nanotube (VACNT) microfluidic device.

Referring now to FIG. 1A, one embodiment of a vertically-aligned carbon nanotubes (VACNT) enrichment platform device 10 is depicted. VACNT enrichment platform device 10 comprises substrate 12, VACNT 14, and cover 16. Substrate 12 can be any substrate known in the art, including, but not limited to, silicon, glass, sapphire, metals, polymers, and the like.

VACNT 14 is attached to substrate 12 at their distal ends. VACNT 14 comprises at least one CNT selected from the group including, but not limited to, single-wall CNT, double-walled CNT, multi-wall CNT, and combinations thereof. In one embodiment, VACNT 14 is doped. Non-limiting examples of doped VACNT 14 include nitrogen-doped VACNT, boron-doped VACNT, silicon-doped VACNT, aluminum-doped VACNT, phosphorus-doped VACNT, and lithium-doped VACNT. In one embodiment, VACNT 14 is doped to enhance biocompatibility, such that the viability of captured particles is preserved.

VACNT 14 is arranged in forests, such that a forest comprises a plurality of VACNT 14. Forests of VACNT 14 can be in any suitable arrangement. Non-limiting examples of VACNT forest arrangements include herringbone pattern (FIG. 17B), continuous sidewalls (FIG. 22B), solid blocks, striped pattern, concentric circles, and the like.

A forest of VACNT 14 comprises gaps between VACNT. In one embodiment, the gap size is at least 1 nm. In various embodiments, the gap size is between 1 nm and 500 nm. In one embodiment, the gap size is dimensioned to fit the diameter of the particles to be captured. In various embodiments, the device comprises a plurality of VACNT forests having different properties. For example, the plurality of VACNT forests may have different gap sizes, different diameters, different thicknesses, and different densities. The device may also comprise a plurality of VACNT forests having single-wall CNT, double-walled CNT, multi-wall CNT, and combinations thereof. The device may also comprise a plurality of VACNT forests having differently doped CNT.

The VACNT forests and substrate 12 are enclosed by cover 16. Cover 16 may be made from any material, including, but not limited to, plastics, metals, glass, polymers, polydimethylsiloxane (PDMS), and the like. Cover 16 comprises at least one inlet 18 and at least one outlet 20 for ingress and egress of sample solution. In one embodiment, cover 16 is bonded to both substrate 12 and VACNT 14, such as in FIG. 1A. In another embodiment, cover 16 is bonded to substrate 12 only, such that VACNT are secured only to substrate 12 at their distal ends and are not connected to anything at their proximal ends, such as in FIG. 1B. In one embodiment, cover 16 is removable.

In one embodiment, the VACNT enrichment platform device 30 is a microfluidic device. In another embodiment, the VACNT enrichment platform device 30 is a portable device wherein sample solutions are passed through by hand push.

Figures 2A, 2B, 2C:
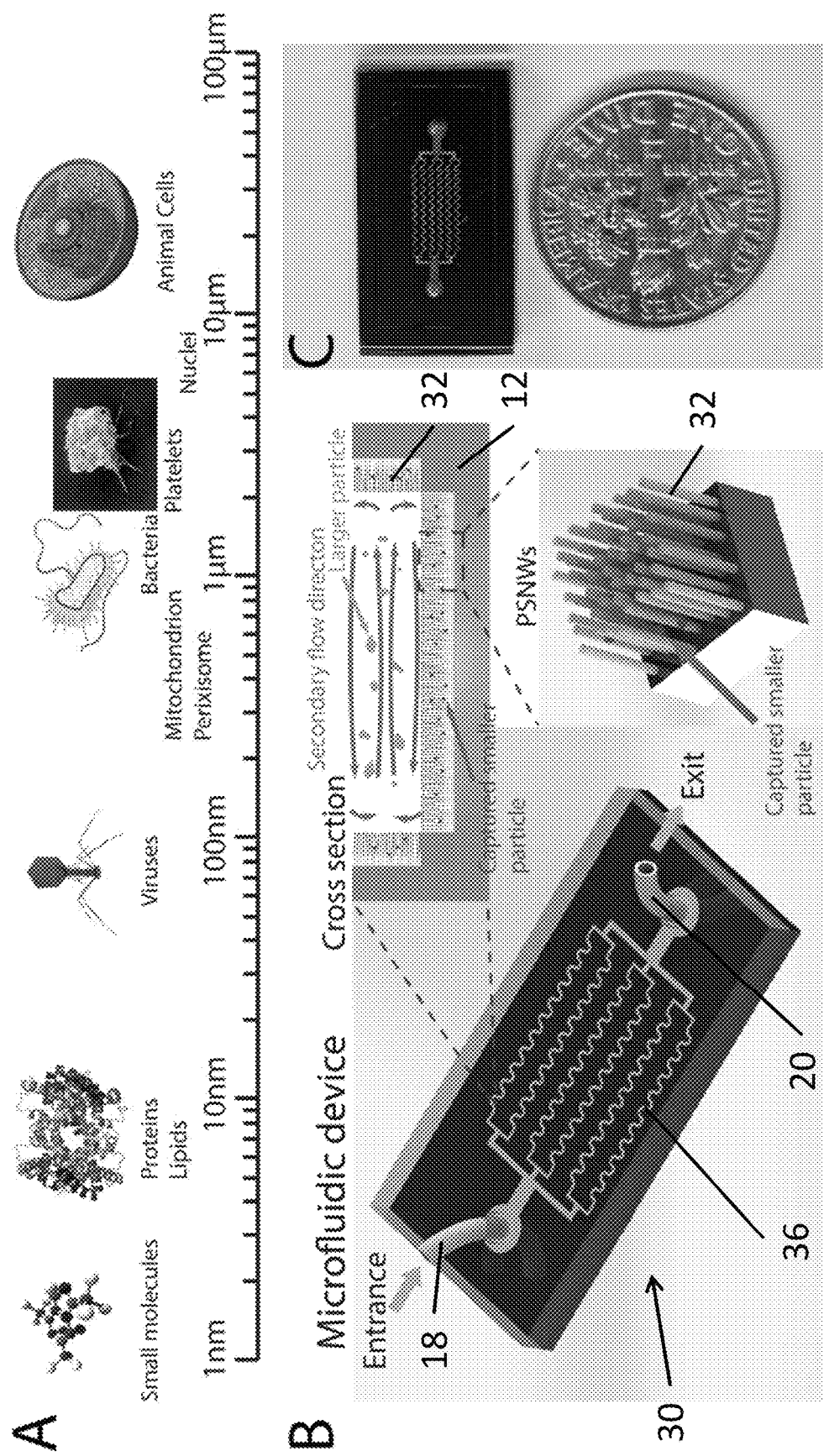
FIG. 2A through FIG. 2C depict the design and operation of the pSiNWs forest based device for viral isolation.
Figure 4:
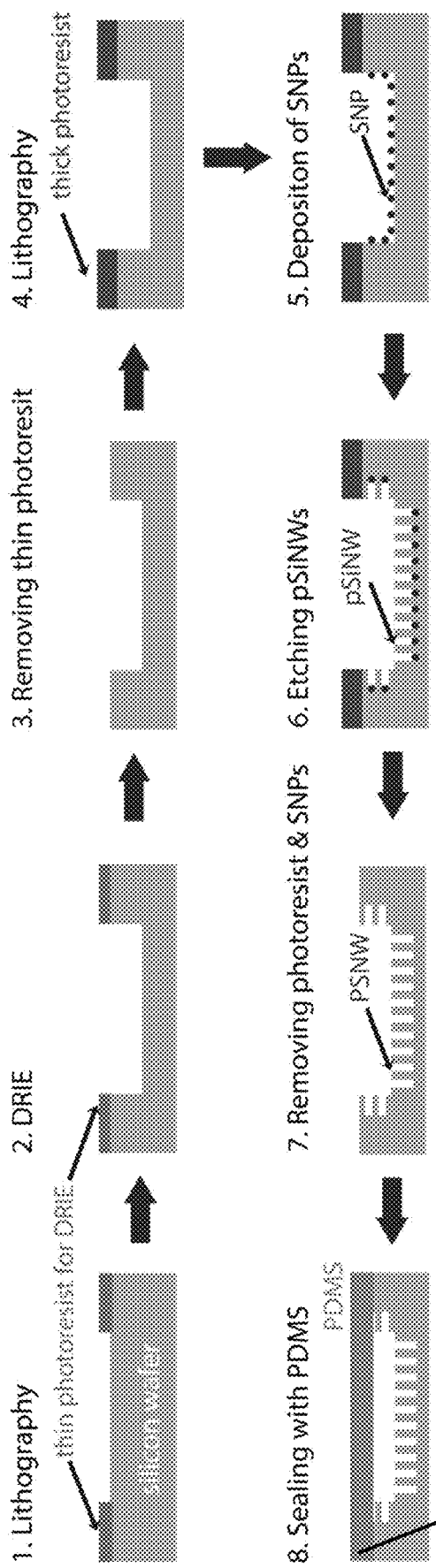
FIG. 4 depicts an exemplary fabrication process of the pSiNW microfluidic device. 1. Patterning photoresist SPR 3012 on high conductivity silicon wafer by photolithography. 2. Patterning microfluidic channels on the silicon wafer by DRIE with the SPR 3012 mask. 3. After DRIE, as SPR 3012 mask could not protect the surface of silicon as well as AZ p4620 during synthesizing pSiNWs (FIG. 5), SPR 3012 was replaced by AZ 4620. Removing photoresist SPR 3012 in nanostrip. 4. Protecting outside surface of channels by patterning thick photoresist AZ p4620 using photolithography. 5. Depositing SNPs on the bottom and side walls of the channels in the solution of 0.085% AgNO3 and 9.8% HF. 6. Etching pSiNWs forests with metal-assisted etching in the solution of 0.35% $H_2O_2$ and 9.8% HF; 7. Removing photoresist AZ 4620 in acetone and SNPs in the silver etchant; 8. Sealing the microfluidic channels with PDMS after surface treatment of silicon wafer and PDMS with oxygen plasma.

Referring now to FIG. 2B, one embodiment of a nanowire enrichment platform device 30 is depicted. Nanowire enrichment platform device 30 comprises substrate 12, nanowires 32, and cover 34 (FIG. 4). Substrate 12 can be any substrate known in the art, including, but not limited to, silicon, glass, metals, polymers, and the like.

Nanowires 32 are attached to substrate 12. Nanowires 32 can be made of any suitable material, including, but not limited to, silicon, zinc, zinc oxide, nickel, and the like. Further examples include: elemental semiconductor nanowires such as silicon and germanium; III-V compound semiconducting nanowires such as gallium arsenide, indium arsenide, and indium phosphide; II-VI semiconductor nanowires such as zinc sulfide, zinc selenide, cadmium sulfide, and cadmium selenide; metal semiconductor nanowires such as gold-silicon, and nickel-silicon; metal nanowires such as platinum, gold, aluminum, and iron; oxide nanowires such as zinc oxide, magnesium oxide, manganese dioxide, silicon dioxide, and titanium dioxide; sulfide nanowires such as copper sulfide, nickel sulfide, and iron sulfide; alloy nanowires such as cobalt-copper, iron-silver, and cobalt-silver; superconducting nanowires such as niobium nitride and yttrium barium copper oxide; and polymer nanowires such as polypyrrole and polyvinylpyrrolidone. In one embodiment, nanowires 32 comprise the same material as substrate 12. In some embodiments, nanowires 32 are uncoated. In other embodiments, nanowires 32 are provided with a coating. The nanowire coating can comprise any suitable coating, including, but not limited to: nickel, copper, silicon, aluminum, zinc, and the like. In one embodiment, the nanowire coating is enhances biocompatibility, such that the viability of captured particles is preserved.

Nanowires 32 comprise gaps between each nanowire. In one embodiment, the gap size is at least 1 nm. In various embodiments, the gap size is between 1 nm and 500 nm. In one embodiment, the gap size is dimensioned to fit the diameter of the particles to be captured. In various embodiments, the device comprises a plurality of nanowires 32 having different properties. For example, the nanowires 32 may have different gap sizes, different diameters, different thicknesses, and different densities. The device may also comprise a plurality of nanowires comprising different materials. The device may also comprise a plurality of nanowires having different coatings. Nanowires 32 and substrate 12 are enclosed by cover 34. Cover 34 may be made from any material, including, but not limited to, plastics, metals, glass, polymers, polydimethylsiloxane (PDMS), and the like. Cover 34 comprises at least one inlet 18 and at least one outlet 20 for ingress and egress of sample solution. In one embodiment, cover 34 is bonded to substrate 12 only. In another embodiment, cover 34 is bonded to substrate 12 and to nanowires 32. In one embodiment, cover 34 is removable.

In one embodiment, the nanowire enrichment platform device 30 is a microfluidic device. In another embodiment, the nanowire enrichment platform device 30 is a portable device wherein sample solutions are passed through by hand push.

Methods of Making

The invention provides methods for making the enrichment platform device. In one embodiment, the method is for making a VACNT enrichment platform device. In another embodiment, the method is for making a nanowire enrichment platform device.

In one embodiment, the method of making a VACNT enrichment platform device comprises bottom-up synthesis of CNT. An exemplary diagram is shown in FIG. 24. An iron-catalyst thin film is prepared on a substrate by e-beam evaporation and lift-off process and patterned using lithography. In various embodiments, additional catalyst materials are contemplated. Non-limiting examples of catalyst materials include nickel and cobalt. The pattern can be any pattern, including, but not limited to, a porous herringbone pattern, a droplet pattern, a spiral pattern, and the like. The CNT are synthesized through aerosol-assisted chemical vapor deposition (AACVD). The CNT synthesis method is not limited to AACVD; rather, the CNT synthesis method encompasses any CNT synthesis method known in the art. In certain embodiments of the method, at least a portion of the CNT is vertically aligned. In some embodiments, the all of the CNT are vertically aligned.

The method is amenable to making a plurality of CNT types, including, but not limited to: single-wall CNT, double-walled CNT, multi-wall CNT, and combinations thereof. In one embodiment, the CNT are doped. The CNT can be doped using any method known in the art, using any suitable material known in the art. For instance, non-limiting examples of materials the CNT can be doped with include nitrogen, boron, silicon, aluminum, phosphorus, and lithium. In one embodiment, the CNT are doped to enhance biocompatibility for maintaining the viability of captured particles.

In one embodiment, the gap size between the CNT is controlled by adjusting the thickness of the iron-catalyst layer. For instance, in one embodiment, increasing the thickness of the iron-catalyst layer correspondingly increases CNT gap size. In one embodiment, the CNT gap size is tunable to be in the range of 1-500 nm. In one embodiment, the diameter of the CNT is controlled by adjusting the thickness of the iron-catalyst layer. For instance, in one embodiment, increasing the thickness of the iron-catalyst layer correspondingly increases CNT diameter. In one embodiment, the density of the CNT is controlled by adjusting the thickness of the iron-catalyst layer. For instance, in one embodiment, increasing the thickness of the iron-catalyst layer correspondingly decreases CNT density.

The CNT are encased in a microfluidic device by bonding with a cover having at least one inlet and at least one outlet (FIG. 23A). In one embodiment, the cover is reversibly bonded. The cover may be made from any material, including, but not limited to, plastics, metals, glass, polymers, polydimethylsiloxane (PDMS), and the like.

In one embodiment, the method of making a nanowire enrichment platform device comprises deep reactive-ion etching (DRIE). An exemplary diagram is shown in FIG. 4. A thin photoresist layer is deposited on a substrate, such as silicon, and patterned using lithography. DRIE is used to create channels in the substrate where photoresist is not present. A thicker photoresist layer is deposited over existing photoresist, and silver nanoparticles (SNP) deposited. Silicon etching is performed by reacting with the SNP as a catalyst to form porous silicon nanowires (PSNW). In various embodiments, methods of etching commonly used in the art are also contemplated, including metal assisted silicon etching and wet etching.

In one embodiment, the gap size between the PSNW is controlled by adjusting SNP deposition time. For instance, in one embodiment, increasing SNP deposition time increases SNP size, which correspondingly increases PSNW gap size.

The SNP and photoresist is removed and the PSNW encased in a microfluidic device by bonding with a cover having at least one inlet and at least one outlet. In one embodiment, the cover is reversibly bonded. The cover may be made from any material, including, but not limited to, plastics, metals, glass, polymers, polydimethylsiloxane (PDMS), and the like.

Methods of Use

The invention provides methods of using the enrichment platform device for filtering particles, capturing particles, concentrating particles, and releasing viable particles. In one embodiment, the method removes particles from solution. In one embodiment, the method captures particles for analysis. In one embodiment, the method captures and releases viable particles for analysis.

In one embodiment, the invention provides a method of using the enrichment platform device to filter particles from solution. The gap size of the enrichment platform device can be tuned to capture particles that conventional filters cannot remove, such as in a water filter. Such particles can include viruses, bacteria, nanoparticles, nanobeads, nanoshards, and the like.

In one embodiment, the invention provides a method of using the enrichment platform to capture particles for analysis. The gap size of the enrichment platform device can be tuned to a specific size for the purpose of capturing known particles. For instance, if a virus has a known size range, the gap size of the enrichment platform can be tuned to capture particles of the known size. Passing a solution through the enrichment platform device will enable users to determine whether the solution contains particles of the known size. The particles can then be analyzed on the device for purposes such as identification, diagnosis, quantification, and the like. In one embodiment, the method uses a portable enrichment platform device. In one embodiment, the method uses sample volumes in the milliliter range. In one embodiment, the sample solutions are patient-derived solutions, including, but not limited to, blood, urine, saliva, and the like. In certain embodiments, the sample can comprise a solid such as tissue or stool. In certain embodiments, the sample can comprise a gas, such as a patient's breath, to capture air-borne pathogens. In various embodiments, the sample can be obtained from non-human sources, such as animals, plants, and insects.

In one embodiment, the invention provides a method of using the enrichment platform to capture and release particles while maintaining the viability of the particles. Particles can include, but are not limited to, viruses (such as plant viruses, human viruses, herpes, zika, hepatitis C, ebola), microorganisms and parasites (such as bacteria, amoeba, and plasmodium), and their various life stages. The gap size of the enrichment platform device can be tuned to a specific size for the purpose of capturing known particles. For instance, if a particle of interest has a known size range, the gap size of the enrichment platform can be tuned to capture particles of the known size range, such as in FIG. 22B. After a solution is passed through the enrichment platform device, the device cover is removed and the captured particles are released. The particles can be released by any method known in the art, including, but not limited to, scratching the device surface and degrading the device nanostructures.

By capturing particles according to size, the enrichment platform device also concentrates the population of captured particles. In some embodiments, the methods only require milliliters of sample solution to capture and isolate a volume of highly concentrated particles. The methods of the invention are also useful in providing concentrated particle samples to improve the performance of conventional detection schemes, including, but not limited to, RT-qPCR, next generation sequencing, and culture.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: A Porous Silicon Nanowire Forest Based Microfluidic Point-of-Care Device for Label-Free Isolation and Release of Viruses Viruses are infectious nanoscale agents which can infect all types of life forms, including animals, plants and bacteria. The spread of viral infections could have a significant negative impact on global health and economy (Binder, S. et al., Science 1999, 284 (5418): 1311-1313; Morens, D. M. et al., PLOS Pathog 2013, 9 (7): e1003467; Lederberg, J. et al., Microbial Threats to Health: Emergence, Detection, and Response. National Academies Press: 2003). They have caused some of the deadliest pandemics in recorded human history, including the 1918 influenza pandemic with an estimated 50 million deaths, the ongoing HIV/AIDS epidemic with 36 million deaths so far (Fauci, A. S. et al., New England Journal of Medicine 2012, 366 (5): 454-461), and the most recent Ebola outbreak resulting in 11306 deaths and 28196 reported cases as of September 2015 (W. H. O., Situation summary 2015, 3). Moreover, adaptation and changes in viruses, human demographics and behavior, environmental changes, technology and economic development, international travels, and global trades facilitate the rapid international spread of viral infections (Khan, K. et al., New England Journal of Medicine 2009, 361 (2): 212-214; Wilson, M. E., Journal of applied microbiology 2003, 94:1-11). Therefore, there is an urgent need for the development of techniques that can rapidly detect viruses and perform the surveillance of viral diseases almost anywhere.

A number of methods have been developed for viral detection, and the viral antigens, nucleic acids and serological antibodies are the core repertoire of techniques used for laboratory diagnosis of viral infections (Herring, A. J. et al., Journal of Clinical Microbiology 1982, 16 (3): 473-477; Lee, Y.-F. et al., Biosensors and Bioelectronics 2009, 25 (4): 745-752; Leland, D. S. et al., Clinical Microbiology Reviews 2007, 20 (1): 49-78; Yeh, Y.-T. et al., Annals of Biomedical Engineering 2014, 42 (11): 2333-2343). The detection of virus-specific IgM antibodies allows a diagnosis to be made from a single specimen and is uniquely useful for defining specific antiviral immunity. However, serology is frequently subject to high levels of off-target cross-reactions and may overlook acute infections as the immune system takes several weeks to produce relevant IgM antibodies. In contrast, the detections on the basis of viral nucleic acids and antigen can directly identify viruses in specimen allowing prompt diagnosis and emergency treatment, often within the same day, although the isolation and enrichment of viruses is a great challenge in the set-up given the extremely low virus levels in the early stage of viral infections. Generally, the virus isolation methods fall into two categories: biological methods and physical methods (Lee, Y.-F. et al., Biosensors and Bioelectronics 2009, 25 (4): 745-752; Kim, Y.-G. et al., Biosensors and Bioelectronics 2009, 25 (1): 253-258; Tam, P. D. et al., Journal of Immunological Methods 2009, 350 (1-2): 118-124). Biological methods use bioaffinities between antibodies and virus surface antigen to isolate viruses, in which the expression of known antigen and the availability of relevant antibodies must be simultaneously satisfied. These methods might face pitfalls in dealing with unknown or unidentified viruses. In addition, the detachment of isolated virus from antibodies functionalized surface while keeping viruses intact for subsequent analysis or culture poses another significant challenge. For example, after isolation the entire virus-antibodies complex rarely can infect living cells. Moreover, biological methods are usually labor intensive and require experienced personnel. The technical challenges in surface functionalization, including heterogeneous conjugation of antibodies and surface denaturation, also need to be addressed. In comparison, physical methods, including differential ultracentrifugation, dielectrophoresis, and filtration, mainly exploit differences in density, electrical affinity, and size between viruses and impurities (Reimer, C. B. et al., Science 1966, 152 (3727): 1379-1381; Collins, J. E. et al., Journal of Veterinary Diagnostic Investigation 1992, 4 (2): 117-126; Benfield, D. A. et al., Journal of Veterinary Diagnostic Investigation 1992, 4 (2): 127-133; Morgan, H. et al., Biophysical Journal 1999, 77 (1): 516-525; Green, N. G. et al., Journal of Biochemical and Biophysical Methods 1997, 35 (2): 89-102). They are label-free and virus-friendly, offering excellent flexibility in subsequent molecular analysis. Among these methods, size-based filtration is frequently used as most viruses have very unique size distribution spectrums, ranging from 20 nm to 400 nm (FIG. 2A) (Collins, J. E. et al., Journal of Veterinary Diagnostic Investigation 1992, 4 (2): 117-126; Benfield, D. A. et al., Journal of Veterinary Diagnostic Investigation 1992, 4 (2): 127-133; Yeh, Y. T. et al., Micro Electro Mechanical Systems (MEMS), IEEE 26th International Conference 20-24 Jan. 2013; pp 951-954; Patolsky, F. et al., Nat. Protocols 2006, 1 (4): 1711-1724; Yeh, Y. T. et al., SENSORS, IEEE, 1-4 Nov. 2015; pp 1-4; Xia, Y. et al., 18th International Conference on Solid-State Sensors, Actuators and Microsystems (TRANSDUCERS), 21-25 Jun. 2015; pp 444-447; Chen, G. D. et al., Small 2011, 7 (8): 1061-1067; Yeh, Y. T. et al., 18th International Conference on Solid-State Sensors, Actuators and Microsystems (TRANSDUCERS), 21-25 Jun. 2015; pp 747-750). Therefore, viruses can be differentiated from impurities, such as proteins, bacteria and mammalian cells, allowing size-based isolation. Additionally, in practical applications, the gap distance of a filter can be tuned to obstruct different viruses with varying sizes. Carbon nanotubes (CNT) and silicon nanowires have attracted special attention. Their light weight, high tensile strength, biocompatibility, tunable gap distance, and reliable production are particularly useful for isolating viruses by size (Yeh, Y. T. et al., Micro Electro Mechanical Systems (MEMS), IEEE 26th International Conference 20-24 Jan. 2013; pp 951-954; Patolsky, F. et al., Nat. Protocols 2006, 1 (4): 1711-1724; Yeh, Y. T. et al., SENSORS, IEEE, 1-4 November 2015; pp 1-4; Xia, Y. et al., 18th International Conference on Solid-State Sensors, Actuators and Microsystems (TRANSDUCERS), 21-25 Jun. 2015; pp 444-447; Chen, G. D. et al., Small 2011, 7 (8): 1061-1067; Yeh, Y. T. et al., 18th International Conference on Solid-State Sensors, Actuators and Microsystems (TRANSDUCERS), 21-25 Jun. 2015; pp 747-750; Wang, Z. et al., Lab on a Chip 2013, 13 (15): 2879-2882; Zhang, G.-J. et al., Analytica Chimica Acta 2012, 749:1-15). Recently, it was successfully demonstrated that the CNT forests with tunable gap distance can be used as filters to isolate viruses for propagation and sequencing (Yeh, Y. T. et al., 18th International Conference on Solid-State Sensors, Actuators and Microsystems (TRANSDUCERS), 21-25 Jun. 2015; pp 747-750). Silicon nanowires were frequently used in field effect transistors for label free viral detection (Patolsky, F. et al., Nat. Protocols 2006, 1 (4): 1711-1724; Zhang, G.-J. et al., Sensors and Actuators B: Chemical 2010, 146 (1): 138-144; Chen, K.-I. et al., Nano Today 2011, 6 (2): 131-154), but have never been explored for viral isolation.

The following study reports a novel porous silicon nanowires (pSiNWs) forest-based microfluidic point-of-care (POC) device for isolating and releasing viruses. The POC device has the dimensions 22 mm×10 mm×3 mm. The pSiNWs forest with well controlled inter-wire space was prepared by metal-assisted wet etching within curved channels (FIG. 2B). In such a design, the curved channels introduce the circulation in the plane of the cross-section (Di Carlo, D. et al., Proceedings of the National Academy of Sciences 2007, 104 (48): 18892-18897; Hou, H. W. et al., Scientific Reports 2013, 3:1259; Karabacak, N. M. et al., Nat. Protocols 2014, 9 (3): 694-710), which can spontaneously bring viruses and impurities to the pSiNWs forest. Later, viruses in a certain size range can pass through the gaps and physically trapped inside the forest. Meanwhile, larger impurities can be directly excluded, and smaller ones can escape from forest in continuous fluidic flow. To further improve the isolation efficiency, the curvature and dimensions of channels were judiciously optimized, allowing this new POC device to efficiently filtrate viruses or nanoparticles in similar size. The results show that approximately 50% of influenza viruses can be isolated in 30 minutes. Moreover, the pSiNWs forest is biodegradable in physiological conditions attributed to the extensive porous surfaces (Anderson, S. H. C. et al., physica status solidi (a) 2003, 197 (2): 331-335; Chiappini, C. et al., Advanced Functional Materials 2010, 20 (14): 2231-2239), enabling the release and harvest of trapped viruses in 24 hours for further culture and molecular analysis. Together, combined with the portability, high isolation efficiency, large sample capacity, and unique viral release mechanism, this POC devices can provide much faster access to results at or near the sites of the patient care, discover unknown virus, and monitor infectious diseases.

The materials and methods are now described.

Materials 4 inch <1 0 0> prime silicon wafer with resistivity 0.001-0.005 Ω·cm (University Wafer, MA, USA). Positive photoresist SPR 3012, positive photoresist AZ P4620, 49% hydrofluoric acid, and 30% hydrogen peroxide (Penn State University Nanofab). 0.1 N silver nitrate solution (Acros Organics). 75 nm Fluoro-Max Dyed Green Aqueous Fluorescent Particles, 400 nm Fluoro-Max Dyed Green Aqueous Fluorescent Particles, goat anti-Mouse IgG (H+L) secondary antibody Alexa Fluor 488 conjugate (Thermo Scientific). Cy3-Streptavidin (Invitrogen). Bovine serum albumin (BSA) (Sigma). Polydimethylsiloxane (PDMS) (Dow Corning). 1×PBS (VWR). Filters with 450 nm (Celltreat scientific products) and 200 nm pore size (VWR). Qiagen Onestep RT-PCR Kit (Qiagen, Valencia, CA). RNase inhibitor murine (New England Biolabs. Inc., MA, USA). Primers for RT-qPCR. H5N2 avian influenza virus and Mouse anti-H5 antibody. 9-11 day old special-pathogen free embryonated chicken egg.

Fabrication of pSiNWs Forest-Embedded Microfluidic Devices

Figure 5A:
FIG. 5A and FIG. 5B depict the protective effects of SPR 3012 mask (FIG. 5A) and AZ P4620 mask (FIG. 5B) during synthesizing PSNWs (bar: 200 μm). When using SPR 3012 mask after DRIE etching, silicon surface outside the channels was damaged by the etching solution. While using AZ 4620 mask, silicon surface outside the channels was fine.
Figure 5B:
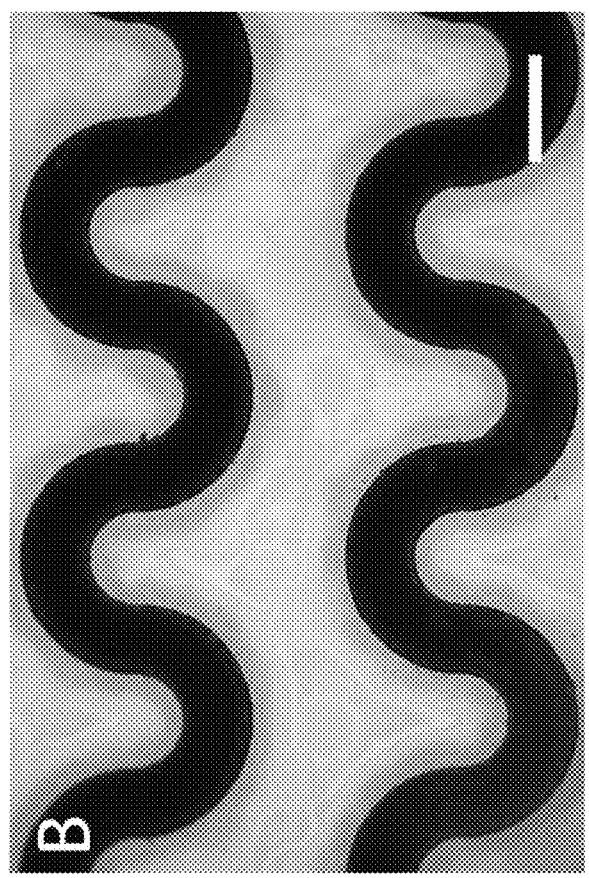

The fabrication process is illustrated in FIG. 4. A layer of positive photoresist SPR 3012 in 1.2 μm thickness was spin-coated on a silicon wafer with resistivity of 0.001-0.005 Ω·cm. Curved channels in 100 μm width with 100 μm internal curvature radius were patterned on the photoresist by photolithography followed by DRIE (Alcatel Speeder 100Si) to generate channels in various depth ranging from 20 to 60 μm. Afterwards, SPR 3012 was completely removed, and a layer of positive photoresist AZ P4620 in 15 μm thickness serving as a protective mask for wet etching was spin-coated and patterned (FIG. 5A and FIG. 5B). pSiNWs forest were prepared within channels by metal-assisted etching following the same protocol described previously (Hochbaum, A. I. et al., Nano Letters 2009, 9 (10): 3550-3554; Qu, Y. et al., Nano Letters 2009, 9 (12): 4539-4543). In brief, the wafer bearing channel patterns was immersed into the 0.085% $AgNO_3$ containing 9.8% HF for 10 to 90 sec at room temperature (RT) allowing deposition of silver nanoparticles (SNPs) to the bottom and sidewalls of the channels (Equation 1). Then, the wafer was transferred to the etchant bath containing 0.35% $H_2O_2$ and 9.8% HF for an hours at RT to prepare pSiNWS forests (Equation 2) (Wang, Z. et al., Lab on a Chip 2013, 13 (15): 2879-2882; Chiappini, C. et al., Advanced Functional Materials 2010, 20 (14): 2231-2239; Mohammad, Z. et al., Journal of Micromechanics and Microengineering 2011, 21 (6): 065006; Shiu, S.-C. et al., Applied Surface Science 2011, 257 (6): 1829-1834). Finally, after removing SNPs and photoresist AZ P4620 individual devices were diced from wafer and firmly bonded with a PDMS cover. (FIG. 2C).

$$4Ag^+ + Si + 6F^- \rightarrow 4Ag + [SiF_6]^{2-} \qquad \text{(Eqn. 1)}$$

$$2Ag + H_2O_2 + 2H^+ \rightarrow 2Ag^+ + 2H_2O \qquad \text{(Eqn. 2)}$$

Simulation of Flows in the Channels

Figures 6A, 6B, 6C, 6D:
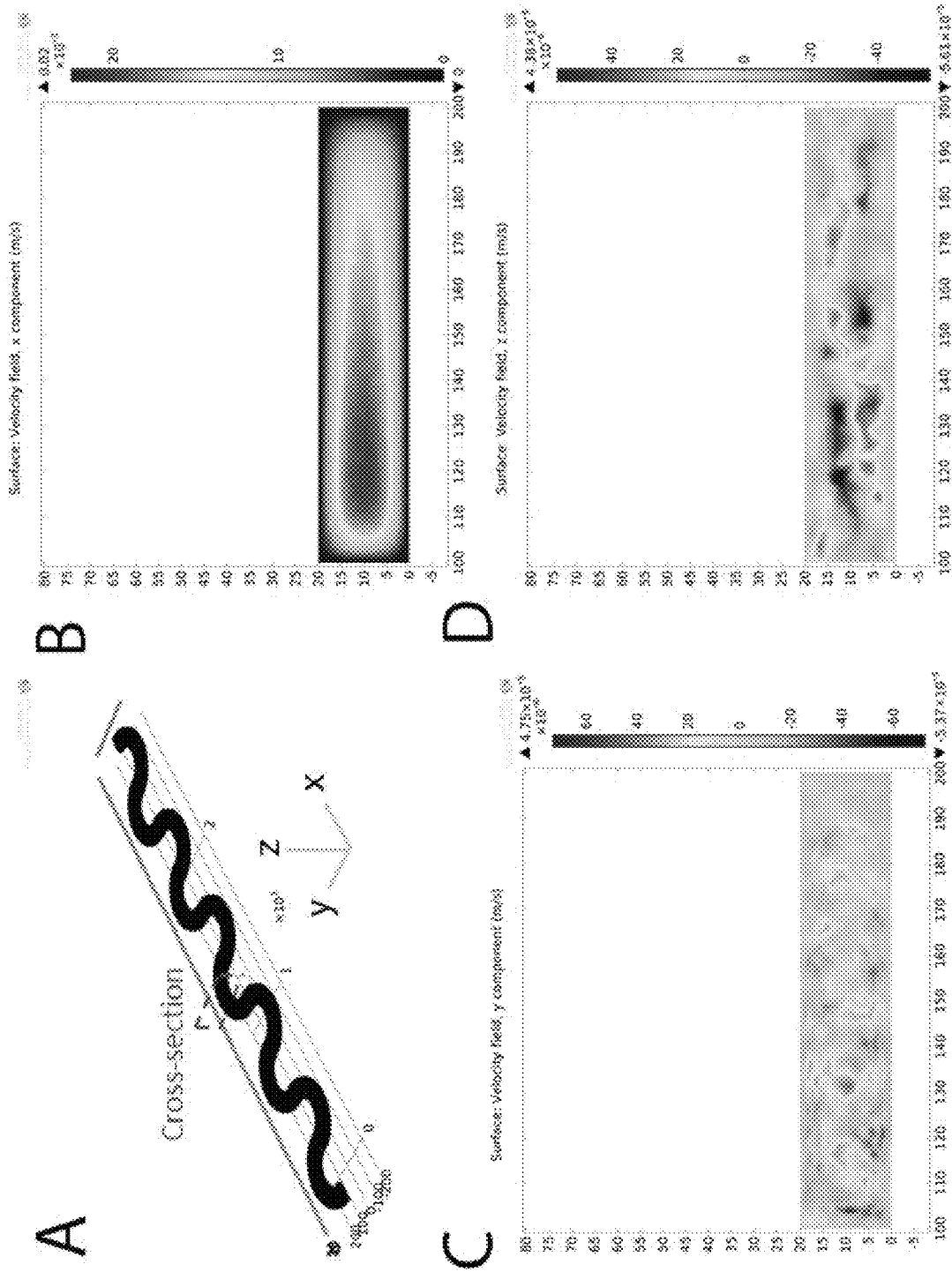
FIG. 6A through FIG. 6D depict fluid flow in the cross section (labeled box) of the 20 μm depth channels. The FEM model, which is a single channel with five repeatable units, was simulated in Comsol.
Figures 7A, 7B, 7C, 7D:
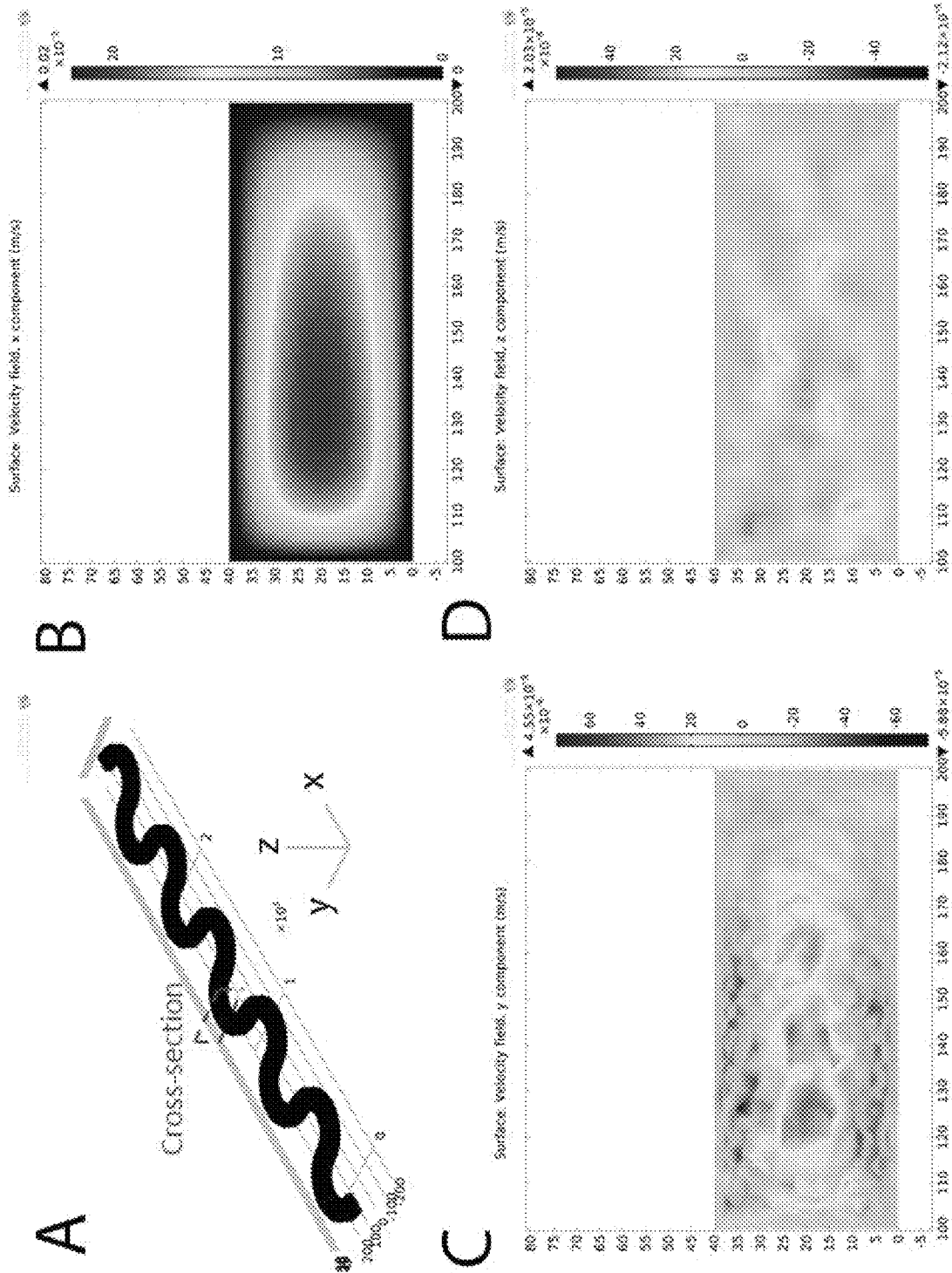
FIG. 7A through FIG. 7D depict fluid flow in the cross section (labeled box) of the 40 µm depth channels. The FEM model, which is a single channel with five repeatable units, was simulated in Comsol.

A finite element method (FEM) model was established to simulate the fluidic field inside the device by the software COMSOL. Laminar flow stationary study was chosen. A meandering channel with five periodic S shapes (FIG. 6A, FIG. 7A, FIG. 8A) was constructed to study the flow condition. In the inlet of the channel, the inflow condition was a normal inflow with a flow rate of 1.33 μl/min (8 μl/min in the device with 6 channels). In the outlet, the outflow conditions of normal flow and suppress backflow were set up. No slip condition was built on the walls. A physics-controlled finer mesh was chosen to produce meshes in the model. The results of velocities in x, y, z direction (FIG. 6A through FIG. 6D, FIG. 7A through FIG. 7D, FIG. 8A through FIG. 8D) were output to gain the streamlines in the cross section area of the channel. Capture efficiency (Equation 3) with different channel heights was also calculated by comparing fluorescence intensity of the mixture before they were injected into channels and after they were gathered in the outlet, respectively.

$$\text{Capture efficiency of nano beads} = 1 - \frac{FI_O}{FI_I} \times \frac{V_O}{V_I} \quad \text{(Eqn. 3)}$$

FI is the fluorescent intensity of nanobeads solution measured by the microplate. V is the volume of nanobeads. The subunits I, O, R are inflow, outflow and recovery solution, respectively.

Testing Capture Efficiency and Degradation During Device Optimization

All fluorescent images were taken by an Olympus IX 71 microscope equipped with a digital CMOS camera (C11440, Hamamatsu Photonics, Japan). Before injecting nanobeads or H5N2 virus solution, 1% BSA in 1×PBS was flowed through the device at 100 µl/min for 1 hour to prevent the non-specific absorption of nanobeads or virus in the channels. When testing the device with nanobeads, a 40 µl mixture of 75 nm and 400 nm nanobeads (the concentrations of both nanobeads in mixture were 375 µg/ml, blocked with 1% BSA) was injected into the device, followed by flowing through 210 µl DI water to wash channels. The outflow solution (containing both 40 µl beads mixture and 210 µl DI water) was gathered in the well of a 96 well plate to calculate the capture efficiency of nanobeads (Equation 3). To recover captured nanobeads, PBS solution continuously flow through the device for 24, 48, 72 hours at RT.

Testing Capture and Recovery Efficiency of H5N2 Virus

The effect of flow rate on capture efficiency of H5N2 virus was optimized first. 40 µl H5N2 virus solution was injected into the device at various flow rates ranging from 2 µl/min to 16 µl/min. After rinsing all channels with 1×PBS thoroughly, captured viruses were stained with primary antibodies (mouse IgG) targeting the H5 hemagglutinin on the virus surface and the secondary Alexa 488 labeled anti-mouse antibodies at RT for 45 min, respectively. After washing with 1×PBS thrice, three positions in the device were randomly selected for measurement of fluorescent intensity. To quantify capture efficiency of H5N2 virus, CT value of RT-qPCR was used to measure and compare the concentration of virus before injecting the device and after flowing through the device (Equation 4). To recover captured viruses, 1×PBS solution continuously flew through the device at RT for 24 hours. The recovery solution was gathered into a 1.5 ml centrifuge tube placing in an ice box. The concentration of recovered virus solution was compared to that of inflow virus solution to calculate the recovery efficiency (Equation 5).

$$\text{Capture efficiency of virus} = 1 - 2^{CT_I - CT_O} \times \frac{V_O}{V_I} \quad \text{(Eqn. 4)}$$

$$\text{Recovery efficiency of virus} = 2^{CT_I - CT_R} \times \frac{V_R}{V_I} \quad \text{(Eqn. 5)}$$

V is the volume of virus solution. CT is the CT value of the virus solution by RT-qPCR. The subunits I, O, R are inflow solution, outflow solution and recovery solution, respectively.

Real Time q-RCR

RT-qPCR of H5N2 influenza virus was conducted in a 25 µl reaction system by one-step RT-qPCR kit (Spackman, E. et al., Journal of Clinical Microbiology 2002, 40 (9): 3256-3260). The primers and probe specific to H5 subtype were used. The reaction mixture contains 5 µl 5× reaction buffer, 1 µl each of two primers (10 pmol/µl) and probe (5 pmol/µl), 1 µl dNTP mixture (10 mM each dNTP), 0.8 µl enzyme mixture, 2 µl RNA template, 13.7 µl RNase-free water and 0.5 µl RNase inhibitor (40 U/µl). The amplification and detection was performed in the 7300 Real time PCR system (Applied Biosystem Inc., Foster City, CA, USA). The thermal cycling profile of RT-qPCR was 50° C. for 30 minutes, 94° C. for 15 minutes and 45 cycles of denaturation at 95° C. for 10 seconds and annealing and elongation at 60° C. for 1 minutes. The data was collected and analyzed by 7300 real time PCR system software (7300 V1.4.0, Applied Biosystem Inc.) The cycle threshold (CT) value of each sample was calculated and compared to gain the capture and recovery efficiencies.

Propagation in Embryonated Chicken Egg and Hemagglutination Assay

200 µl released H5N2 influenza virus solution was inoculated and propagated in 9-11 day old special-pathogen free embroyonated chicken egg. The inoculated eggs were placed inside the incubator for 48 hours. Then the top of the egg was cracked open and the shell was peeled without breaking the shell membrane. Allantoic fluid was collected by a 3 ml sterile syringe with a 25G×⅝" needle. After centrifugation at 8000 rpm for 5 minutes, the supernatant containing propagated virus was filtered through 450 nm and 200 nm pore sizes filters sequentially. The hemagglutination assay (HA) was used to test infectious ability of recovered viruses. HA test was prepared with 0.5% chicken red blood cells (RBCs) (Hirst, G. K., The Journal of Experimental Medicine 1942, 75 (1): 49-64). The propagated virus solution was diluted into 2-fold serial and 50 µl of each dilution was added into different wells of a 96 well plate. Then, 50 µl 0.5% chicken RBCs was added into each well and incubated in 37° C. for 30 minutes. In the HA test, a negative result without virus appeared as a red dot in the center of the well bottom as the virus concentration was too low for RBC to settle. A positive result formed a uniform reddish suspension in the well. The concentration of virus was estimated by the dilution times of which the RBCs started to settle down.

The results are now described.

Fabrication of pSiNWs Forest-Based Microfluidic Devices

Figures 3A, 3B, 3C, 3D, 3E, 3F, 3G, 3H:
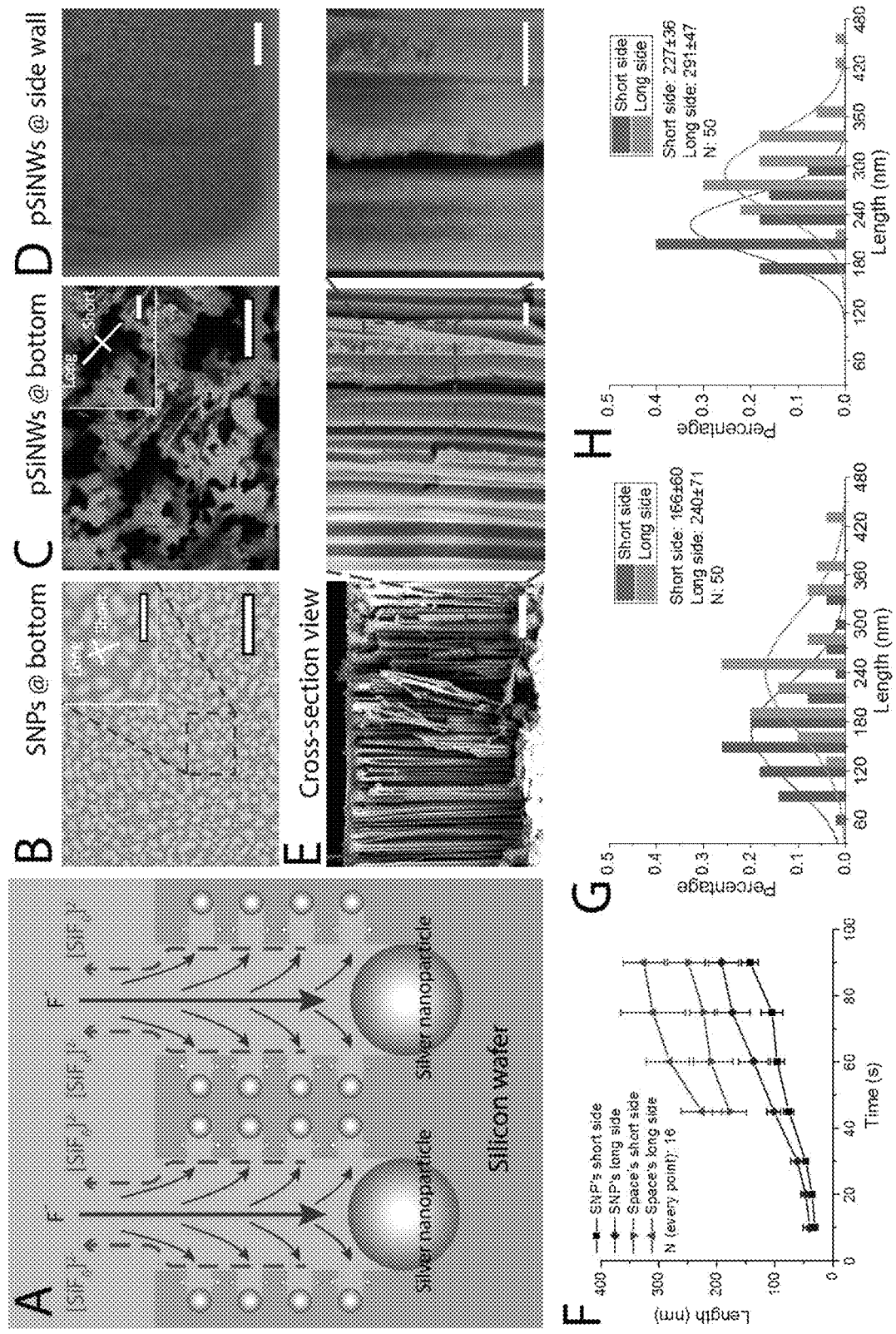
FIG. 3A through FIG. 3H depict the synthesis and characterization of pSiNWs.

For label-free size-based isolation of nanoparticles the inter-wire spacing between pSiNWs should be slightly larger allowing nanoparticles trapping within the pSiNWs forest. Therefore, the ideal inter-wise spacing was determined first. In metal-assist etching, SNPs server as catalyst and only silicon beneath SNPs can be effectively etched (FIG. 3A) indicating the size of SNPs after deposition directly determine the inter-wire spacing (FIG. 3B). In experiments, pSiNWs forest bearing inter-wire spacing was created on both sidewalls and bottom of channels (FIG. 3C, FIG. 3D), offering large surface area for isolating nanoparticles. In addition, after 1 hour HF etching at RT, the length of nanowires was ~10 µm (FIG. 3E). Mesopores in several nanometers were observed on each single nanowires (FIG. 3E). It was speculated that silver ions diffusing out the original SNPs can nucleate on nanowires at a certain concentration, extract electrons from the silicon nanowires, form new tiny SNPs, and catalyze the etching along the lateral direction of the nanowires (Qu, Y. et al., Nanoscale 2011, 3 (10): 4060-4068). It was found that by adjusting the deposition time ranging from 45 s to 90 s, the average size of SNPs clusters increased from approximately 75 nm×100 nm to 140 nm×190 nm (FIG. 3B, FIG. 3F). Accordingly, after wet etching the average size of inter-wire spacing increased from about 180 nm×230 nm to 250 nm×330 nm (FIG. 3C, FIG. 3F). As the size of influenza A viruses used in this study were approximately 80 to 120 nm (Lamb, R. A. et al., Annual Review of Biochemistry 1983, 52 (1): 467-

506), the inter-wire spacing had to be kept slightly larger than 120 nm which would require 45 s to 60 s for deposition of SNPs (FIG. 3F). To determine the ideal deposition time, 50 inter-wire spacing were randomly selected and measured in respective group (FIG. 3G, FIG. 3H). The results clearly show over 30% of the inter-wire spacing is smaller than 120 nm if the deposition time is shortened to 45 s. In contrast, with 60 s deposition, almost all inter-wire spacing is larger than the threshold value (FIG. 3H), and the average inter-wire spacing is about 227 nm×291 nm (FIG. 3G). Such spacing distribution would allow viruses to enter into pSiNWs forest and trap them within the forest. On the other hand, microparticles, such as bacteria and platelets, are unable to cross the relatively narrow gap or deeply enter into pSiNWs forest. On the contrary, other nanoparticles, e.g. serum proteins, are much smaller and can easily enter and escape from the forest. Thus, deposition time of 60 seconds was used to prepare pSiNWs forest for isolating virus influenza A.

Optimization of Performance of pSiNWs Embedded Microfluidic Devices Using Nanobeads In flow through curved channel geometries, curvature amplifies a lateral instability that drives a secondary cross-sectional flow field, known as Dean flow, characterized by the presence of two counter-rotating vortices located above and below the horizontal plane of symmetry of the channel (Di Carlo, D., Lab on a Chip 2009, 9 (21): 3038-3046). Inertial focusing of spherical microparticles with diameters ranging between 5 and 20 µm has demonstrated the promise of efficient separation as well as increased throughput (Di Carlo, D. et al., Proceedings of the National Academy of Sciences 2007, 104 (48): 18892-18897; Hou, H. W. et al., Scientific Reports 2013, 3:1259; Karabacak, N. M. et al., Nat. Protocols 2014, 9 (3): 694-710). To date, the Dean flow-based technique has not been reported with nanoparticles. In the present design, viruses are expected to be brought into pSiNWs forest by vortices generated in the channels, and thus the odds of trapping viruses inside the forest can be improved. Moreover, in the flow the wall lift force pushing viruses against walls was smaller than the opposite Dean force in several orders of magnitude (FIG. 9) (Di Carlo, D., Lab on a Chip 2009, 9 (21): 3038-3046; Matas, J.-P. et al., Journal of Fluid Mechanics 2009, 621: 59-67; Martel, J. M. et al., Scientific Reports 2013, 3:3340). It will also guide viruses through inter-wise spacing to pSiNWs forest, and trap them inside. Given that the curvature of channels is fixed, it was hypothesized that vortices that can efficiently bring viruses to pSiNWs forest could be generated by optimizing channel height and flow rate. To study the effect of channel height on Dean flow in the cross-sectional plane, a FEM model was established to simulate the fluidic field inside the channel. It was found that the intensity (FIG. 6A through FIG. 6D, FIG. 7A through FIG. 7D, FIG. 8A through FIG. 8D) and position of local vortices (FIG. 10A through FIG. 10C) significantly changed in three groups. Relatively more local vortices near the channel wall were observed in the curved channels with 20 µm height in comparison with that in the rest of the two groups, and thus it was speculated that more viruses would be brought into the pSiNWs forest in channels with relatively lower height. Further, the height effect on capture efficiency (Equation 3) was experimentally investigated using fluorescence labeled nanobeads. Green or blue fluorescence labeled nanobeads in 75 nm and 400 nm sizes mimicking influenza A viruses and impurities in body fluid, respectively, were used for testing. When the channel height decreased from 60 µm to 20 µm, at 8 µl/min the capture efficiency of 75 nm nanobeads increased from 6.4% to 14.1%, while that of the 400 nm nanobeads was approximately 4% in all groups (FIG. 10D). Together, the height optimized from experiments was consistent with simulation outcome, and thus channels with 20 µm height were prepared for the following optimization.

To study capture specificity, a 40 µl mixture of nanobeads in 75 nm and 400 nm size, respectively, were injected into channels with 20 µm height at a flow rate of 8 µl/min followed by thoroughly rinsing with DI water. As the inter-wire spacing of the pSiNWs was approximately 250 nm, it was expected that 75 nm nanobeads would be isolated and trapped, while 400 nm nanobeads would be size excluded. After isolation, the green fluorescence from the channel with 20 µm height flowing 75 nm nanobeads was much stronger than that of the original beads flow and pSiNWs background (FIG. 10E), indicating that 75 nm nanobeads were efficiently captured and trapped inside the pSiNWs. On the contrary, the blue fluorescence from 400 nm nanobeads was extremely weak and very close to the pSiNWs background (FIG. 10F), demonstrating that the pSiNWs forests could barely capture 400 nm nanobeads. The SEM image further validated that many 75 nm nanobeads and very few 400 nm nanobeads were captured and tapped inside the pSiNWs forests (FIG. 10G, in circles). The above experimental results prove that the pSiNWs forest with ~250 nm inter-wires spacing in curved channels with 20 µm height can effectively and specifically isolate 75 nm nanobeads.

In addition to channel height, flow rate can also affect the capture efficiency of viruses. In general, high flow rate is preferred as it can significantly shorten sample processing time and increase sample capacity. However, in the present design, the nanoparticle-pSiNWs forest interactions might be impaired, which accordingly might decease the capture efficiency of nanobeads. On the contrary, strong local vortices might not form at low flow rate, although relatively low flow rate can ensure the full contact and interactions between nanoparticle and pSiNWs forest. Therefore, to study the effect of flow rate on the capture efficiency of 75 nm and 400 nm nanobeads, respectively, flow rates ranging from 2 µl/min to 16 µl/min were tested. As shown in FIG. 10H, the capture efficiency of 75 nm nanobeads reaches the maximal value of 14.1% at 8 µl/min. When the flow rate is slower than 8 µl/min, capture efficiency of 75 nm nanobeads can be gradually improved by increasing flow rate. At relatively low flow rate, local vortices of fluid flow could be strengthened by increased flow rate, and thus could effectively bring nanobeads into pSiNWs forest. However, once the flow rate reaches or surpasses 12 µl/min the capture efficiency of 75 nm nanobeads decreases significantly. As a result, at relatively high flow rates, nanobeads might not have sufficient time to pass through inter-wire spacing to be trapped before coming out from the device outlet. In the control group using 400 nm nanobeads, which barely got trapped inside the pSiNWs forest, the capture efficiency slightly fluctuates between 2% and 4.5% (FIG. 10H).

In a cyclic iteration application, a sample might be run for multiple times over the device to increase the capture efficiency (Wan, Y. et al., Cancer Research 2010, 70 (22): 9371-9380). This strategy has been widely used to isolate rare molecules. In a previous study, it was found that after a single run, green fluorescence from 75 nm nanobeads in the curved channels displayed random non-uniform distribution (FIG. 10C), indicating there were still considerable empty spacing inside the pSiNWs forest for trapping 75 nm nanobeads. Hence, it was speculated that the capture efficiency of 75 nanobeads could be significantly improved by increasing cycle times. In the following experiment, the nanobeads suspension was recollected from the device outlet and reinjected into the device for up to 5 times. The capture efficiency of 75 nm nanobeads significantly increased from 14.1% to 37.6% after the fifth recycling. In contrast, the capture efficiency of 400 nm nanobeads was only slightly increased from 4.5% to 12.9% (FIG. 10I).

Compared to solid silicon nanowire, pSiNWs have been demonstrated to be biodegradable in alkaline solution including PBS due to its mesopores at nanoscale (Equation 6) (Anderson, S. H. C. et al., physica status solidi (a) 2003, 197 (2): 331-335). However, they cannot be degraded in DI water (Anderson, S. H. C. et al., physica status solidi (a) 2003, 197 (2): 331-335). The degradation of pSiNWs will allow captured and trapped nanobeads to escape from the forest. 1×PBS continuously flows through the pSiNWs embedded microfluidic device for 24, 48 and 72 hours at RT, respectively, and the appearance of pSiNWs forest at each timepoint are shown in FIG. 11A and FIG. 11B. SEM images reveal that the degree of corrosion is dependent on time, and pSiNWs forest totally degraded at the 72 hour timepoint. The feasibility of releasing captured 75 nm nanobeads was tested. After continuous flushing within 1×PBS for 24 hours, green fluorescence are barely detectable (FIG. 11C), indicating trapped 75 nm nanobeads escaped from the forest and flowed out of the channels. The extended flushing did not significantly improve the releasing efficiency, and thus 24 hours was chosen for the following experiments. While flushing within DI water in the control group, green fluorescence remained similar to that of 0 hour (FIG. 12C), indicating nanobeads trapped in the pSiNWs forest will not be flushed out by flow only. It was noted that after release of captured 75 nm nanobeads with 1×PBS, the recovery efficiency of nanobeads was not investigated as their concentrations in PBS was too low to be detected by a microplate reader.

$$Si + 2OH^- + 4H_2O \rightarrow Si(OH)_2^{2+} + 2H_2 + 4OH^- \quad \text{(Eqn. 6)}$$

Capture and Release of Influenza Virus Using pSiNWs Forest Embedded Microfluidic Device After optimizing operation parameters using nanobeads, the pSiNWs forest embedded microfluidic device was used to capture H5N2 avian influenza viruses, and an in situ immunofluorescence assay was used to detect the captured viruses (FIG. 12A through FIG. 12C). The time-scale of pSiNWs degradation in 1×PBS solution was hours, while the whole capture process takes only 30 min. Therefore it is safe to suspend viruses into 1×PBS for capturing (Wang, Z. et al., Lab on a Chip 2013, 13 (15): 2879-2882; Chiappini, C. et al., Advanced Functional Materials 2010, 20 (14): 2231-2239). For the experimental group, 40 μl of H5N2 virus suspension was injected into the device under various flow rates ranging from 2 μl/min to 16 μl/min with 3 cycles. Similar to the capture efficiency of 75 nm nanobeads as they have very close size distributions, the highest capture efficiency of H5N2 was also achieved at 8 μl/min (FIG. 12D). The fluorescence intensity was approximately 2.5 times higher than that in the negative control group which contained no viruses (FIG. 12A and FIG. 12B). SEM images also demonstrated H5N2 viruses were captured and trapped inside the pSiNWs forest (FIG. 12C). To further quantitatively determine the capture efficiency of viruses, respective CT values of each group were measured on the basis of RT-qPCR results, and the capture efficiency of viruses was determined using the device was 48±4% (FIG. 12E, FIG. 13).

FIG. 13, comprising FIG. 13A and FIG. 13B, depicts the results of experiments demonstrating virus capture and analysis by carbon nanotube-size tunable enrichment platform (CNT-STEP). (FIG. 13A) Schematic illustration showing the design and operation of CNT-STEP. A swab sample containing viruses (red spheres) is collected from a bird (1). As the virus suspension generated from the swab sample flows through CNT-STEP, the viruses are captured within the sidewall of the droplet-shaped microfluidic chamber made of CNT forest (2). The CNT forest traps virions with size similar to CNT gap size. After capture, the virus is enriched inside CNT forest and can be characterized by various methods (3). (FIG. 13B) Images with increasing magnifications of CNT-STEP before PDMS bonding. Brightfield microscopy image showing top view of the droplet-shaped CNT microfluidic chamber on silicon substrate (1). SEM image of CNT porous microfluidic sidewall in a tilted view (2). High magnification SEM image showing side view of CNT forest structure (3). TEM image of a single aerosol-assisted chemical vapor deposition (AACVD) synthesized CNT (4). Scale bars in (B) 1-4 are 2 mm, 50 μm, 50 nm, and 10 nm, respectively.

FIG. 14, comprising FIG. 14A through FIG. 14D, depicts the results of experiments demonstration the characterization of the growth, geometry, and size-tunable filtration properties of the CNT-STEP. (FIG. 14A) Diameter and (FIG. 14B) density of the iron nanoparticles (red) and CNT (black) as functions of the thickness of the iron catalyst thin films (1 nm, 3 nm, 6.5 nm, 9.5 nm, and 12 nm, n=8 each). Iron nanoparticles were formed during temperature ramping phase (from room temperature to 825° C. in 30 minutes duration) before the CNT synthesis. The diameter and density were measured from SEM images. (FIG. 14C) Calculated the gap size of the CNT structures from the measured densities and diameters. The inset illustrates the square geometry model used for the calculation, where CNT-to-CNT distance (G) and diameter of CNT (D) are constants. (FIG. 14D) Measured size-tunable filtration characteristics of CNT-STEP with various gap sizes of 25 nm, 85 nm, and 280 nm. Small molecule fluorescein and fluorescent polystyrene nanospheres of 20 nm, 50 nm, 100 nm, 140 nm, 400 nm, and 1000 nm in diameter were used. Penetration ratio is defined as the ratio of the fluorescence intensity of the filtrate to that of the original suspension (n=8).

FIG. 15, comprising FIG. 15A through FIG. 15G, depicts the results of experiments demonstrating H5N2 avian influenza virus (AIV) captured and detected by the CNT-STEP microdevice. (FIG. 15A) Fluorescence microscope images of on-chip IFA of H5N2 AIV inside the CNT-STEP microdevices with 25 nm, 85 nm, and 280 nm gap sizes. Red arrows indicate the flow direction. (FIG. 15B) RT-qPCR curves of H5N2 ($10^5$ $ELD_{50}$ titration) trapped and extracted from 25 nm, 85 nm, and 280 nm gap size device after filtration. (FIG. 15C) SEM images of the H5N2 AIV virions trapped inside the CNT forest structure of 25 nm gap size (the flow direction is into the plane), with inset at a higher magnification (scale bars: 200 nm). (FIG. 15D) TEM images of H5N2 AIV around MWCNTs after the CNT structures were scraped from the microdevice, with inset showing the individual virion at a higher magnification (scale bars: 200 nm). (FIG. 15E) RT-qPCR plots of H5N2 AIV samples of 0.1 $ELD_{50}$ titration after enrichment and 1 and 10 $ELD_{50}$ titrations before enrichment (n=6). (FIG. 15F) Pie charts presenting the percentage distribution of NGS reads generated by blast search before and after microdevice enrichment. (FIG. 15G) Circos plot of assembled H5N2 contigs generated by NGS from the CNT-STEP microdevice enriched sample. Track 1 (outermost): Reference strain "A/mallard/ Wisconsin/411/1981 (H5N2)" (the closest strain of H5N2 by blast search). Track 2: Variants with color coding (deletion: long black line; transitions: A-G: fluorescent green, G-A: dark green, C-T: dark red, T-C: light red; transversion: A-C: brown, C-A: purple, A-T: dark blue, T-A: fluorescent blue, G-T: dark orange, T-G: violet, C-G: yellow, G-C: light violet). Track 3: Open reading frame (green). Track 4: Location of AIV detection by Sanger's method targeting the NP gene (713~1463 bp). Track 5: Coverage depth at each genomic position (black) (scale of the plot from 0 to 30k reads). Track 6: Contigs generated by developed pipeline de-novo assembly (grey). Inset is a TEM picture of the virus.

FIG. 16 depicts the setup of aerosol assisted chemical vapor deposition (AACVD) for CNT synthesis. Top image: Image of AACVD setup inside a fume hood. Bottom image: Schematic illustration of AACVD for the CNT synthesis.

Afterwards, after 24 hours continuously flushing with 1×PBS, the green fluorescence intensity was only ~10% of that before flushing. In the control group, DI water which cannot dissolve pSiNWs was used, and the green fluorescence intensity only decreased to ~80% after 24 hours flushing (FIG. 14A). This result indicated that captured viruses were released by degradation of pSiNWs forest and then flushed out in PBS flow. In contrast, simply flushing using DI water which has insignificant effect on degradation of pSiNWs is inefficient to directly remove trapped viruses from pSiNWs forest. The released viruses in PBS were recollected for further identification and culture. Sandwich ELISA-like virus identification was performed first. Released viruses were enriched with H5 antibody-conjugated magnetic beads (FIG. 15A through FIG. 15C) and stained with red fluorescence labeled H5 antibodies for viral identification. Red fluorescence intensity in experimental group was ~2 times higher than that of negative control group containing pSiNWs degradation solution only without any viruses, indicating released viruses can be successfully recollected for identification. To determine the recovery efficiency, CT values of RT-qPCR results were used to quantify viral concentration in the releasing solution (Equation 5, FIG. 14B, FIG. 16). It was found the recovery efficiency was 29±7% in releasing solutions with varying volume ranging from 60 µl to 1000 µl. So about 60% of captured viruses could be recovered and recollected. In recovery sample A, the CT value was 16.8±0.6. After conversion, virus titer was ~6×10$^6$ EID$_{50}$/ml. Such high concentration would satisfy the following virus cultivation if viruses are alive. To test the viability, released viruses were inoculated into embryonated chicken eggs for cultivation, and HA test was used to quantify the relative concentration of harvested virus solution. After being diluted 2$^{10}$ times, virus suspension failed to agglutinate the red blood cells, and RBCs began to settle out of suspension forming red precipitation. Thus the titer of the virus sample was determined to be 1:2$^9$, which is ~4×10$^6$ EID$_{50}$/ml (The CT value of virus sample was 1:2$^{10}$ was 16.45) (FIG. 14C). The findings demonstrated that by propagating these viable viruses after capture and release cycles, large amounts of viruses could be obtained for various subsequent virus-related studies.

In conclusion, a pSiNWs forest embedded microfluidic POC device was successfully developed for label-free capture and release of viruses. For the first time it was demonstrated that targets at nanoscale can be physically trapped into inter-wire spacing with tunable distance with Dean flow in curved channels. Approximately 50% of viruses can be physically captured and trapped in pSiNWs forest after only 3 iterative cycles at as high as 8 µl/min flow rate. Viruses remain viable after 24 hours and can be released through the degradation of the pSiNWs forest. The recovery efficiency is approaching 29% of total inducing virus. Moreover, it was also demonstrated that released viruses can be lysed for RT-qPCR or further cultivated with embryonated chicken eggs. With this POC device, viruses with specific sizes could be isolated in 30 minutes and recovered by dissolving pSiNWs in PBS for another 24 hours. Recovered viruses are alive and can be further cultivated with embryonated chicken eggs for further long term analysis, like gene mutation detection, drug testing.

Example 2: A VACNT Integrated Handheld Device for Label-Free Virus Capture, Detection, and Enrichment for Genomic Analysis A handheld (1 cm×2 cm) vertically aligned carbon nanotube (VACNT) integrated microfluidic device is presented herein to capture virus by nanoscale filtration. The device contains porous herringbone array made of VACNT with a tunable gap size (20-550 nm) on a fused silica substrate. Avian influenza virus (AIV) H5N2 subtype was isolated from chicken swab samples and detected by on-chip immunofluorescence staining. The device enriched the H5N2 from swab samples and improved the RT-qPCR detection limit by at least one order of magnitude, confirmed by SEM and gel electrophoresis. Finally, the isolated H5N2 was successfully cultured ex vivo inside chicken eggs.

Figure 17A:
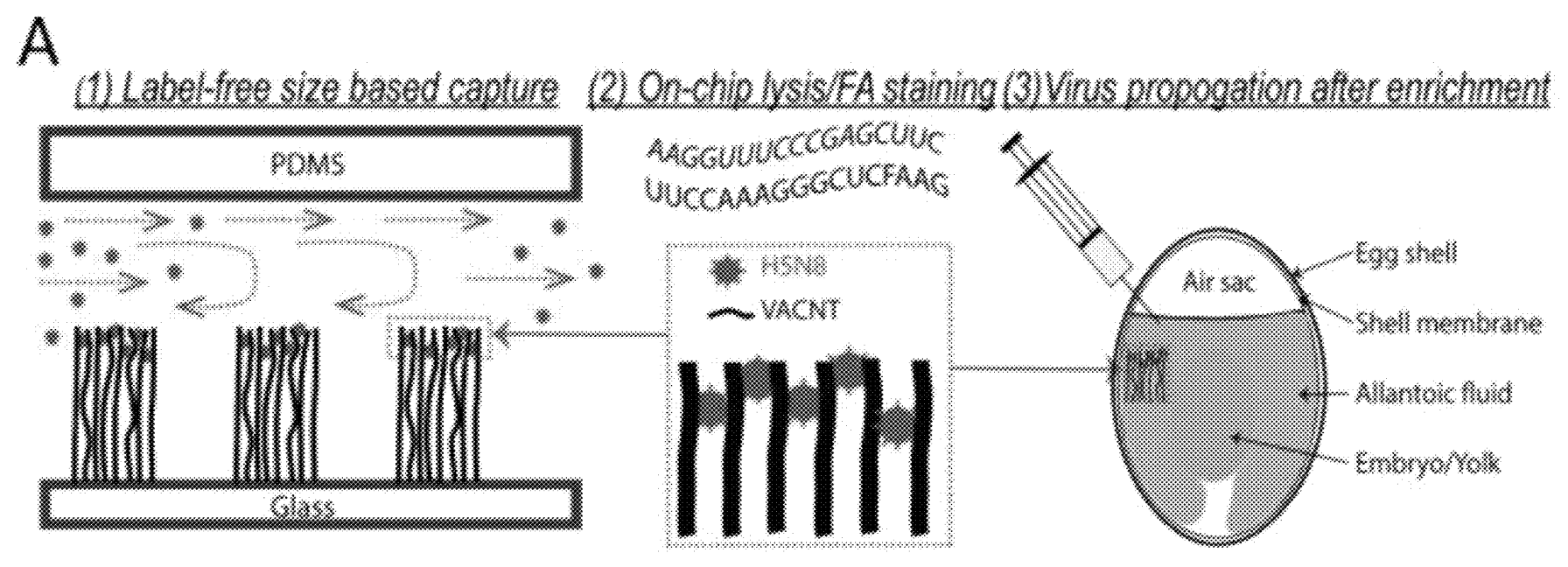

FIG. 17 depicts the results of experiments demonstrating the temperature profile of the furnaces during the CNT synthesis. The devices were loaded at the center region (~3 inches in length) of the 2$^{nd}$ furnaces.

Figure 17B:
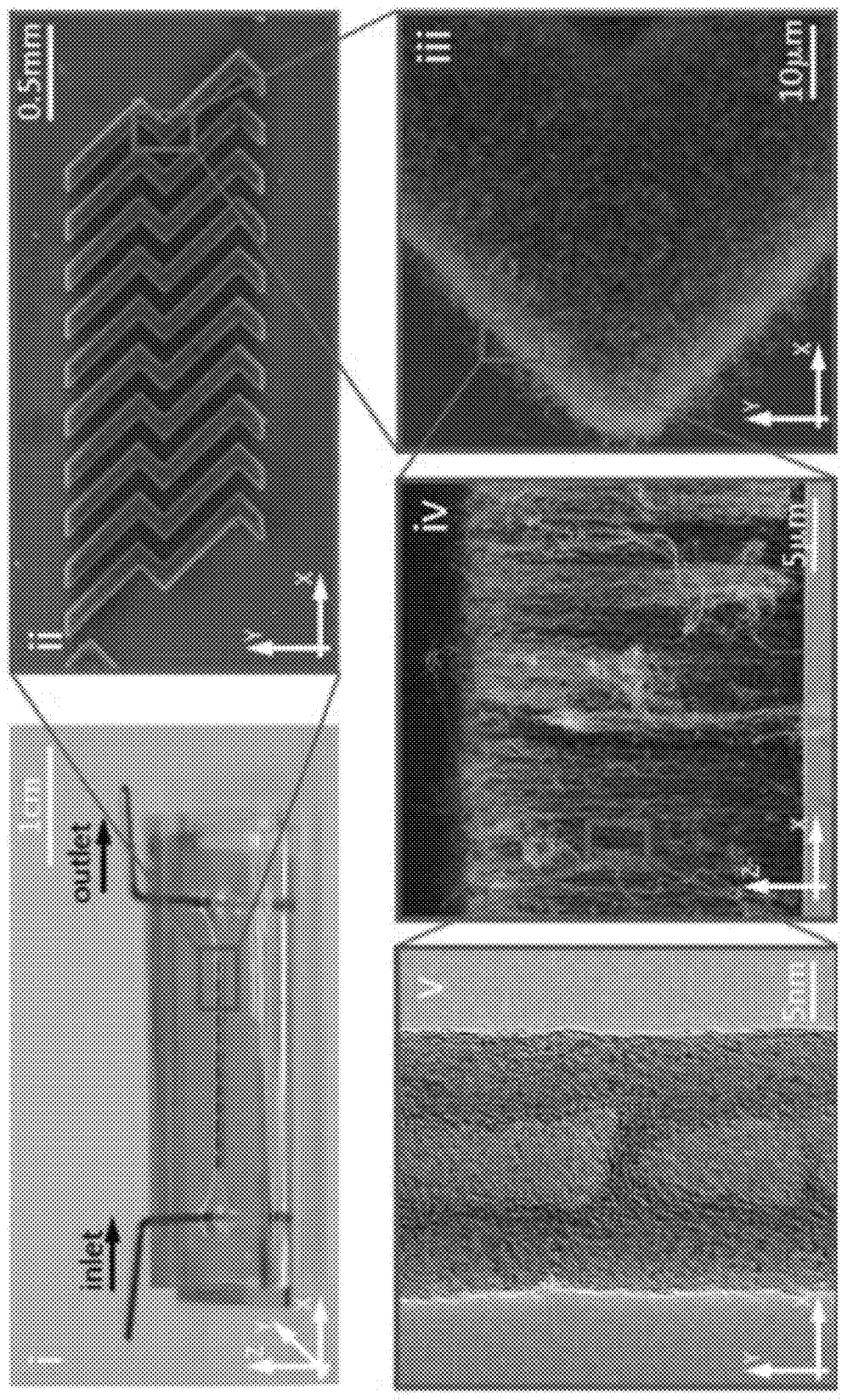

VACNT was synthesized by aerosol-based chemical vapor deposition (CVD) on a lithography-patterned iron-catalyst thin film to form a porous herringbone array with 50 µm in height (FIG. 17A) (Stroock et al., Science, 2002, 295:647-651). The porous structure captured virus with diameter similar to VACNT gap size during the enhanced mixing process. After virus was captured, immunofluorescence or RNA extraction after on-chip virus lysis could be performed on-chip. Furthermore, the enriched H5N2 was collected by scratching the VACNT forest structure with a pipette tip and directly inoculated into chicken eggs for ex vivo culture. Optical, SEM, and TEM images demonstrated the assembled device with vertically aligned CNT structure selectively grew on fused silica substrate at different scales (FIG. 17B).

Figures 18A, 18B, 18C:
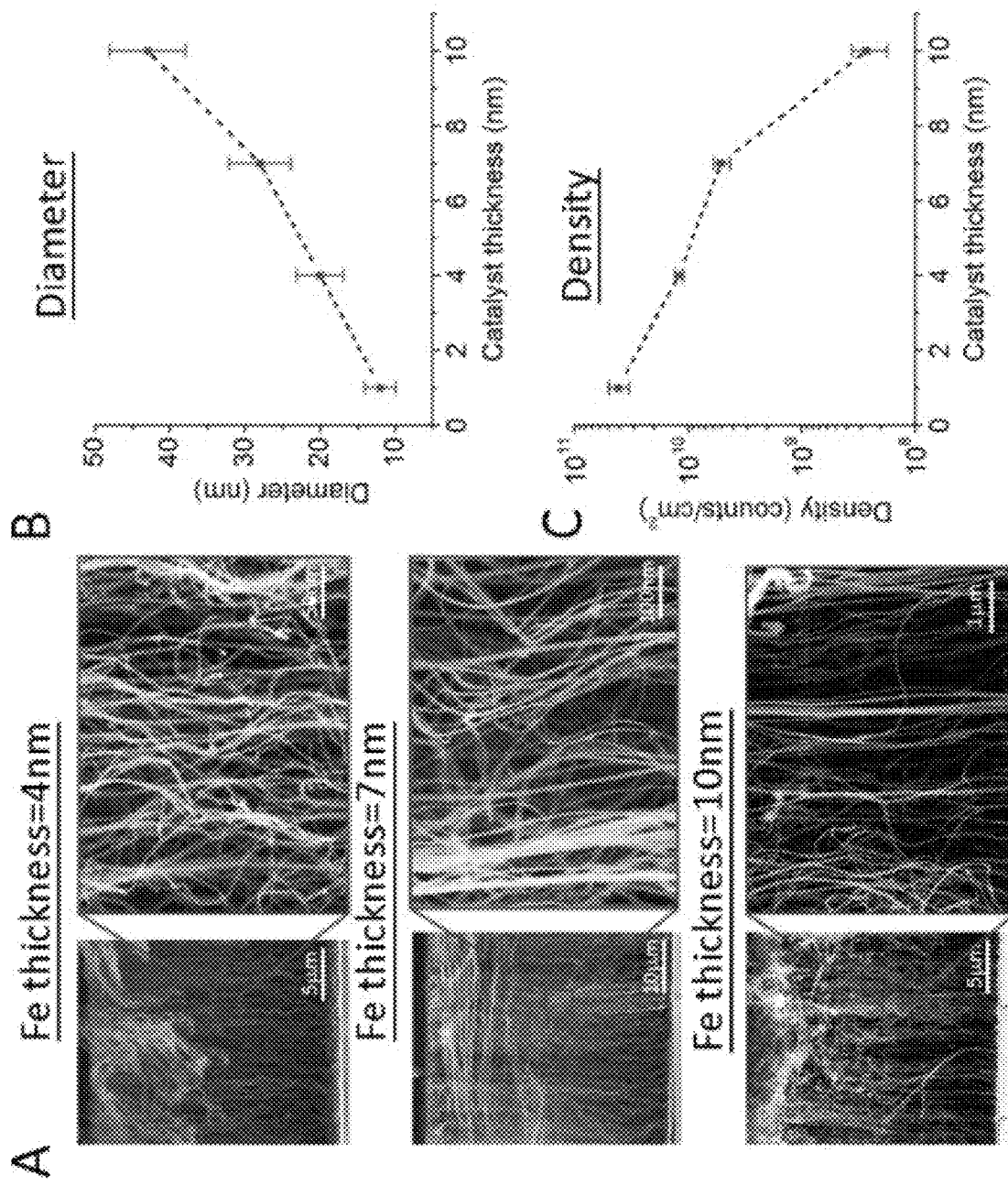

FIG. 18, comprising FIG. 18A through FIG. 18E, depicts the results of experiments demonstrating the effect of the synthesis time on the height, CNT diameter, and density of the vertically aligned CNT structure. Geometrical parameters were measured from SEM images. (FIG. 18A) Height of VACNT structure synthesized for 30 minutes on 1 nm, 3 nm, 6.5 nm, 9 nm, and 12 nm thick iron thin films (n=8). (FIG. 18B through FIG. 18D) The effect of the synthesis time on (FIG. 18B) height, (FIG. 18C) CNT diameter, (FIG. 18D) CNT density of the VACNT structure. The CNT was grown on 3 nm, 6.5 nm, and 12 nm thick iron catalyst thin films under 5, 10, 20, 30, and 40 minutes of AACVD synthesis (n=8). (FIG. 18E) Histograms of the CNT diameter formed on 1 nm, 3 nm, 6.5 nm, 9 nm, and 12 nm thick iron thin films. The analysis was based on SEM images. The histograms were fitted for normal distribution in solid lines. The inset is a TEM image of AACVD synthesized CNT on 12 nm thick iron thin film.

Figures 19A, 19B, 19C:
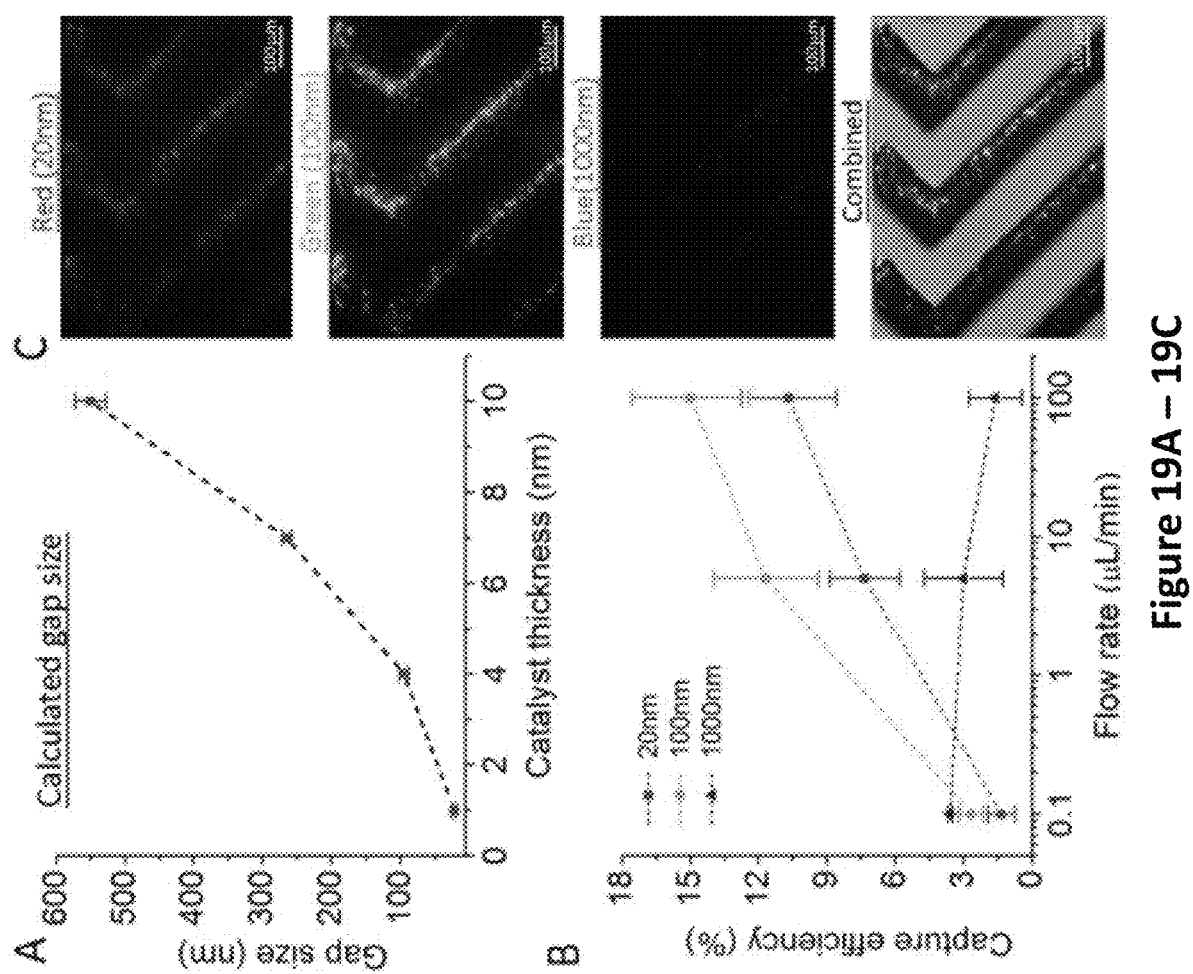

FIG. 19, comprising FIG. 19A and FIG. 19B, depicts the results of experiments demonstrating the characterization of the filtration related properties of the vertically aligned CNT structure. (FIG. 19A) Porosity calculated from cylindrical pillar arrangement model and SEM images of CNT growing on 1 nm, 3 nm, 6.5 nm, 9 nm, and 12 nm thick iron catalyst thin films for 30 minutes AACVD synthesis (n=8). The inset illustrates the geometry model of the CNT forest. (FIG. 19B) Calculated porosity of CNT grew on 3 nm, 6.5 nm, and 12 nm thick iron catalyst thin films, based on geometry assumption plotted in inset of (FIG. 19A).

Cross-sectional SEM images (FIG. 18A) were analyzed and it was observed that the nanoscale geometry of VACNT could be controlled by iron catalyst thickness. CNT diameter and density can be turned in the range of 14~45 nm and $2 \times 10^8$-$5 \times 10^{10}$/cm$^2$, respectively (FIG. 18B and FIG. 18C). By using diameter and density data, it was calculated that the gap size of the VACNT forest has a range of 20-550 nm (FIG. 19A). To study the size-based capturing process, a mixture of fluorescent polystyrene nanospheres of 20 nm (red), 100 nm (green), and 1000 nm (blue) in diameter were added into 95 nm gap devices and the flow-through was collected under a flow rate ranging from 0.1~100 µl/min. In general, 100 nm and 20 nm nanospheres could be captured and the capture efficiency increased with flow rate. 100 nm nanospheres had higher capture efficiency (~16%) at 100 µl/min flow rate (FIG. 19B and FIG. 19C).

FIG. 20 depicts the testing setup of the CNT-STEP microdevice. The virus sample was loaded into the inlet sample reservoir and processed through CNT-STEP microdevice via a vacuum source connected through a waste trap at the outlet. The vacuum pressure was measured by a miniature pressure sensor and regulated by a precision mechanical regulator.

Clinically relevant samples were constructed by spiking H5N2 virus (FIG. 20A) into a swab medium collected from a healthy (virus-free) chicken. 200 µl of H5N2 swab sample were added into a 95 nm device at a flow rate of 100 µl/min and on-chip immunofluorescence assay was applied. Strong green fluorescent signals indicated that H5N2 was trapped inside the herringbone structure (FIG. 20B), which was later confirmed by SEM images (FIG. 20C). Virus was lysed on-chip and RNA extracted for genetic detection. FIG. 20D shows that a signature DNA fragment (750 bp) was observed in the all H5N2 samples and the positive control, but not the negative control.

FIG. 21 depicts SEM images of cross-sectional views of CNT structure growing on 1, 3, 6.5, 9, and 12 nm thick iron catalyst layer. SEM magnification: 2,000 (top) and 20,000 (bottom). (Scale bars: 500 nm (top), 100 nm (bottom)).

More importantly, the device demonstrated an order of magnitude improvement in the detection limit of the current golden standard of virus detection, the RT-qPCR. 1 mL of 0.1 ELD$_{50}$ H5N2 sample was added into the 95 nm gap device, RNA was extracted, and RT-qPCR was run for RNA detection (FIG. 21, red lines). By comparing with 0.1 ELD$_{50}$ (blue lines) and virus sample 1 ELD$_{50}$ (black lines) virus samples, the detection limit of RT-qPCR was improved by at least one order of magnitude. Finally, after enrichment by the device, the scratched VACNT structures with virus was inoculated into chicken eggs, and H5N2 was successfully propagated after three days of ex vivo culture.

Example 3: Tunable and Ultra-Sensitive Virus Detection Using Carbon Nanotube Arrays Viruses may cause unpredictable and recurring outbreaks that lead to devastating mortality and traumatic economic losses, as exemplified by the 1918 influenza pandemic, the ongoing battle against HIV/AIDS, and the most recent Ebola and Zika outbreaks (Fauci, A. S. et al., New Engl. J. Med. 2012, 366:454-461). However, there is still a large pool of unknown mammalian and human viruses, among which could be critical viral pathogens (Anthony, S. J. et al., mBio 2013, 4; Woolhouse, M. et al., Philos. T. Roy. Soc. B 2012, 367:2864-2871). Almost all lethal viral outbreaks in the past two decades were caused by new emerging viruses (Chiu, C. Y. et al., Curr Opin Microbiol 2013, 16:468-478). As over 50% of the human pathogens are known to be zoonotic (Howard, C. R. et al., Emerg Microbes Infect 2012, 1: e46; Mark, E. J. W. et al., Emerg. Infect. Dis. 2005, 11:1842), virus samples can be originated from various sources, e.g. human, animals, and different environments. Thus, it is clear that the successful virus isolation, identification, and genome characterization, directly from field and clinical samples will lead to rapid discovery of emerging viral pathogens (Pennington, H., Nat. Rev. Micro. 2004, 2:259-262).

Since the high mutation rate and the genetic diversity of viruses warrant extensive surveillance (King, D. A. et al., Science 2006, 313:1392-1393), various virus detection approaches have been established: i) enzyme-linked immunosorbent assay (ELISA) (Yolken, R. H., Yale J. Biol. Med. 1980, 53:85-92), ii) polymerase chain reaction (PCR) (Ellis, J. S. et al., Rev. Med. Virol. 2002, 12:375-389; Spackman, E. et al., J. Clin. Microbiol. 2002, 40:3256-3260), iii) virus isolation (Eisfeld, A. J. et al., Nat. Protocols 2014, 9:2663-2681; Wood, J. M. et al., Nat. Rev. Micro. 2004, 2:842-847), and iv) next generation sequencing (NGS) (Chiu, C. Y. et al., Curr Opin Microbiol 2013, 16:468-478; Radford, A. D. et al., J. Gen. Virol. 2012, 93:1853-1868). However, additional advancements in the sample preparation techniques to enrich and concentrate viruses are urgently needed (Beerenwinkel, N. et al., Front. Microbiol. 2012, 3:16; Chin, C. D. et al., Lab Chip 2012, 12:2118-2134; Heider, S. et al., Virology 2014, 462-463:199-206; Li, L. et al., J. Virol. Methods 2015, 213:139-146; Noda, T., Front Microbiol 2011, 2:269). In addition, the most conventional virus-sample preparation protocols utilize immunological capture, physical separation or a combination of both (van Reis, R. et al., L. Membrane Sci. 2007, 297:16-50; Yeh, Y.-T. et al., Ann Biomed Eng, 2014, 1-11). Unfortunately, immunological capture requires prior knowledge of the targets, thus it is not appropriate for virus discovery and can lead to technical difficulties for identifying new or emerging virus strains. Ultracentrifugation is the most commonly used physical method for virus enrichment and concentration. Unfortunately, it involves bulky equipment, intensive labor, lengthy sample preparation, and has limitations for concentrating small amounts of viruses in minute volumes (Radford, A. D. et al., J. Gen. Virol. 2012, 93:1853-1868; Yeh, Y.-T. et al., Ann Biomed Eng, 2014, 1-11; Bibby, K., Trends Biotechnol. 2013, 31:275-279). Microfiltration membranes can remove large particles within samples while keeping the virus particles in the supernatant. It is normally used as one of the steps in the whole sample preparation protocol for virus analysis, however it neither removes contaminants of small size (e.g. nucleic acids and proteins) nor concentrates the sample (Daly, G. M. et al., PLOS ONE 2011, 6: e28879; Hall, R. J. et al., J. Virol. Methods 2014, 195:194-204; Rosseel, T. et al., J. Virol. Methods 2015, 222:72-80). Although ultrafiltration membranes are widely used as an essential viral clearance step in the biopharmaceutical production from human or animal origin (van Reis, R. et al., L. Membrane Sci. 2007, 297:16-50; DiLeo, A. J. et al., Nat. Biotech. 1992, 10:182-188), their usage for virus detection is rare primarily due to their low porosity, high operation pressure, poor virus viability and difficulty in virus access for further analysis.

In this context, robust arrays of aligned CNTs with controlled inter-tube distance could be used to effectively trap/concentrate viruses within a 3-dimensional porous system. Although CNTs have been used as biochemical sensors (Balasubramanian, K. et al., Anal. Bioanal. Chem. 2006, 385:452-468), imaging probes (Liu, Z. et al., Nano Res. 2009, 2:85-120), drug delivery vehicles (Cai, D. et al., Nat. Methods 2005, 2:449-454), X-ray sources (de Heer, W. A. et al., Science 1995, 270:1179-1180), neuron protection (Lee, H. J. et al., Nat. Nano. 2011, 6:121-125), treatment of drug addiction (Xue, X. et al., Nat. Nano. 2016, 11:613-620), and substrates for immunological capture of mammalian cells and bacteria (Chen, G. D. et al., Small 2011, 7:1061-1067), they have not been integrated into tunable devices able to isolate viruses of different sizes. Here, a reliable, scalable CNT-STEM technology is developed that provides size-based, label-free, viable enrichment and concentration of viruses from field samples. The following study synergistically integrates bottom-up controlled nanotube synthesis with top-down microfabrication. The study demonstrates that the CNT-STEM not only improves virus detection sensitivity and the minimal virus concentration for virus isolation by at least 100 times (FIG. 22A and FIG. 22B), but also removes host and environmental contaminants, and concentrates samples to enable direct virus identification by NGS from field-collected samples.

The materials and methods are now described.

Patterning of Iron Catalyst Thin Film

As shown in FIG. 23A, a 4" single-side polished prime silicon wafer was cleaned in piranha solution, acetone, isopropyl alcohol (IPA) and ultrapure water sequentially. Lift-off photoresist LOR5A (MicroChem) and negative photoresist NFR105G (JSR Microelectronics) were spin-coated at 4000 rpm, respectively, followed by photolithography patterning with a contact aligner (Karl Suss MA/BA6). Iron was deposited by an e-beam evaporator (Semicore) under 10-7 mTorr vacuum with deposition rate of 0.1 nm per second to target thickness of 1, 3, 5, 8, 10 nm. The actual thickness of the deposited films was measured to be 1.0±0.1, 3.0±0.2, 6.5±0.5, 9.2±0.4, 11.9±0.8 nm by AFM (Bruker Dimension Icon). A thin layer of negative photoresist NFR105G was spin-coated as a protective layer prior to dicing. The silicon substrate was then diced into individual dies of 1.2 cm by 1.2 cm by a dicing saw (Advanced Dicing Technologies). Photoresist was lift-off by soaking the substrate inside remover-PG (MicroChem) overnight at 60° C.

N-MWCNT Synthesis by AACVD

The aerosol-assisted chemical vapor deposition (AACVD) setup consisted of an ultrasonic nebulizer (RBI instrumentation, Meylan, France), two tube furnaces (Thermo Scientific) arranged in series and a waste trap filled with acetone (FIG. 24). Benzylamine (Fluka, CAS: 100-46-9) was fed through the system by a nebulizer, working as both carbon source and nitrogen dopant. The iron-patterned substrates were placed in the second furnace. All components were airtight sealed by silicone paste (McMaster Carr) and flushed with argon and 15% hydrogen of 0.5 L/min flow rate for 5 minutes. The furnace temperature ramped to 825° C. in 30 minutes. When the temperature reached 825° C., the nebulizer was turned on and the argon and 15% hydrogen flow was increased to 2.5 L/min. After the synthesis process was completed, the nebulizer was turned off, the flow rate of carrier gas was decreased back to 0.5 L/min and the furnace temperature was set back to 25° C. The cooling process usually took 3 hours for the furnaces to reach room temperature.

CNT-STEM Assembly and Experimental Setup

The N-MWCNT forest pattern was designed as a droplet-shape to distribute the aqueous sample evenly. The patterned N-MWCNT structure on the silicon substrate was integrated into a microfluidic device by bonding it with a PDMS chamber. The PDMS chamber was fabricated by standard soft lithography (Xia, Y. et al., Annu. Rev. Mater. Sci. 1998, 28:153-184). The mold was fabricated by patterning SU-8 on silicon wafers with a contact aligner (Karl Suss MA/BA6). The ratio of the depth of the PDMS chamber and the height of the N-MWCNT forest was ~0.8-0.9. Then, well-mixed PDMS precursor (part A: part B=10:1, Sylgard 184, Dow Corning) was poured onto the SU-8 mold and bake at 60° C. for 40 minutes. The partially cured PDMS layer was diced into 1.2 cm by 1.2 cm squares with a razor blade. Two through-holes serving as inlet and outlet, 4 mm and 1 mm in diameter respectively, were punctured through the PDMS using a Luer adapter (BD). Before bonding, both the PDMS chamber and the N-MWCNT patterned silicon substrate were treated with RF oxygen plasma (M4L, PVA TePla Inc) with processing parameters of 400 mTorr oxygen pressure, 50 W power, and 30 seconds duration. Then they were aligned and gently pressed together and baked at 85° C. for four hours.

The experimental system for the CNT-STEM includes a sample reservoir, a waste trap, and components for flow actuation and control (FIG. 23B). A 100 μL cylindrical sample reservoir formed with silicone tube of 5 mm inner diameter was attached to the inlet port. The outlet port was connected to a custom-made waste trap using a silicone tube of 0.5 mm inner diameter. The waste trap had three connections to a vacuum pump, a miniaturized pressure sensor, and a mechanical pressure regulator respectively. The vacuum pump (McMaster-Carr) provided a negative pressure. The miniaturized pressure sensor (Honeywell ASDXL) had a sensing range of 10 inches of water column. It was soldered to a printed circuit board (McMaster-Carr) and powered by a 9V battery. The mechanical pressure regulator (McMaster-Carr) regulated the vacuum suction. Fluidic connections were sealed by applying uncured PDMS precursor as sealant to the ends of the connections, and then cured under room temperature for 24 hours.

Characterization of N-MWCNT Forest Geometries of Vertically Aligned N-MWCNT by AACVD Synthesis The nanoscale geometries of the N-MWCNT synthesized on 3 nm, 6.5 nm and 12 nm thick iron catalyst thin films under different synthesis time of 5, 10, 20, 30 and 40 minutes were studied by cross-sectional SEM images of the N-MWCNT structure taken by a field emission SEM with accelerating voltage of 5 kV (LEO 1530 FESEM). The height of the N-MWCNT forest was characterized with cross-sectional SEM images under $8\times10^2$ magnification. For diameter analysis of single N-MWCNT, $6\times10^4$ magnification was used and a total number of 500 focused N-MWCNTs were measured with ImageJ. Both the N-MWCNT diameter D and its probability density function $f(D)$ were calculated. For density and inter-tubular distance measurement of the aligned N-MWCNT structure, the images were taken under $2.5\times10^4$ magnification at bottom of the N-MWCNT forest close to the substrate. One line equivalent to 1 μm in length was drawn perpendicular to the N-MWCNT growth direction on each image. The numbers of focused N-MWCNTs that crossed the line was counted to calculate its linear density $\lambda$. 20 images of each synthesis condition were analyzed and five 1 µm lines were drawn for each image. For the inter-tubular distance, the distance was measured between pairs of neighboring focused N-MWCNTs that were crossed by the drawing line. 20 images of each synthesis condition were collected and data on 5 drawing lines on each image were analyzed for each image. Assuming the N-MWCNT density is isotropic in 2D, the porosity Φ can be calculated from the measured N-MWCNT line density λ, diameter $D_i$ and the probability density function of the diameter $$f(D_i):1 - \frac{\pi}{4}\lambda^2 \sum_i f(D_i)D_i^2.$$

Measurement and Analysis of the Iron Nanoparticle Geometry

To study the geometrical properties of the iron nanoparticles and the relationship to those of the N-MWCNTs, silicon wafers were diced into device dies and iron catalyst thin films of targeted thicknesses of 1, 3, 5, 8, 10 nm were deposited on different device dies. For one set of device dies with different thicknesses of the iron catalyst film, the AACVD process went through the thermal ramping stage and was terminated prior to feeding the precursor (benzylamine). The SEM images of the top view of the iron nanoparticles were taken under $5\times10^4$ magnification. SEM images of iron particles were analyzed for their size and spatial distribution using Matlab image processing toolbox. The average particle-to-particle distance was calculated by applying the Delaunay triangle selection to determine the closest neighbor particles, then represented as the mean of the three edges $r_1$, $r_2$ and $r_3$ (FIG. 25) (Bray, D. J. et al., J. R. Stat. Soc. Ser. C-Appl. Stat. 2012, 61:253-275).

Raman Spectra Measurement of N-MWCNT

AACVD synthesized N-MWCNT was characterized by Raman microscopy (Renishaw, In Via Raman microscopy) using 514 nm laser excitation for 30 seconds under 50× magnification. The laser power to the sample was 10 µW.

CNT-STEM Filtration Process

The assembled CNT-STEM was primed by adding 10 µL of 0.5% Tween-20 (Sigma-Aldrich) at the inlet port and letting the device sit undisturbed until all the air inside the device was replaced by Tween-20. This wetting process took around 15 minutes. Subsequently, another 50 µL of 0.5% Tween-20 was added to inlet port. The vacuum suction from the outlet was turned on and the differential pressure was maintained at 0.1 psi ($6.9\times10^2$ Pa) to move the aqueous phase through the CNT-STEM. In the meantime, device leakage was tested by estimating the travel speed of the air-liquid interface inside the silicone tubing. If the device passed the leak test, 200 µL Dulbecco's phosphate buffered saline (DPBS) (Cellgro) was added to wash the device. After most of the DPBS flew through the device, the virus sample was then added to the inlet port while the vacuum suction remained. After most of the virus sample was filtered through, 50 µL DPBS were added to rinse the device. All samples containing viruses were filtered through member filters (VWR) of 0.2 µm or 0.45 µm pore size for swab samples and tissue samples before introducing the filtrates using the CNT-STEMs.

N-MWCNT Inter-Tubular Distance Characterized by Nanoparticle Penetration

Fluorescein solution (Sigma-Aldrich, #46955) and polystyrene nanosphere suspensions (Thermo Scientific Inc.) were diluted by 0.5% Tween-20 into final concentration of 0.01% (solid). After device priming, 20 µL of the suspension were loaded at the inlet port. The vacuum suction was turned off after all the suspension was transported into the device. The fluorescence image of the device was taken by an sCMOS camera (Hamamtsu ORCA-Flash4.0 V2) connected to a fluorescence microscope (Olympus IX71). The fluorescence intensity was calibrated and measured by ImageJ (Bankhead, P. Analyzing fluorescence microscopy images with ImageJ. (2014)). The penetration ratio was defined by the ratio of fluorescence intensity outside the CNT droplet-shaped chamber ($I_{in}$) to that inside ($I_{out}$), both corrected with background fluorescence intensity ($I_{bg}$) without the fluorescent agents:

$$\text{Pennetration Ratio} = \frac{I_{out} - I_{bg}}{I_{in} - I_{bg}}.$$

Size Measurement of Nanospheres and AVI Virions

The diameters of fluorescent polystyrene nanospheres were measured by a Nano ZS particle-size analyzer (Malvern Zetasizer, Malvern Instruments Ltd, UK). The size distribution of the nanospheres was calculated by the accompanying software (Nanov510) using a refractive index of 1.59.

Similarly, $10^7$ $EID_{50}$/mL AIV solution was diluted by 1000 fold with 20 mM phosphate buffer at pH 7.4. The suspension was then passed through membrane filters of 0.45 µm (Celltreat scientific products) and 0.2 µm (VWR) pore size sequentially, then analyzed on a Nano ZS particle-size analyzer (Malvern Zetasizer, Malvern Instruments Ltd, UK). By assuming refractive index of 1.48 (Wang, S. P. et al., Proc. Natl. Acad. Sci. U.S.A 2010, 107:16028-16032), the Nanov510 software converted intensity data into diameter measurements.

H5N2 AIV Propagation and Sample Preparation

H5N2 AIV was propagated in specific pathogen-free (SPF) embryonated chicken eggs (ECE) via allantoic cavity route inoculation at 9-11 days of age. The inoculated eggs were placed in a 37° C. egg incubator for 72 hours. Then the eggs were removed from the incubator and chilled at 4° C. for 4 hr. Each egg was cracked open at the top air sac. The shell peeled without breaking the air sac membrane. The allantoic fluid containing the virus was harvested using a 3 mL sterile syringe with a 25G×⅝" needle. The harvested allantoic fluid was clarified by centrifugation at 8000 rpm for 5 minutes. The virus titers were measured in embryo infectious doses 50% ($EID_{50}$) by the Reed-Muench method (Reed, L. J. et al., Am. J. Epidemiol. 1938, 27:493-497). Briefly, the freshly propagated H5N2 AIV stock was prepared in 10-fold serial dilutions from $10^1$ through $10^9$. Each dilution was inoculated into 5 eggs, 0.1 mL per egg. The inoculated eggs were incubated at 37° C. for 72 hours. The eggs were candled daily to remove dead eggs to chill them at 4° C. refrigerator. After 72 hours of incubation, allantoic fluid was harvested from each egg and spin down. The supernatant was collected and passed through a membrane filter of 0.2 µm pore size prior to use. The infection status of each egg was determined by Dot-ELISA. AIV H5N2 samples were produced experimentally by spiking a freshly propagated LPAIV H5N2 strain (A/chicken/PA/7659/1985) into tracheal swabs obtained from SPF chickens.

On-Chip Immunofluorescence Assay for H5N2 AIV Detection and Fluorescence Intensity Measurement After virus capture and phosphate buffered saline (PBS) washing inside the CNT-STEM, monoclonal antibody of the H5 HA protein (100 μL of 1:1000 diluted work solution, Penn State Animal Diagnostic Laboratory) was added through the inlet, incubated at 37° C. for 40 minutes, and washed with 1 mL of PBS. Then goat anti-mouse immunoglobulin conjugated with FITC (100 μL of 1:500 work dilution, KPL) was added and incubated at 37° C. for 40 minutes and followed by 1 mL PBS wash. Fluorescence microscopy images were obtained by an sCMOS camera (Hamamtsu ORCA-Flash4.0 V2) connected to a fluorescence microscope (Olympus IX71). By measuring average intensity of an area of 100 μm×100 μm across the N-MWCNT walls, the fluorescence signal was calculated by ImageJ (Bankhead, P. Analyzing fluorescence microscopy images with ImageJ. (2014)).

Virus Lysis and RNA Extraction

After performing virus filtration by the CNT-STEM, the virus-trapped device was disassembled by peeling the PDMS chamber using a razor blade. Normally the N-MWCNT structure remained on the PDMS surface. The N-MWCNT structure was then scraped from the PDMS chamber with a razor blade and placed into a microcentrifuge tube containing 50 μL lysis/binding solution (MagMax, Life Technologies). The viral RNA was extracted with MagMax™—96 AI/ND viral RNA isolation kit (Life Technologies, Cat. #AM 1835) following the manufacturer's protocol.

Real-Time Reverse-Transcriptase Polymerase Chain Reaction (rRT-PCR)

Primers and a probe specific to influenza type A were used (Spackman, E. et al., J. Clin. Microbiol. 2002, 40:3256-3260). The master solution of rRT-PCR was prepared as a 50 μL reaction mixture using a One Step RT-PCR Kit (Cat. No. 210212, QIAGEN, Valencia, CA), containing 10 μL of template RNA, 25 μL of RNase-free water, 10 μL of 5× Buffer, 2 μL of dNTP mix (10 mM each dNTP), 1 μL of enzyme mix, and 1 μL of each of the two primers. Amplification was performed with a real-time PCR system (7300, Applied Biosystem Inc.) using a reverse transcription step at 50° C. for 30 min. The initial PCR activation step was set at 95° C. for 15 min, then followed by 94° C. for 30 s, 50° C. for 30 s, and 72° C. for 90 s of each cycle for 38 cycles, and lastly finished with a single cycle of 72° C. for 5 min. The data was collected and processed by the manufacturer's software (7300 V1.4.0, Applied Biosystem Inc.). The Ct value was determined by $2^{-\Delta\Delta ct}$ method. The efficiency of the PCR is determined by:

$$\text{Efficiency} = 10^{-\frac{1}{Slope}} - 1,$$

where Slope is the slope of the PCR standard curve.

Virus Isolation and Characterization of the Propagation by DOT-ELISA

N-MWCNTs were collected into a microcentrifuge tube containing 0.1 mL of PBS and inoculated into an ECE as described for virus propagation. After 72 hours of incubation at 37° C., allantoic fluid was harvested. The allantoic fluid infection status was determined by Dot-ELISA using AIV H5 monoclonal antibody. 10 μL test specimens were applied to a strip of a nitrocellulose membrane (Thermo Scientific Inc.). After the membrane was air-dried, blocking solution (10 mL of nonfat milk diluted in 30 mL of water) was added and the membrane was incubated at room temperature for 10-20 minutes. After blocking, the membrane strip was allowed to air dry. Anti-H5 MAb was then applied and incubated for 60 minutes at room temperature, followed by PBS wash for 1-2 minutes with two repeats, and allowed to air dry. Next, goat anti-mouse IgG FITC conjugate was added at 1:500 working dilution of the 0.1 mg/mL stock solution and incubated for 60 minutes at room temperature. The PBS wash step was repeated. Finally, BCIP/NBT (5-bromo-4-chloro-3-indolyl-phosphate/nitroblue tetrazolium, #B8503, Sigma Aldrich) was applied and the membrane was kept in the dark during color development.

Sample Preparation for Next Generation Sequencing (NGS)

To prepare a sample for NGS, first cDNA library was built from the total RNA extracted of the sample. TruSeq Stranded Total RNA Sample Prep Kit (Illumina, San Diego, CA, USA. Cat. #RS-122-2201) was used to reverse transcribe the extracted RNA sample (total RNA) into cDNA. The manufacturer instructions were followed with the exception that the initial poly A enrichment step was skipped. Briefly, by applying elevated temperatures, total RNA was fragmented into shorter segments. Those shorter RNA fragments were first reverse transcribed into cDNA strands with random primers. By adding DNA polymerase I and RNase H, the complementary cDNA strands were synthesized. The cDNA was ligated to an adaptor and amplified by PCR to generate cDNA library. The quality of the cDNA library was tested by Agilent Bioanalyzer system (Agilent Technologies, Santa Clara, CA, USA). Library concentration was assessed by qPCR using the KAPA Library Quantification Kit Illumina Platforms (Kapa Biosystems, Wilmington, MA, USA). Finally, the prepared cDNA libraries were loaded into different lanes of the MiSeq sequencer using 150 nt single read sequencing (Illumina, San Diego, CA, USA) to generate raw NGS reads.

De Novo Assembly and Analysis

The overall pipeline for sequence data analysis is summarized in FIG. 26. Starting from raw NGS reads, the added sequencing adaptors were removed by SortMeRNA. Quality trimming by Trimmomatic (BWA-MEM) was used to remove matched contaminating sequences of the host (e.g. chicken, turkey, human) and bacteria, as well as rRNA. Unmatched sequence reads were assembled using de novo assembly software SPAdes (V.3.5.0) (Bankevich, A. et al., J. Comp. Biol. 2012, 19:455-477) with Kmer-size setting of 85. After de novo assembly, LASTZ (R. S. Harris, Improved pairwise alignment of genomic DNA. (ProQuest, 2007)) and SAMMtools (Li, H. Bioinformatics 2009, 25:2078-2079) were used to identify and obtain the final viral consensus sequences. Coverage was analyzed by BWA-MEM.

Phylogenetic Analysis

Phylogenetic tree was generated by MEGA (V.6.06) (Kumar, S. et al., Computer applications in the biosciences: CABIOS 1994, 10:189-191) using ClustalW alignment and maximum-likelihood (ML) (Tamura, K. et al., Mol. Biol. Evol. 2011, 28:2731-2739). The tree topologies were made by bootstrap analysis with absolute distances following 1,000 bootstrap replicates (Felsenstein, J. Evolution 1985, 39:783-791).

Intrahost Variant Calling and Analysis

Intrahost variants (iSNVs) were identified using a haplotype-based variant detector (Freebayes) with setting of ploidy of 1 and error rate of 0.8% (Illumine MiSeq) (Quail, M. A. et al., BMC genomics 2012, 13:341). If the frequency of variant population was higher than 0.8%, it was considered as an iSNV site. The genetic variants were annotated by SnpEff v4.1 (Ruden, D. M. et al., Fly 2012, 6:80-92). The NGS data was displayed by generating plots with Circos (v 0.67) (Krzywinski, M. et al., Genome Res. 2009, 19:1639-1645).

Field Sample Collection and Preparation AIV field samples were collected by inserting Dacron swabs (Fisherbrand, Catalog No. 14-959-97B) into cloaca of poultry objects. The swabs were transferred into a cryovial containing 5 mL viral transport medium, which was prepared by following WHO guidance. Prior to testing, a cryovial containing swab was first shaken by a vortex mixer (IKA MS2 S9 Mini Shaker) and then centrifuged under 1,500 g for 30 minutes. The supernatant was collected and passed through a membrane filter of 0.2 μm pore size prior to use.

The turkey tissue sample was from a turkey eyelid with gross lesion of swelling. The tissue sample was minced with sterile scissors in a 20 mL sterile plastic container (Cat No. 14310-684, VWR) containing viral transport medium at 1:5 (w/v) dilution. The minced tissue was transferred to a sterile Stomacher bag and homogenized in a Stomacher blender (Model 80, Seward Ltd., UK) for 2-3 minutes. The tissue homogenate was centrifuged at 1500 rpm for 10 min. The supernatant was filtered through a 0.45 μm syringe filter into a polypropylene conical tube, ready for virus detection.

The results are now described.

Figures 27A, 27B, 27C, 27D, 27E, 27F:
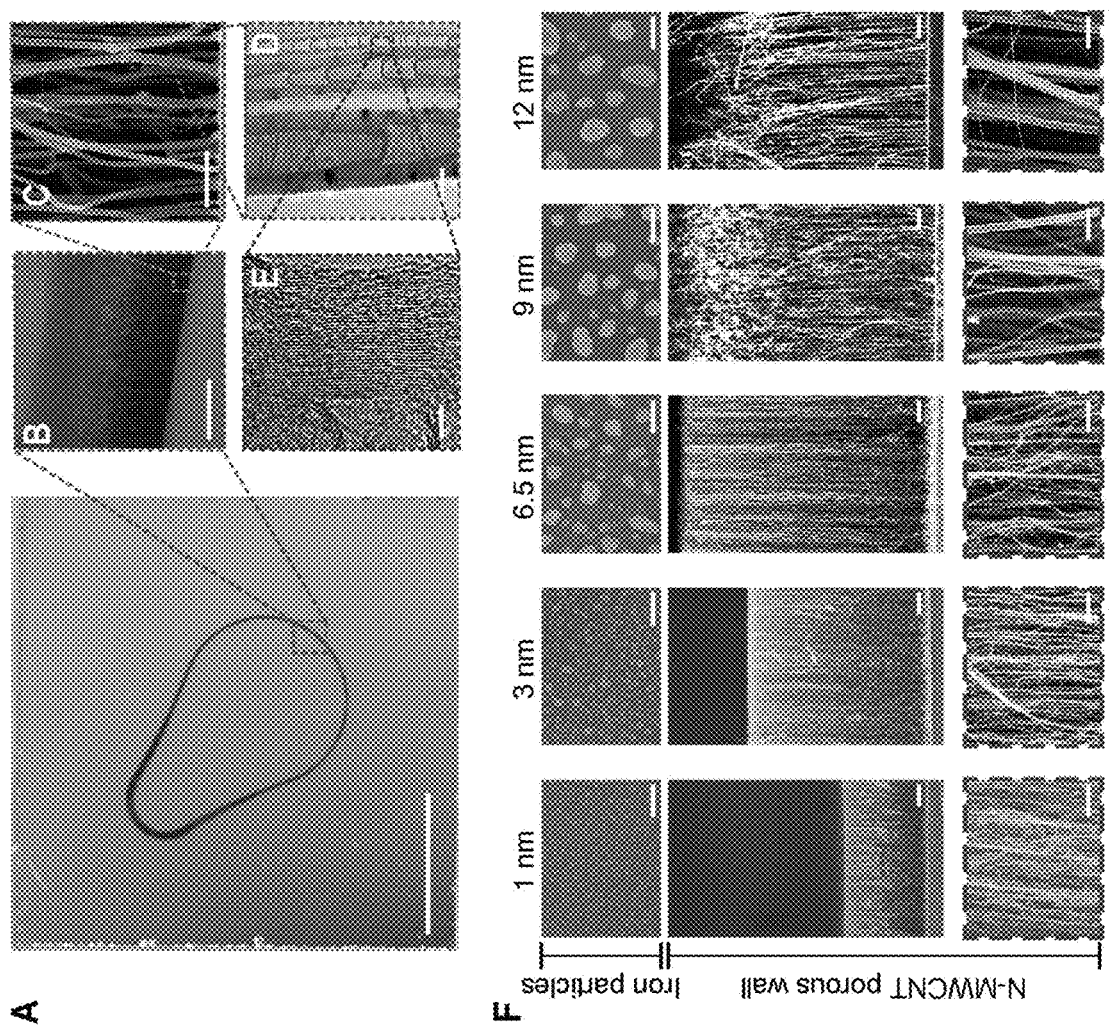
Figures 27G, 27H, 27I, 27J:
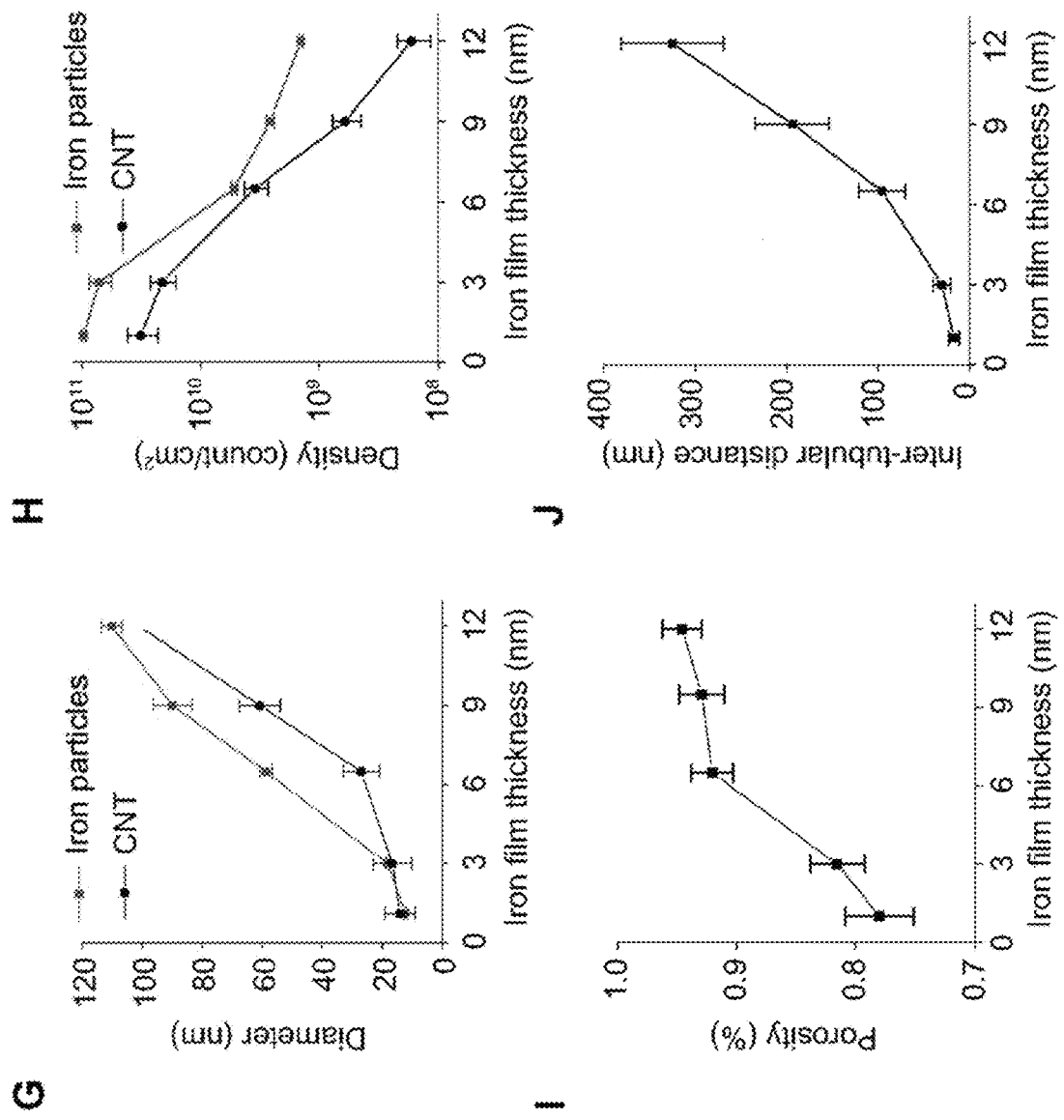
Figures 28A, 28B, 28C, 28D, 28E, 28F:
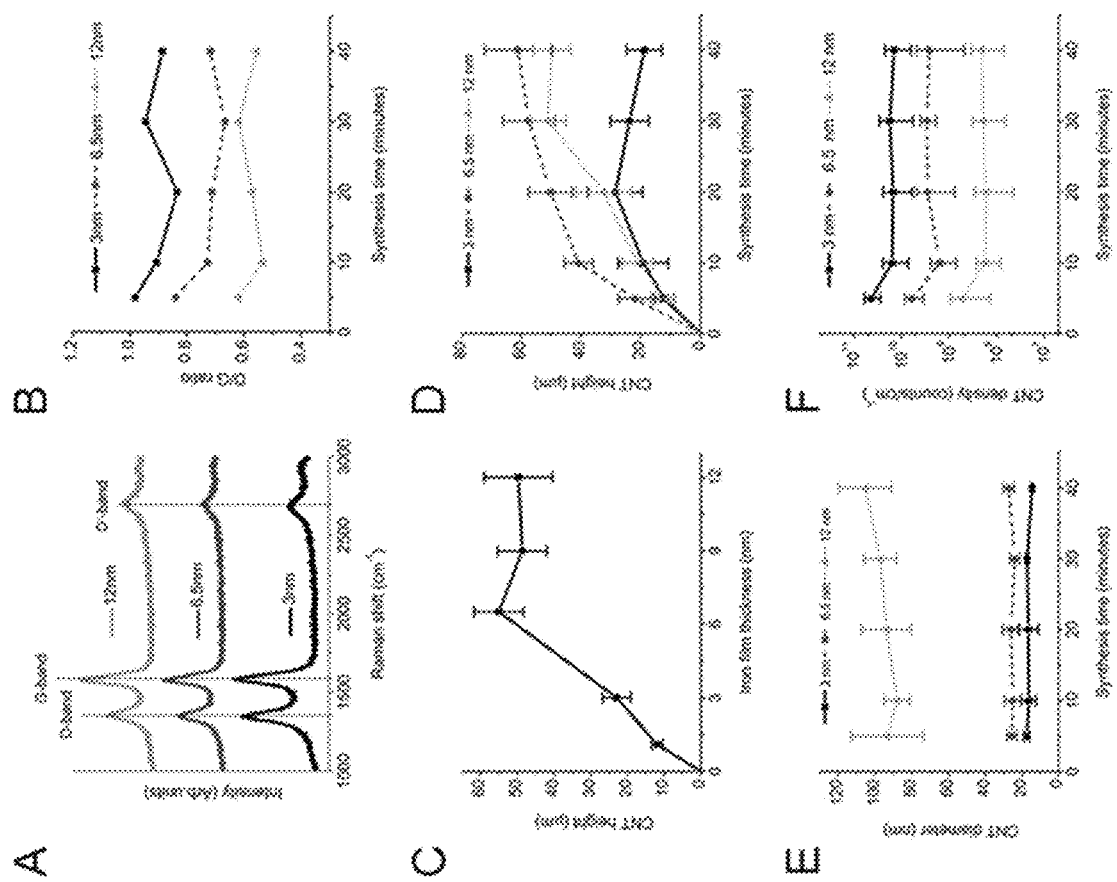

Device Operation and Design Based on Tunable Inter-Tubular Distance of Aligned N-MWCNTs Depending on the type and source of the virus-containing sample, virus particles need to be released into aqueous suspensions by gentle vortexing, shaking (for swab samples) or tissue homogenization (for tissue samples), before they are introduced into the CNT-STEM (FIG. 22A). Large cells or tissue debris were removed by filtering the crude samples with membrane filters exhibiting pore size of 220 nm or 450 nm (not shown). As the virus suspension flows through the CNT-STEM, virus particles are efficiently captured by the N-MWCNT arrays while contaminants of small size flow through (FIG. 22B). If needed, the viruses (tightly adhered to the carbon nanotubes) can be easily retrieved/studied after opening the device (FIG. 23A, FIG. 23B). In order to synthesize these vertically aligned N-MWCNT on the micro-device substrate, standard semiconductor batch microfabrication techniques were used to pattern catalyst (iron clusters), followed by selective growth using aerosol-assisted chemical vapor deposition (AACVD; FIG. 27A and FIG. 24) (Reyes-Reyes, M. et al., Chem. Phys. Lett. 2004, 396:167-173; Villalpando-Paez, F. et al., Chem. Phys. Lett. 2006, 424:345-352).

SEM and TEM images (FIG. 27B through FIG. 27E) as well as Raman measurements with calculated D/G intensity ratios (FIG. 28A and FIG. 28B) confirm the presence of N-MWCNTs synthesized directly on the substrates (Reyes-Reyes, M. et al., Chem. Phys. Lett. 2004, 396:167-173; Villalpando-Paez, F. et al., Chem. Phys. Lett. 2006, 424: 345-352; Sumpter, B. G. et al., ACS nano 2007, 1:369-375). N-MWCNTs were selected for their excellent mechanical strength (Yu, M. F. et al., Science 2000, 287:637-640) and optimal biocompatibility as reported by a previous study (Mihalchik, A. L. et al., Toxicology 2015, 333:25-36). After growing N-MWCNT arrays on patterned areas of the substrate, the silicon substrate was bonded with a PDMS chamber in order to perfectly seal the micro-fluidic chamber without experiencing any leakage.

An important accomplishment of this work is the control of the inter-tubular distance within the CNT arrays so they could match different virus sizes. In this context, different iron catalyst thickness were deposited onto the Si substrates (FIG. 27F through FIG. 27J). When the thickness of the iron catalyst thin film increases from 1 nm to 12 nm, the density of the iron particles decreases while the particle diameter increases, thus causing the inter-tubular distance of N-MWCNTs to increase from 17±6 nm to 325±56 nm. It is also noteworthy that N-MWCNTs consist of concentric tubules exhibiting average diameters of 17-99 nm. In general, the height of the N-MWCNTs also increases over time, however the growth rate significantly decreases after 20-30 minutes of synthesis (FIG. 28C through FIG. 28F).

Performance of Size Tunable Enrichment Characterization

Figures 32A, 32B, 32C, 32D:
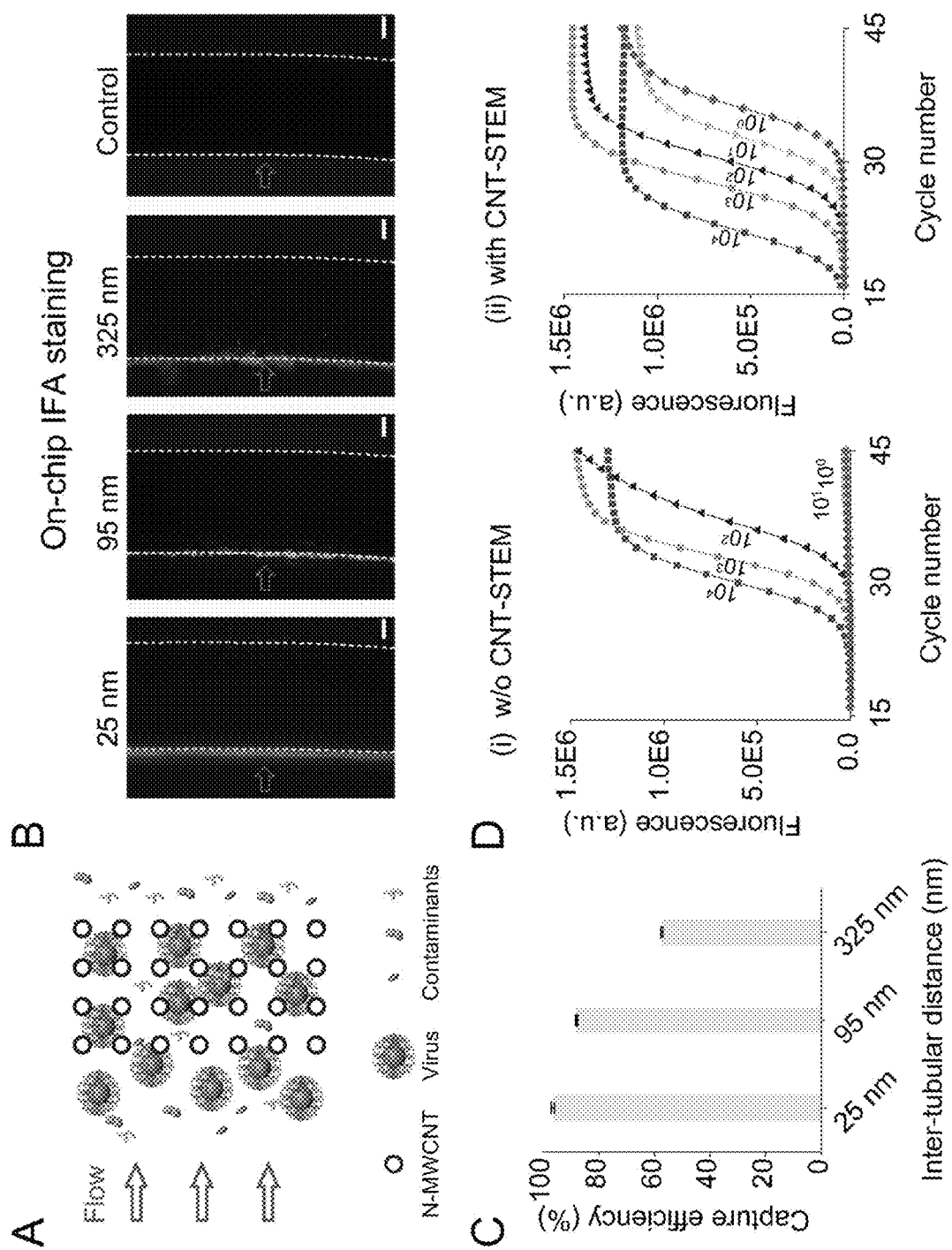

In order to validate the size-tunable enrichment capability of the CNT-STEM, fluorescent molecules and fluorescent polystyrene nanospheres of 20 nm, 50 nm, 100 nm, 140 nm, 400 nm, and 1000 nm in diameter were tested and introduced into CNT-STEMs exhibiting different inter-tubular distances (FIG. 29A and FIG. 30A). FIG. 29B shows the filtration characteristics of CNT-STEMs with 25 nm, 95 nm and 325 nm inter-tubular distances. They all have a binary separation profile, meaning that for a CNT-STEM with a particular inter-tubular distance, smaller nanoscale particles usually penetrate the N-MWCNT structure while larger particles cannot. The particle diameter corresponding to a 50% penetration ratio (the background-corrected fluorescence intensity of the filtrate to that of the original suspension) was defined as the critical particle size of the CNT-STEM with a specific inter-tubular distance (FIG. 31). However, the fluorescence intensity inside the N-MWCNT array is extremely low, maintaining at the same level before and after fluorescein or fluorescence nanospheres flow into the device. This can be explained by the high optical absorbance of the N-MWCNT forest, reported for vertically aligned carbon nanotube forests as a nearly perfect black body absorber (deHeer, W. A. et al., Science 1995, 268:845-847; Mizuno, K. et al., Proc. Natl. Acad. Sci. U.S.A 2009, 106:6044-6047; Yang, Z.-P. et al., Nano Lett. 2008, 8:446-451). Similarly, the viruses inside the N-MWCNT array also elude fluorescence detection (FIG. 32A).

By opening the CNT-STEM device and after observing the N-NWCNT array under SEM, the nanospheres embedded inside the N-MWCNT array could be clearly visualized (FIG. 30B). Thus, in order to separate large nanoscale particles from small contaminates, the inter-tubular distance of the N-MWCNT can be tuned to be smaller than the target nanoscale particles but larger than the contaminants.

Label-Free Capture of Viruses by CNT-STEM

A low pathogenic (LP) avian influenza virus (AIV) (Gao, R. et al., Nwe Engl. J. Med. 2013, 368:1888-1897; WHO, "World health report-A safer future: global public health security in the 21st century," (Geneve, 2007); Yang, Z. Y. et al., Science 2007, 317:825-828) was used as a model system to characterize and optimize the CNT-STEM performance. In particular, the performance of the CNT-STEM was studied using swab samples of a LPAIV subtype H5N2 (A/chicken/PA/7659/1985) by spiking freshly propagated viruses into tracheal swabs obtained from specific pathogen-free (SPF) chickens. The size of the H5N2 LPAIV was measured as 93±35 nm (FIG. S5). When 50 μL processed swab supernatant containing $10^7$ $EID_{50}$/mL H5N2 LPAIV was introduced into CNT-STEMs of 95 nm inter-tubular distance, SEM and TEM images clearly showed virus particles well distributed and efficiently trapped inside the N-MWCNT array FIG. 22B insets). The CNT-STEM captured viruses are readily detected by on-chip indirect fluorescent antibody (IFA) assay using AIV H5 subtype specific monoclonal antibody (FIG. 32A, FIG. 32B) (Lu, H. et al., J Veter Sci Med 2013, 1:5). In general, CNT-STEMs of smaller inter-tubular distance showed stronger fluorescence, thus indicating a higher density of the captured virus. However, as explained above, viruses trapped inside the N-MWCNT structures cannot generate fluorescence. Thus the on-chip fluorescence staining can only qualitatively detect the existence of the viruses, but incapable of quantify virus counts within CNT forests.

In order to measure virus capture efficiency, conventional reverse transcription real-time PCR (rRT-PCR) was applied. CNT-STEMs were made with three different inter-tubular distances of 25 nm, 95 nm and 325 nm. Each CNT-STEM was loaded with 50 µL sample containing $10^6$ $EID_{50}$/mL H5N2 LPAIV. By measuring the original virus titer and that of the flow-through after enrichment with CNT-STEM, virus capture efficiency of the CNT-STEMs with 25 nm, 95 nm and 325 nm inter-tubular distances was measured as 96.5±0.5%, 88.0±0.3% and 57.5±0.4%, respectively (FIG. 32C, FIG. 33, FIG. 34).

Virus Concentration and Enrichment

The most commonly used viral surveillance tests are rRT-PCR (Ellis, J. S. et al., Rev. Med. Virol. 2002, 12:375-389) and virus isolation (Eisfeld, A. J. et al., Nat. Protocols 2014, 9:2663-2681; Wood, J. M. et al., Nat. Rev. Micro. 2004, 2:842-847), where a major challenge is to yield true positive results for samples containing virus concentrations below the detection limits. It was investigated whether CNT-STEM could improve the virus detection limits of rRT-PCR and virus isolation. In many cases, captured viruses need to be retrieved from the device for further analysis. In the present case, this has been easily achieved by opening the PDMS chamber of the device, and recovering the virus-embedded within N-MWCNTs using a pipette tip.

In order to investigate the benefit of CNT-STEM on the overall rRT-PCR assay sensitivity, 1.0 mL H5N2 sample was loaded into CNT-STEMs of 25 nm inter-tubular distance. The viruses were enriched, retrieved, and re-suspended in a final volume of 50 µL. The same volume was used for conventional rRT-PCR without virus enrichment. After the CNT-STEM enrichment, rRT-PCR detected AIV in all samples (6/6) with original titer as low as 1 $EID_{50}$/mL, while without using the CNT-STEM, the rRT-PCR detection limit was measured as 102 $EID_{50}$/mL for the same AIV samples (FIG. 32D, FIG. 33, FIG. 35). Therefore, the CNT-STEM improves the overall rRT-PCR detection limit by at least two orders of magnitude. To exclude the potential effect of N-MWCNT in rRT-PCR, the same amount of N-MWCNTs was added inside the CNT-STEM into the rRT-PCR reaction, and it was found that the N-MWCNTs do not exhibit adverse effects (FIG. 36).

Virus isolation remains the "gold standard" for AIV diagnostics (Eisfeld, A. J. et al., Nat. Protocols 2014, 9:2663-2681). For this procedure, viable intact virus particles are inoculated into an embryonated chicken egg (ECE) and kept under proper conditions for virus cultivation. This procedure fails when the original virus concentration is too low or the viruses are non-viable or non-proliferable. Therefore, it was investigated whether CNT-STEM enriched virus samples can be directly used for virus isolation to study if the trapped viruses are viable, and then if the enrichment procedure can potentially improve the well-established virus isolation procedure (FIG. 37A). In this context, the H5N2 AIV was prepared in three serial dilutions in titers of $10^4$ $EID_{50}$/mL, $10^3$ $EID_{50}$/mL, and $10^2$ $EID_{50}$/mL. After 72 hours post inoculation in ECEs, viruses were collected from the allantoic fluid and Dot-ELISA assay applied using antibody against AIV H5 antigen to test for the existence of viruses (FIG. 37B). The successful virus isolation rates were measured as 100%, 100%, and 90% for CNT-STEM processed samples of original virus titers of $10^4$ $EID_{50}$/mL, $10^3$ $EID_{50}$/mL, and $10^2$ $EID_{50}$/mL, respectively (FIG. 37C). For those samples without CNT-STEM preparation, the corresponding virus isolation rates were determined as 100%, 50%, and 0%, respectively. Therefore, the CNT-STEM retains the virus viability and significantly improves the virus isolation rate, while the N-MWCNTs do not interfere with the virus cultivation process.

Unknown Virus Enrichment and Detection by NGS

While NGS does not require prior knowledge of pathogens, the combination of CNT-STEMs for virus enrichment and NGS for virus identification can be a unique and powerful approach for discovering unknown/emerging viruses. Normally NGS requires starting genetic materials in microgram range with high purity in a small volume of tens of microliters (Acevedo, A. et al., Nat. Protocols 2014, 9:1760-1769), which is prohibitive for field samples of low virus count and highly contaminated. In order to explore the feasibility and develop a practical pipeline of the CNT-STEM for these field conditions, the H5N2 LPAIV strain that had been tested in the present study was used to prepare mimic field samples. Although this is an AIV strain isolated in 1985, its whole genome has not been sequenced before. Freshly propagated viruses were spiked into tracheal swabs obtained from SPF chickens to a final virus titer of $10^7$ $EID_{50}$/mL titer. Then 250 µL of the prepared sample was loaded into a CNT-STEM of 95 nm inter-tubular distance and RNA extracted into a final volume of 50 µL for NGS analysis. Compared with control RNA extracted from 50 µL original H5N2 sample, both the concentrations of the total RNA and the converted cDNA were higher after the CNT-STEM enrichment and concentration (RNA: 870±50 pg/µL versus 144±34 pg/µL, cDNA: 3.8 nM versus 0.8 nM). The NGS viral reads increased from 2.9% (37,627 reads) to 90.6% (1,175,537 reads), thus corresponding to an enrichment factor of ~600, and indicating that the CNT-STEM removed most of the contamination from the chicken host at the same time (FIG. 38A). For the CNT-STEM processed sample, by following the bioinformatics pipeline in FIG. 26, the viral reads by NGS were de novo assembled into eight single contiguous sequences (contigs) with a ~$10^5$× coverage. The nucleotide BLAST search to Genbank (nr/nt database) shows the assembled sequences form the complete genome of the unsequenced H5N2 LPAIV strain (FIG. 38B, FIG. 39). High sequence coverage allowed for the identification of 38 intrahost variants, including 35 intrahost single nucleotide variation (iSNV) sites, 2 intrahost multiple nucleotide variation (iMNV) sites, and 1 deletion site. By searching through sequenced AIV strains in Genbank, the closest strain is H5N2 AIV strain A/mallard/Wisconsin/411/1981 isolated from mallard chicken in Wisconsin, USA in 1981. Phylogenetic analysis of HA and NA gene suggested this H5N2 strain (A/chicken/PA/7659/1985) belongs to the same branch of H5N2 strains isolated during 1980s in the Eastern and Midwestern United States (FIG. 38C, FIG. 40A, FIG. 40B). This unsequenced H5N2 strain was named A/chicken/PA/7659/1985 and deposited into the NCBI database under KP674444-KP674451 (8 segments, complete sequences). This H5N2 strain has the mono-basic cleavage site (PQRETR/GLF) in the HA gene, indicating it is a LPAIV, which can grow only in limited areas of the poultry host (Alexander, D. J. et al., Avian Influenza. (Blackwell Publishing Ltd., 2009), pp. 217-237).

Field Sample Validation—A Case Study of Avian Influenza Surveillance

In order to validate the new approach for real field samples, a cloacal swab pool collected from five ducks during a 2012 AIV surveillance in Pennsylvania were applied. The sample was previously detected as AIV type A positive by rRT-PCR. Without any virus purification and propagation, 1.0 mL of the total ~5 mL suspension of the duck swab sample was enriched and concentrated by a CNT-STEM of 95 nm inter-tubular distance. Measured by rRT-PCR, the CNT-STEM increased virus titer from $6\times10^2$ $EID_{50}$/mL to $2\times10^4$ $EID_{50}$/mL (FIG. 41). NGS and de novo sequence assembly yielded 8 AIV contigs in complete lengths (FIG. 42A), but no AIV related contig was discovered in the sample without CNT-STEM enrichment. A nucleotide BLAST search of Genbank (nr/nt database) showed the sequenced AIV was an unsequenced strain and had different homologies to other reported strains, with ~99% similarities to the closest strains (FIG. 45A, FIG. 45B). Phylogenetic analysis indicated the sample is an emerging H11N9 strain. It is closest to two H11N9 strains A/duck/MN/Sg-00118/2007 (H11N9) and A/pintail/MN/Sg-00149/2007 (H11N9) isolated in Minnesota, USA in 2007 (FIG. 42B, FIG. 43, FIG. 44A, FIG. 44B). It was named "A/duck/PA/02099/2012 (H11N9)" and the sequence was deposited in the NCBI database under KR870234-KR870241 (8 segments, complete sequences). The H11N9 strain was further confirmed by USDA-NVSL (Ames, IA) through serological tests.

Field Sample Validation—A Case Study of an Unknown Turkey Virus

Figures 8A, 8B, 8C, 8D:
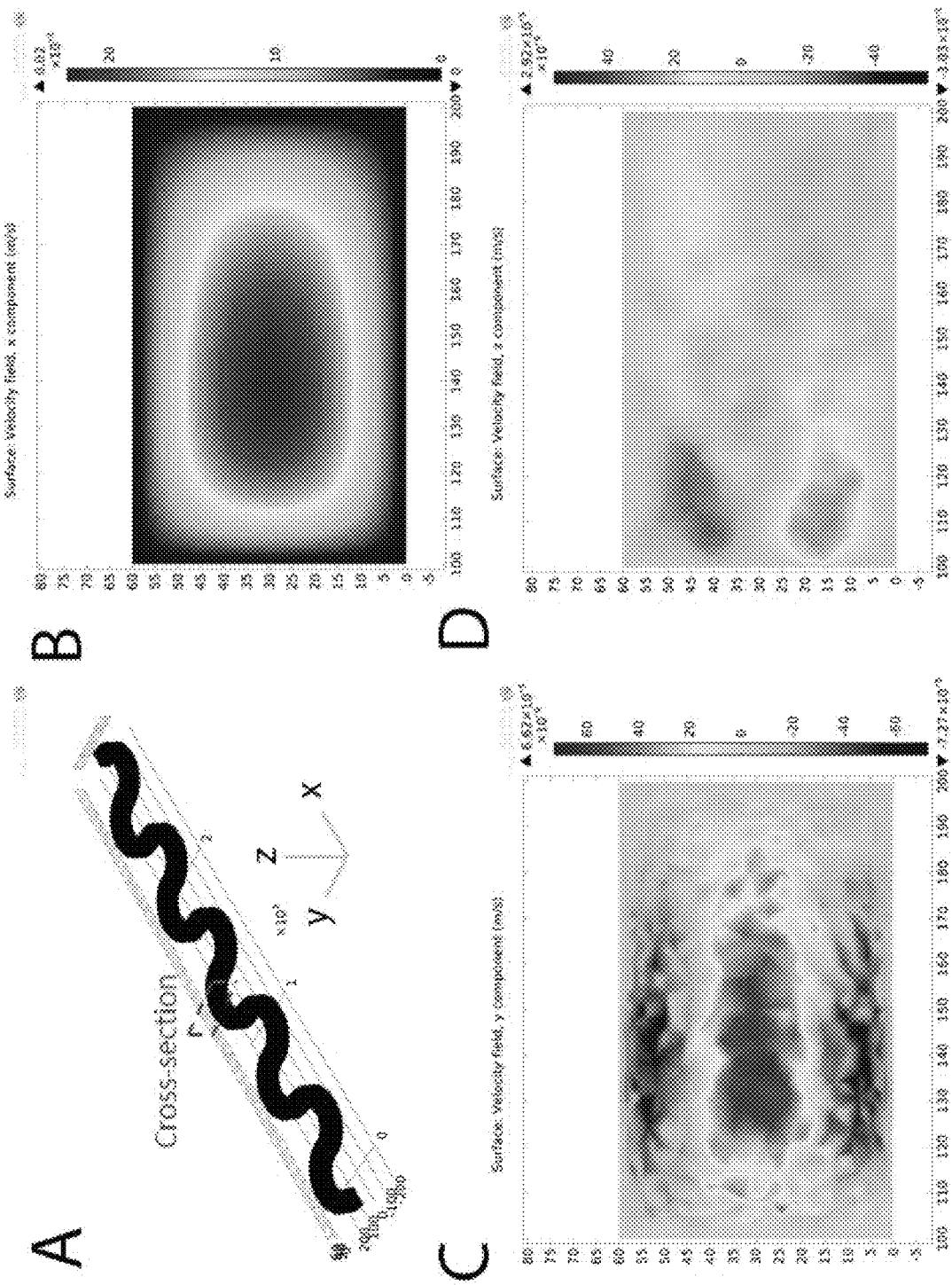
FIG. 8A through FIG. 8D depict fluid flow in the cross section (labeled box) of the 60 µm depth channels. The FEM model, which is a single channel with five repeatable units, was simulated in Comsol.
Figure 9:
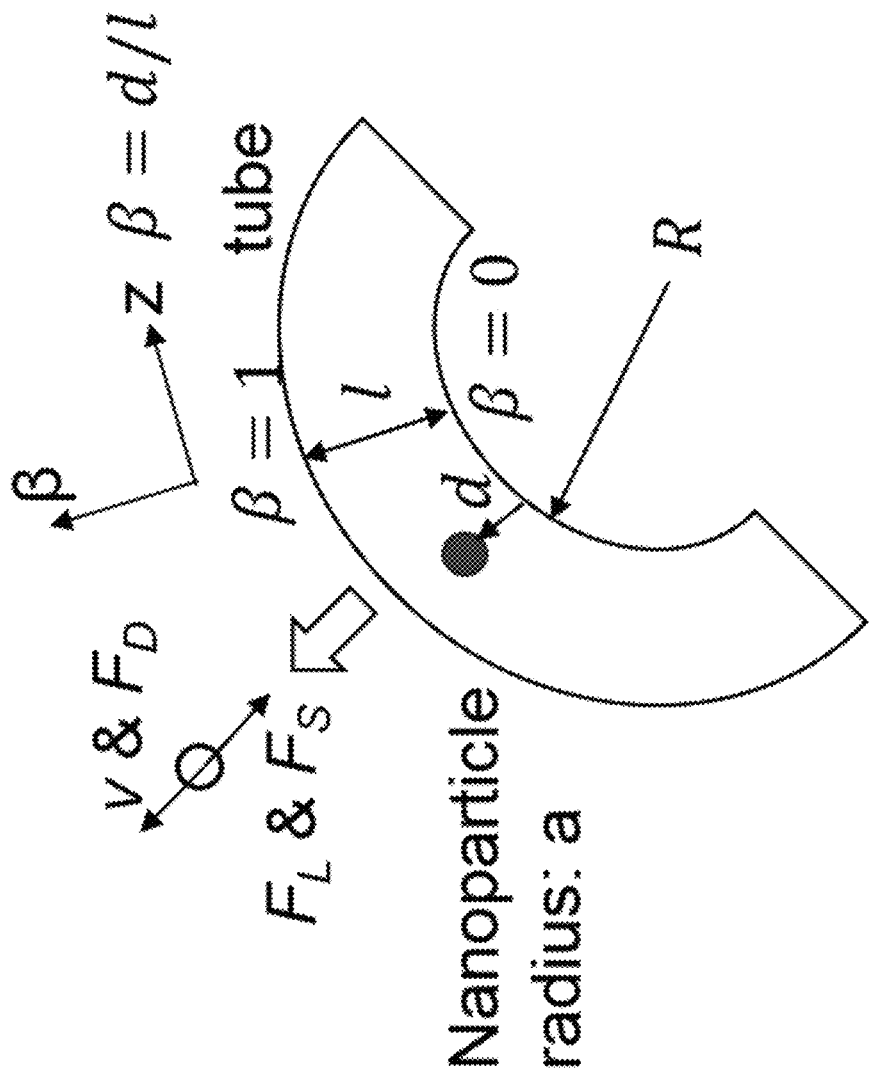
FIG. 9 depicts the forces on nanoparticles in a meandering channel.

To verify the utility of the novel method with a truly clinically "unknown" virus, the CNT-STEM was used to process an eyelid tissue homogenate from a clinical case of a turkey reported to the Penn State Animal Diagnostic Laboratory in the summer of 2014. The turkeys had a symptom of blepharoconjunctivitis that had nodules and swollen lesions and was suspected to be caused by a viral agent. Various common tests for virus identification based on the symptoms of the infected turkeys, such as general serologic tests (e.g. fluorescent antibody, agar gel immunodiffustion, hemagglutination-inhibition, virus neutralization), and molecular assays (e.g. PCR) came out negative. CNT-STEM was used with NGS as the last resort. First, 5 mL tissue homogenate was filtered through a membrane filter of 0.45 µm pore size. Then 750 µL filtrate was enriched and concentrated to 50 µL by a CNT-STEM of 25 nm inter-tubular distance and analyzed by NGS. From the CNT-STEM processed sample, 3.81% of the total NGS reads were viral reads (50,076/1,263,289), in contrast to only 0.001% viral reads (17/1,626,134) from 50 µL of the original membrane filter tissue filtrate without CNT-STEM enrichment/concentration. The NGS reads represent an enrichment factor of $3.8\times10^3$. After assembly, two viral contigs were obtained with an average coverage of 1,056. The nucleotide BLAST search identified this putative viral agent as a new variant strain of infectious bursal disease virus (IBDV) with less than 94-95% similarity to other reported IBDV strains in the USA (FIG. 45A). iSNV analysis identified 4 iSNV sites, where 2 iSNV resulted in amino acid changes. Phylogenetic analysis and BLAST search results indicated that this is indeed a novel strain (IBDV/turkey/PA/00924/14), close to an IBDV strain of serotypes 2 isolated from turkeys in Ohio, USA (FIG. 45B, FIG. 46, FIG. 47A, FIG. 47B). Serotype 2 is relatively rare for sequenced and identified IBDVs, and it is suspected this is the reason why initial serologic and molecular tests failed to identify the virus. Moreover, the viral agent was observed under TEM, and it consisted of "birnavirus-like" particles of ~65 nm in diameter, well matched with the IBDV identification (FIG. 8B inset). The virus was named "IBDV/turkey/PA/00924/14", and the sequence deposited with NCBI database under KP642112 (Segment A) and KP642111 (Segment B).

Carbon nanotubes are among the strongest materials on earth (Yu, M. F. et al., Science 2000, 287:637-640; Qian, D. et al., Appl. Mech. Rev. 2002, 55:495-533). The strength and stiffness of N-MWCNTs are comparable to pristine MWCNTs (Ganesan, Y. et al., ACS Nano 2010, 4:7637-7643). Since filtration is mainly a mechanical process, the high stiffness of the constructing nanomaterial enables the fabrication of a device with extremely high porosity up to 95% while still maintaining structure integrity during filtration. Therefore, the robustness of CNTs and the extremely high porosity of the N-MWCNT arrays distinguish the present CNT-STEM technology from other existing ultrafiltration techniques; at least two orders of magnitude lower in normalized flow resistance compared with commercial ultrafiltration membranes (FIG. 48). This high porosity is critical for reducing flow resistance, preventing device clogging, and decreasing CNT material usage to minimize negative effect in downstream virus analyses, all of which empower the CNT-STEM as a point-of-care platform for efficient virus sample preparation from animal and human samples.

It is also noteworthy that the overall success rate from device fabrication to testing is 76.8% out of 228 fabricated devices for these studies. In FIG. 49, the device yield and reliability were recorded and analyzed during the CNT-STEM fabrication, assembly and testing. The overall success rate from device fabrication to testing is 76.8% out of 228 fabricated devices. During device fabrication, the PDMS top chamber was aligned to the N-MWCNT forest patterns by naked eyes before bonding, 16 out of 228 devices (7.0%) failed because of the misalignment. Although the N-MWCNT forest structure can withstand pressure and forces during normal device operation, when it hits a hard surface during fabrication, it can still "crash". This kind of mishandling accounts for 2.6% of overall device failure. Finally prior to virus filtration, the flow rate was measured during the PBS wash. 31 out of 206 devices were found to have a leakage problem, which presented 58.5% (31/53) of all failure devices. The leakage is believed to be caused by some micro-scale damages of N-MWCNT structures, which compromised the integrity of the N-MWCNT porous wall and too miniscule to be observed under an optical microscope directly. To improve the yield of the device, some custom-made jigs or tools can be designed for automatic handling during the device fabrication, assembly and testing.

Device failing is due to leakage (13.6%), misalignment of PDMS-CNTs (7.0%) and N-MWCNT structure inhomogeities (2.6%). However, all these can be improved by further microfabrication tuning. For leakage, a simple and effective method was developed to evaluate it (before introducing real samples), by measuring the flow rate of buffer solution through the CNT-STEM device.

The tunable range of the inter-tubular distance of N-MWCNT (17-325 nm) spans the majority of the virus size spectrum, and provides unique flexibility in device design/fabrication able to reach the best performance for different viruses. In order to prepare samples for NGS, it is preferable to use CNT-STEM with larger inter-tubular distance if host ribosome RNA (rRNA) is a concern; larger inter-tubular distance will not trap ribosomes (~20 nm in diameter). Thus, CNT-STEM with 95 nm inter-tubular distance was used for the AIV samples targeted for NGS analysis. This is also justified for mimicking H5N2 swab samples: the rRNA reads reduced from 985,397 (41.7% of total reads) to 33,735 (2.6% of total reads) after the CNT-STEM sample preparation. For viruses of small size or samples with unknown viruses, it is more preferable to test viruses with devices of smaller inter-tubular distance. CNT-STEM of 25 nm inter-tubular distance was used to enrich and concentrate unknown viruses from the turkey eyelid tissue sample, and it turned out that the isolated IBDV was smaller than the previously tested AIV (65 nm vs 93 nm).

It has been reported that high concentration of CNTs can inhibit PCR while low concentration of CNTs may enhance it. The present experiments demonstrate there was no noticeable effect of N-MWCNT on the Ct values of the rRT-PCR. The weight of N-MWCNTs inside each CNT-STEM was measured as 26 μg, which corresponds to a final concentration of 0.5 μg/μL in the rRT-PCR reaction mixture. The concentration is consistent with the previously reported CNT concentration ranges that have no effect or can enhance PCR.

In both the rRT-PCR virus detection and the ECE virus isolation experiments, the improvement correlates with the volume ratio of the original sample to that of the re-suspended sample after enrichment, which underlines the importance of the optimal sample concentration provided by the CNT-STEM. Concentration effects can account for a large part of the improvement of rRT-PCR and virus isolation, since the contaminating materials do not significantly affect the highly specific rRT-PCR virus detection and they are non-proliferable in embryonated chicken eggs. However, the contaminant removal and sample concentration are key for the whole genome sequencing using NGS, because random primers are used that do not distinguish viral targets from other contaminating genetic materials.

The CNT-STEM reported here provides a unique platform of a nanomaterial-integrated microfluidic device for label-free enrichment and concentration of viruses from field samples. By engineering the bottom-up synthesis process, N-MWCNTs arrays were selectively grown on device substrates and then integrated directly into microfluidic devices. This combined bottom-up synthesis and top-down microfabrication makes the production of the device potentially scalable and low cost. The unique properties of the vertically aligned N-MWCNT enable the CNT-STEM to enrich viable virus particles, and remove host and environmental contaminants in a highly efficient way. The tunable size range of the CNT-STEM covers the size of most of the reported viruses. This novel technology was demonstrated to significantly improve current rRT-PCR and virus isolation in avian influenza virus surveillance. More importantly, it enables genomic sequencing using NGS directly from real field samples without virus amplification. Since neither CNT-STEM based virus sample preparation nor NGS requires prior knowledge of the viruses inside the sample, this combination provides a unique and powerful approach for novel and emerging virus discovery, thus significantly contributing to the control and eradication of viral infectious diseases.

Example 4: Plant Plum Pox Virus (PPV) Enrichment

A feasibility study of PPV enrichment was performed by CNT-STEM. CNT-STEM with 25 nm inter-tubular distance was used to enrich PPV samples. The enrichment results were measured by RT-PCR. FIG. 50A shows the Ct values of PPV serial dilution samples after being processed by current a USDA protocol and by CNT-STEM. Overall, CNT-STEM has better PPV enrichment performance compared to the current USDA protocol. Under PPV with 100× dilution, CNT-STEM improved the Ct value by ~7, which corresponds to ~100 times better yield compared to the current USDA standard protocol. This preliminary study demonstrated the feasibility of CNT-STEM as an effective sample preparation platform for PPV field sample preparation.

The materials and methods of the feasibility study are now described.

Leaf Sample Preparation

A set of plant grinding bags were labeled for the number of samples to be tested, wherein each laboratory sample should consist of no more than 8 leaves. The leaves were stacked on top of each other and a portion of the leaves were torn nearest to the petiole end, along the mid rib on the remaining side of the leaves. 0.3 g of each sample were weighed and placed in the corresponding grinding bag between the mesh layers of the grinding bag. Samples were kept on ice.

Pre-chilled GEB4 grinding buffer was added to each bag at 1:10 ratio (tissue weight in g: buffer volume in mL). A tissue homogenizer device was used to grind the leaves into sap from the outside of the bag. After grinding, the bags of ground sap were kept in ice until loading. At least 500 μL of ground sap into a 1.6 mL disposable microcentrifuge tube. All processed samples should be loaded into a prepared plate within 1-2 hours of grinding.

One-Step RT-PCR

All reagents, primers, and probes were thawed at room temperature, except the SuperScript® III RT/Platinum® Taq Mix and RNaseOUT were kept on ice. All thawed reagents were vortexed at a setting of 7-10 until well homogenized. Vortexed tubes were spun for 15-30 seconds at >10,000 rpm in a bench-top microcentrifuge and kept on ice.

RT-PCR Set-Up

RT-PCR TaqMan was performed with Invitrogen's SuperScript® III Platinum® One-Step qRT-PCR Kit. The kit consists of 2× Reaction Mix (containing RT-PCR buffer, 3 mM Mg and dNTPs), 50 mM MgSO$_4$ and SuperScript® III RT/Platinum® Taq Mix. The kit also contains ROX Reference Dye, which was not used. Master Mix preparation and aliquoting must be done in a decontaminated PCR workstation/enclosure on a new disposable lab mat.

A Cepheid cooling block was removed from a 4° C. refrigerator and placed in the PCR workstation. 20 μL of PPV Master Mix was prepared for each sample plus 4-6 control tubes plus 1 extra mix for every 10 reactions needed. For example, for 20 reactions, 22 volumes of PPV Master Mix was prepared. Each volume of PPV Master Mix contained: 3.5 μL Molecular Grade Water; 12.5 μL 2× Reaction Mix; 1.5 μL 50 mM MgSO$_4$; 1 μL 5 μM Sch FRD-REV primer mix; 0.5 μL 5 μM Sch probe; 0.5 L 40 u/μL RNaseOUT; and 0.5 μL SuperScript® III/Platinum® Taq Mix. Master Mix was mixed by pipetting gently up and down 2-3 times and kept on ice. SmartCycler® tubes (25 μL) were placed into the Cepheid cooling block, and the 20 μL volumes of Master Mix were pipetted into each tube. The tubes were taken to the PCR thermocycler station and 5 μL of RNA sample or control were added to the appropriate tubes to yield a total reaction volume of 25 μL.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of filtering particles of a specific size out of a solution, the method comprising:
   passing a solution through a filter, the filter comprising a plurality of vertically-aligned carbon nanotubes (VACNT) forming a VACNT row, each VACNT being separated by a VACNT gap having a VACNT gap size, wherein at least one VACNT gap size is different from another VACNT gap size;
   capturing a particle having a particle size commensurate with the VACNT gap size so that different sized particle are releasably captured in an appropriate sized VACNT gap, the capture mechanism consisting essentially of the particles fitting in the VACNT gaps via mechanical interference; and
   allowing the solution to exit the filter as a filtered solution.

2. The method of claim 1, wherein the filter comprises a metal catalyst thin film attached to the VACNT, the method further comprising:
   adjusting a thickness of the metal catalyst thin film to tune gap size, diameter, and density of at least one VACNT.

3. The method of claim 1, the method further comprising: fabricating the filter.

4. The method of claim 1, wherein:
   the solution is derived from any one or combination of an animal, a human, a plant, or an organism.

5. The method of claim 1, wherein:
   forming an array of VACNT rows, the VACNT gap for a first row being different from a VACNT gap for a second row.

6. A method of capturing particles of a specific size out of a solution for analysis, the method comprising:
   passing a solution through a filter, the filter comprising a plurality of vertically-aligned carbon nanotubes (VACNT) forming a VACNT row, each VACNT being separated by a VACNT gap having a VACNT gap size, wherein at least one VACNT gap size is different from another VACNT gap size;
   capturing a particle having a particle size commensurate with the VACNT gap size so that different sized particles are releasably captured in an appropriate sized VACNT gap, the capture mechanism consisting essentially of the particles fitting in the VACNT gaps via mechanical interference.

7. The method of claim 6, wherein the filter comprises a metal catalyst thin film attached to the VACNT, the method further comprising:
   adjusting a thickness of the metal catalyst thin film to tune gap size, diameter, and density of at least one VACNT.

8. The method of claim 6, the method further comprising: fabricating the filter.

9. The method of claim 6, the method further comprising: analyzing the captured particle.

10. The method of claim 6, the method further comprising:
    enriching the captured particle.

11. The method of claim 6, the method further comprising:
    releasing the captured particle and analyzing the released captured particle.

12. The method of claim 6, the method further comprising:
    releasing the captured particle, wherein the released captured particle is viable.

13. The method of claim 6, the method further comprising:
    releasing the captured particle via mechanical abrasion of at least one VACNT.

14. The method of claim 6, the method further comprising:
    releasing the captured particle via degrading nanostructures of at least one VACNT.

15. The method of claim 6, wherein the solution is derived from any one or combination of an animal, a human, a plant, or an organism.

16. The method of claim 15, the method further comprising:
    diagnosing the animal, the human, the plant, and/or the organism as being a host to the captured particle.

17. The method of claim 16, the method further comprising:
    diagnosing the animal, the human, the plant, and/or the organism as having a disease indicative of the captured particle.

18. The method of claim 6, wherein:
    forming an array of VACNT rows, the VACNT gap for a first row being different from a VACNT gap for a second row.

* * * * *